United States Patent [19]

Nishikori et al.

[11] Patent Number: 5,627,584
[45] Date of Patent: May 6, 1997

[54] ENDOSCOPE SYSTEM WITH CENTRALIZED CONTROL OF ASSOCIATED PERIPHERAL EQUIPMENT

[75] Inventors: Toshiaki Nishikori, Sagamihara; Yasuyuki Kaneko, Yokohama; Atsushi Amano; Masahiko Hamano, both of Hachioji; Kazufumi Takamizawa, Chofu; Hideyuki Shoji; Mutsumi Oshima, both of Hachioji; Ken-ya Inomata, Mitaka, all of Japan

[73] Assignee: Olympus Optical Co., Ltd., Tokyo, Japan

[21] Appl. No.: 325,628

[22] Filed: Oct. 19, 1994

Related U.S. Application Data

[63] Continuation of Ser. No. 51,812, Apr. 26, 1993, abandoned, which is a continuation-in-part of Ser. No. 820,994, Jan. 15, 1992, abandoned.

[30] Foreign Application Priority Data

Jan. 17, 1991 [JP] Japan ..................... 3-004026

[51] Int. Cl.⁶ .................................................. H04N 7/18
[52] U.S. Cl. ..................... 348/72; 348/65; 348/68; 348/73
[58] Field of Search ........................ 348/77, 75, 74, 348/65, 76; 128/6; 600/102, 118

[56] References Cited

U.S. PATENT DOCUMENTS

| | | | |
|---|---|---|---|
| 3,690,769 | 9/1972 | Mori | 356/41 |
| 4,350,488 | 9/1982 | Davis | 433/32 |
| 4,473,841 | 9/1984 | Murakoshi et al. | 358/98 |
| 4,589,404 | 5/1986 | Barath et al. | 348/67 |
| 4,604,992 | 8/1986 | Sato | 348/67 |
| 4,618,885 | 10/1986 | Nagasaki et al. | 358/98 |
| 4,638,800 | 1/1987 | Michel | 128/303.1 |
| 4,716,897 | 1/1988 | Noguchi et al. | 128/303.15 |
| 4,776,086 | 10/1988 | Kasevich et al. | 29/828 |
| 4,854,301 | 8/1989 | Nakajima | 128/4 |
| 4,865,018 | 9/1989 | Kanno et al. | 358/98 |
| 4,989,083 | 1/1991 | Eino | 358/98 |
| 4,996,975 | 3/1991 | Nakamura | 348/74 |
| 4,998,972 | 3/1991 | Chin et al. | 358/98 |
| 5,051,823 | 9/1991 | Cooper et al. | 348/67 |
| 5,078,150 | 1/1992 | Hara et al. | 358/98 |
| 5,099,846 | 3/1992 | Hardy | 128/653.1 |
| 5,115,374 | 5/1992 | Hongoh | 358/400 |
| 5,135,534 | 8/1992 | Tulip | 606/178 |
| 5,153,721 | 10/1992 | Eino et al. | 358/98 |
| 5,184,601 | 2/1993 | Putman | 348/77 |
| 5,200,838 | 4/1993 | Nudelman et al. | 348/77 |
| 5,235,510 | 8/1993 | Yamada et al. | 364/413.02 |
| 5,277,172 | 1/1994 | Sugimoto | 348/77 |

FOREIGN PATENT DOCUMENTS

| | | |
|---|---|---|
| 3284230 | 12/1991 | Japan . |
| 3284232 | 12/1991 | Japan . |

*Primary Examiner*—Tommy P. Chin
*Assistant Examiner*—Anand S. Rao
*Attorney, Agent, or Firm*—Armstrong, Westerman, Hattori, McLeland & Naughton

[57] ABSTRACT

An endoscope system has an endoscope equipped with an imaging unit, and a plurality of peripheral equipment used in conjunction with the endoscope; such as, a light source for supplying illumination light to the endoscope and a video signal processor for processing a video signal originating from the endoscope, comprising a centralized operation unit for operating at least the light source and video signal processor and a centralized control for centralizing control of the light source and video signal processor based on a command sent from the centralized operation unit.

31 Claims, 52 Drawing Sheets

FIG.12(a)
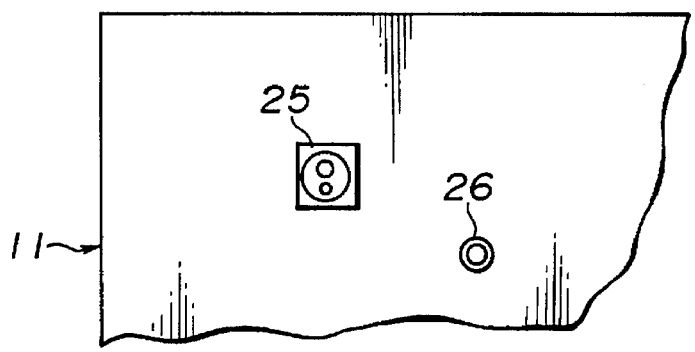
FIG.12(b)
FIG.12(c)
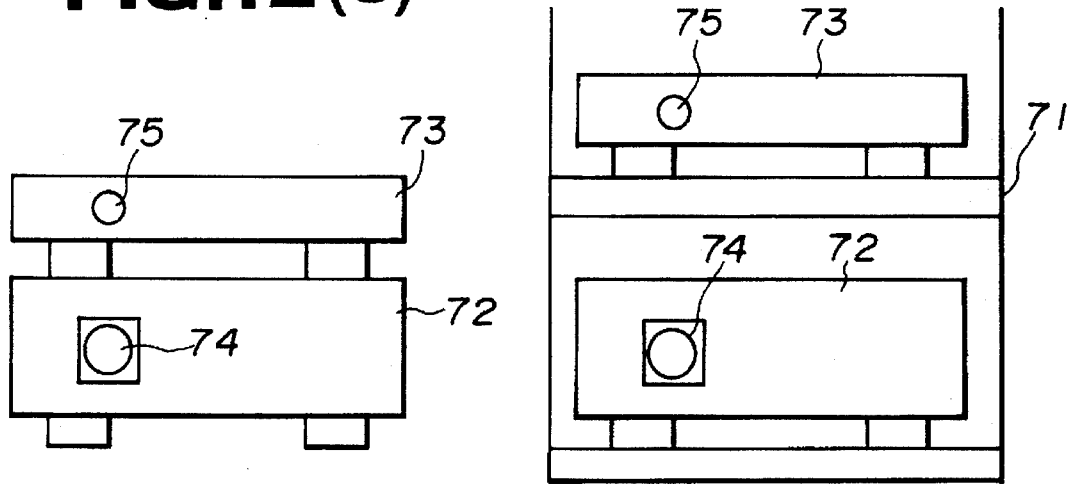

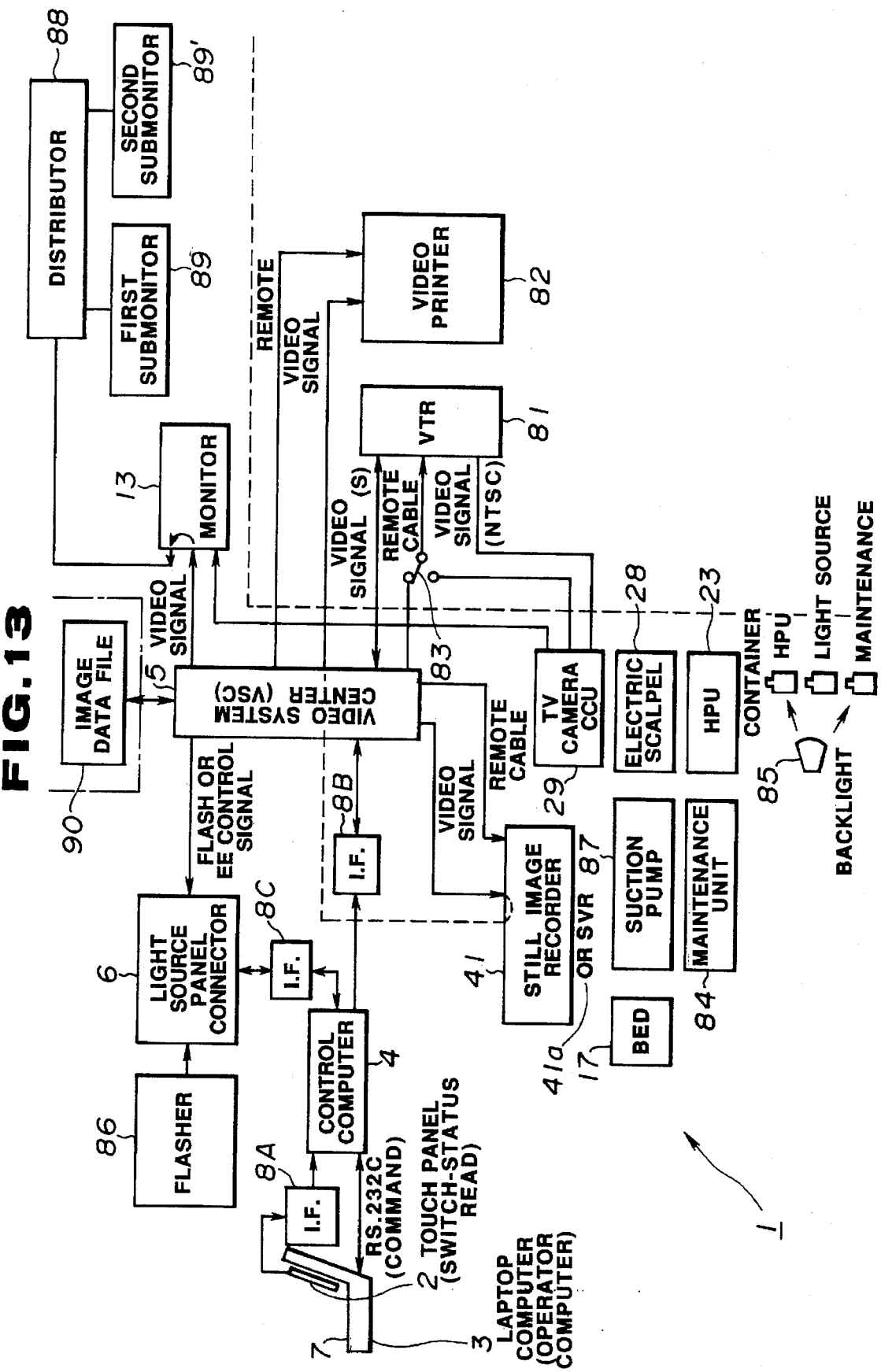

SCREEN CHANGE ROUTINE

TURNING ON/OFF SWITCHES IN CV-100 MODE

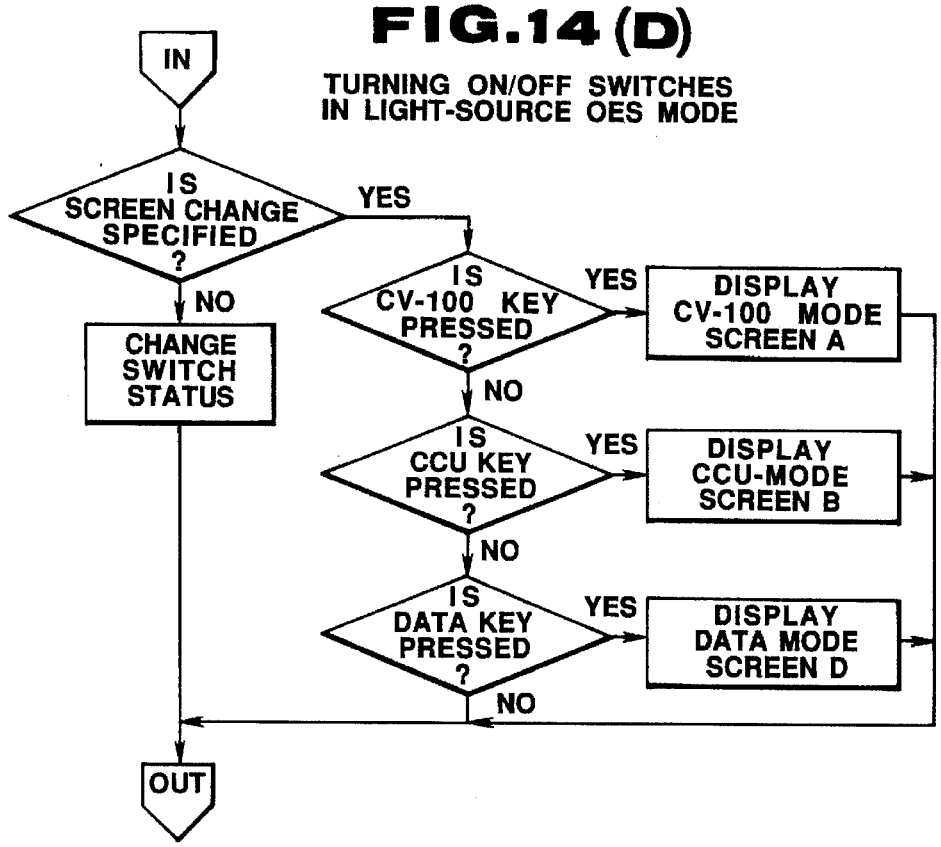
FIG. 14 (D) TURNING ON/OFF SWITCHES IN LIGHT-SOURCE OES MODE
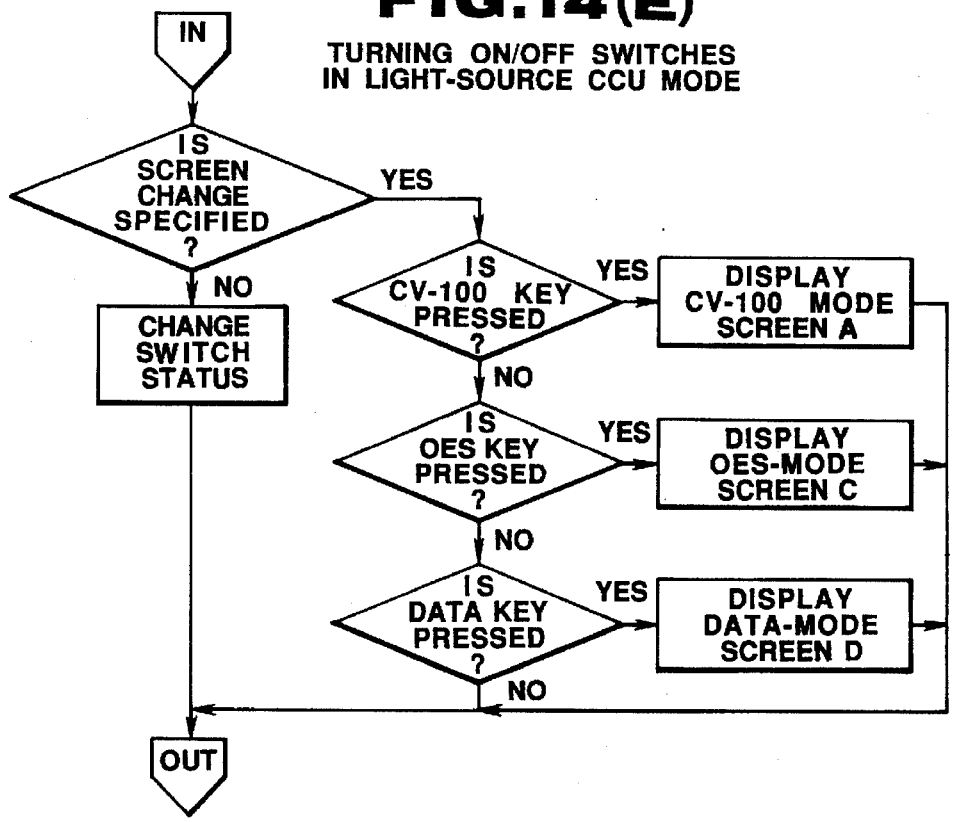
FIG. 14 (E) TURNING ON/OFF SWITCHES IN LIGHT-SOURCE CCU MODE

FIG.15(D)

FUNCTION KEY

| STOP WATCH | REMOVE DATA | EXTEND COM'NT | TITLE SCREEN | CURSOR | COLOR BARS | | HOME |
|---|---|---|---|---|---|---|---|
| RE-START | STORE MODE | | RECALL PAT'NT | PRESET | SCV RESET | | CLEAR |

ID. NO:

NAME:

SEX: AGE:

D. O. BIRTH:

COMMENT:

| CV100 | CCU | OES | | | DATA | | | |

FIG.15(F)

| ID. NO | NAME | | RECALL NO 12 |
|---|---|---|---|
| 01 | | | |
| 02 | | | |
| 03 | | | |
| 04 | | | |
| 05 | | | |
| 06 | | | |
| 07 | | | |
| 08 | | | |
| 09 | | | |
| 10 | | | |
| 11 | | | |
| 12 | | | |
| 13 | | | |
| 14 | | | |
| 15 | | | |
| 16 | | | |
| 17 | | | |
| 18 | | | |
| 19 | | | |
| 20 | | | |

FIG.15(I)

ID. NO      NAME                    ENTER NO 1      END 01
02
03
04
05
06
07
08
09
10
11
12
13
14
15
16
17
18
19
20

NAME:

SEX:

AGE:

D.O. BIRTH: / /

END

ST-PAT

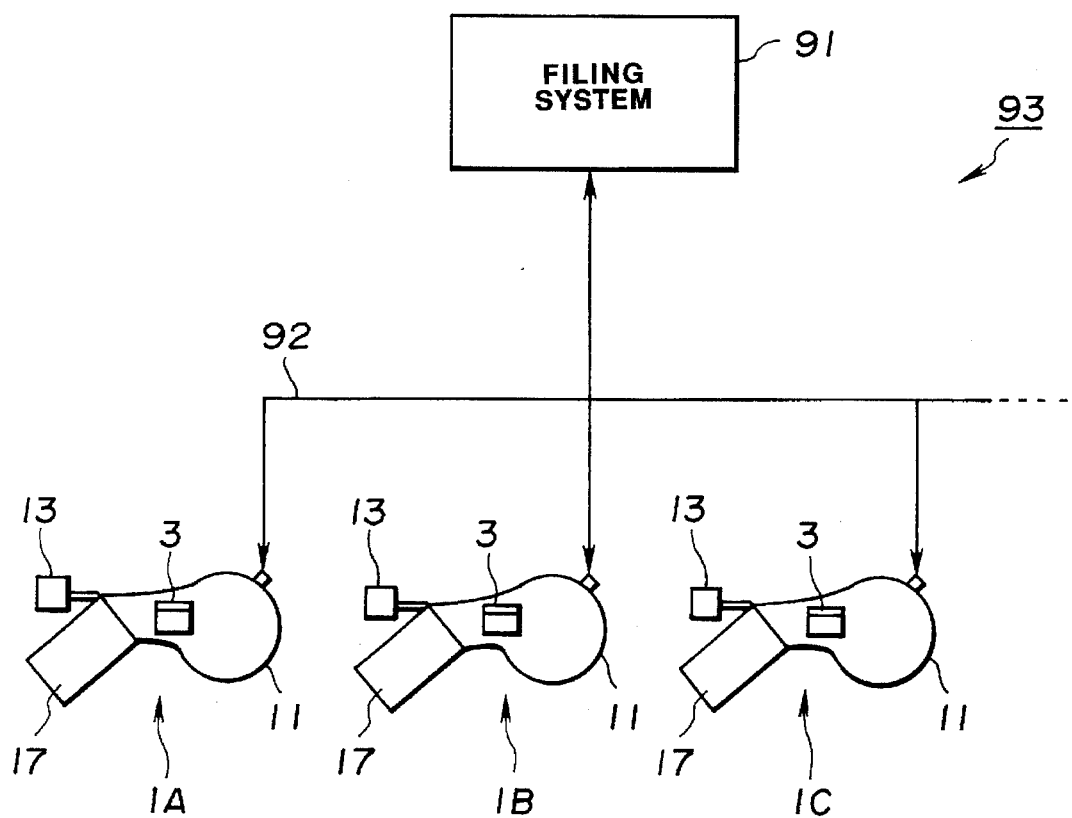

FIG.19　　FIG.20
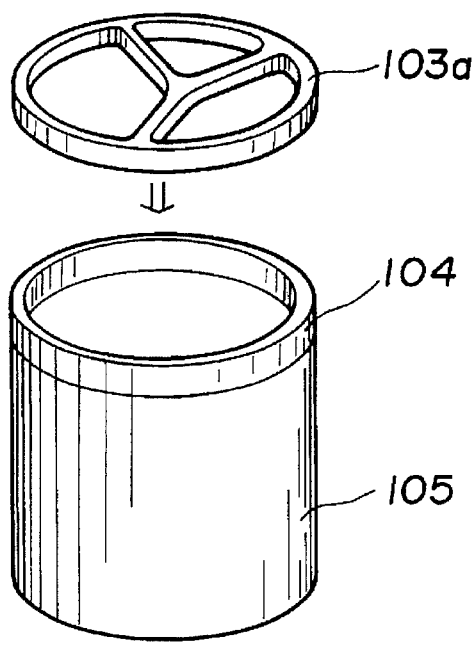
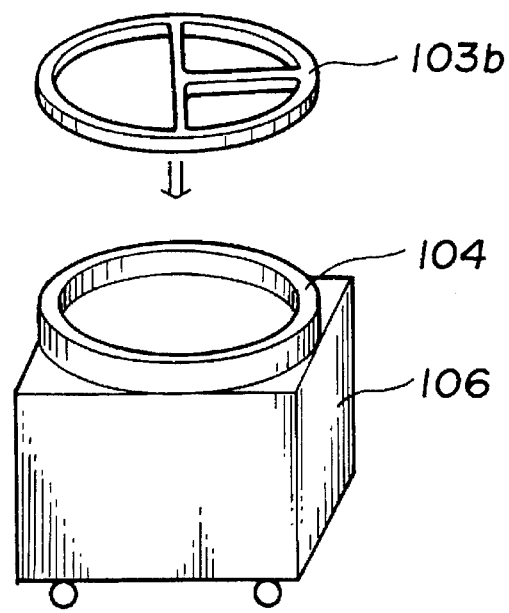
FIG.21
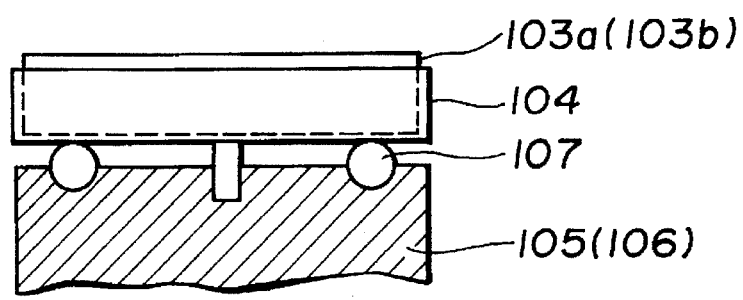

FIG. 34

(a) NORMAL EXAMINATION (DURING EXAMINATION)

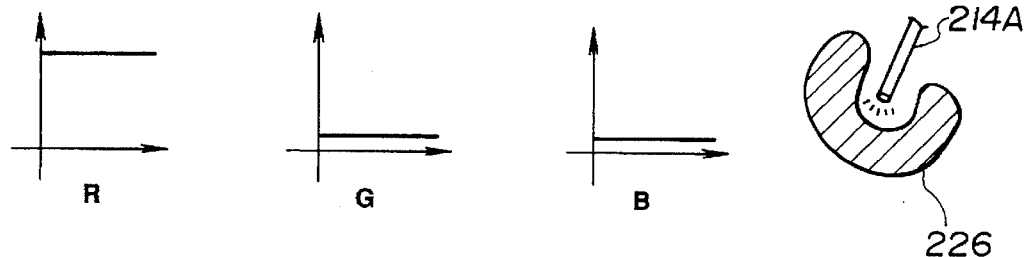

*THE COLOR OF A SUBJECTS CAVITY CONSISTS MAINLY OF R ELEMENTS. THEREFORE THE R SIGNAL IS HIGHER THAN G AND B SIGNAL.

(b) WHEN AN ENDOSCOPE IS IN CONTACT WITH THE WALL (DURING EXAMINATION)

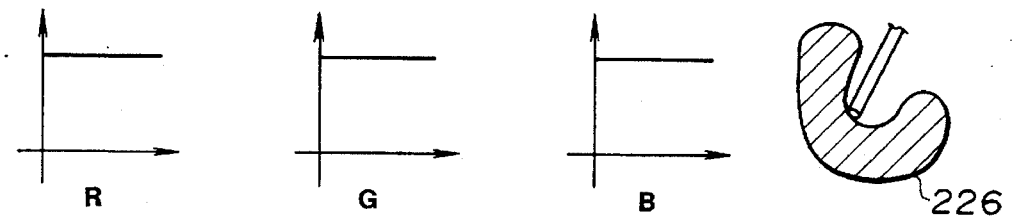

* WHEN AN ENDOSCOPE IS PLACED IN CONTACT WITH THE CAVITY WALL, WHITE HALATION IS OBSERVED UNTIL THE AUTOMATIC DIMMER OPERATE TO REDUCE THE QUANTITY OF LIGHT.

(c) WHEN AN ENDOSCOPE IS REMOVED (NON-EXAMINATION TIME)

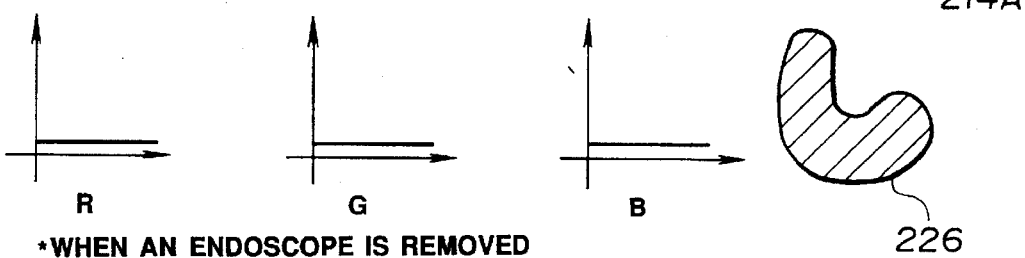

*WHEN AN ENDOSCOPE IS REMOVED R ELEMENTS ATTENUATE RAPIDLY.

(d) WHEN AN ENDOSCOPE IS NOT MOUNTED (NON-EXAMINATION TIME)

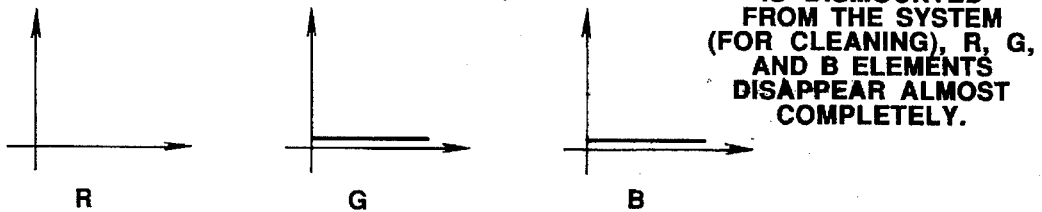

*WHEN AN ENDOSCOPE IS DISMOUNTED FROM THE SYSTEM (FOR CLEANING), R, G, AND B ELEMENTS DISAPPEAR ALMOST COMPLETELY.

ENDOSCOPE SYSTEM WITH CENTRALIZED CONTROL OF ASSOCIATED PERIPHERAL EQUIPMENT

This application is a continuation of application Ser. No. 08/051,812 filed Apr. 26, 1993, now abandoned, which is a continuation-in-part of application Ser. No. 07/820,994, filed Jan. 15, 1992, now abandoned.

BACKGROUND OF THE INVENTION

1. Field of the Invention

The present invention relates to an endoscope system having a control for centralizing control of a light source and other plurality of peripheral equipment for the endoscope system.

2. Description of the Related Art

In recent years, endoscopes have been widely adopted to observe an organ inside a body cavity by inserting an elongated insertion tube into the cavity or to undertake various kinds of treatment, if necessary, by routing treatment adapters through a treatment adapter channel. Furthermore, an electronic endoscope with a charge coupled device (CCD) or other solid-state imaging device at the distal end of the insertion tube has been in use.

In the field of medicine, for example, when an endoscope is used for diagnosis or treatment, an endoscope, a light source, and other equipment required are usually installed in a rack to form an endoscope system, then used for diagnosis or treatment.

In the endoscope system, diverse peripheral equipment are combined selectively depending on the purpose of use; for example, a light source for supplying illumination light to a subject via an endoscope, a video signal processor for processing a video signal originating from the endoscope, and an automatic imaging unit for forming optical images obtained with the endoscope, or a cautery hemostasis unit for cauterizing a lesion and a cautery power unit.

In the past, the peripheral equipment have been installed in a rack to form an endoscope system. In this case, equipment are operated independently. Then, observation or treatment is carried out. Thus, components are designed to be used independently. The components accommodated, for example, in a rack must be operated one by one. Depending on the arrangement of the rack or equipment, a doctor or a nurse who operates the endoscope system may have to operate equipment in an uncomfortable posture or move here and there to operate equipment. As a result, the operating procedure becomes complex or an environment most suitable for examination or treatment cannot be realized. For an endoscope system having a plurality of peripheral equipment, a function has long been awaited to operate peripheral equipment included in a system at a single station, centralize control of multiple equipment, or check the operating states of the multiple equipment at a single station.

The patent applicant has proposed an endoscope system having a chair equipped with operation switches in U.S. Pat. No. 4,854,301. In the system, the switches on the chair are used to operate equipment. This improves operability in endoscopic examination or treatment.

However, in the conventional system, although the switches are arranged at easy-to-operate locations, operation or control of peripheral equipment cannot be centralized. Therefore, it is impossible to actuate multiple different equipment or operate them in harmony using a single switch. Moreover, the operation switches are designed to operate specific units. Therefore, the arrangement of an operation unit or the combination of peripheral equipment cannot be changed flexibly.

Each of the peripheral equipment is provided with a power switch. The on or off operation of the power switch is performed unit by unit when it becomes necessary. The on or off operation of a light which is installed near an endoscope to illuminate a subject or an endoscope light, or room lights for an endoscope room is also done using an independent switch. Above all, when the room light switch being installed on the wall is concerned, if the quantity of light of the room lights must be adjusted, the user have to go to the wall and adjust the light adjustment variable resistor on the wall. The purpose of using an endoscope is oriented to treatment of a subject or identification of a lesion. If the power switches of units are turned on or off every before or after the units are used, it interrupts smooth treatment or identification. Therefore, the power switches of units are usually held on even if they are not used. That is to say, if an operator is obliged to turn on or off the power switches one by one during operation, it will be a great load to the operator. On the other hand, if all the power switches are held on, excessive power is consumed.

SUMMARY OF THE INVENTION

The principal object of the present invention is to provide an endoscope system which can centralize operation or control of peripheral equipment forming a system, and, thereby, minimize the load to an operator that he/she has to operate individual units, and improve system operability.

Other object of the invention is to provide an endoscope system which can control various equipment and lights without any difficulties, minimize the load to an operator that he/she has to operate complicated switches, and save excessive power consumption.

The other object of the invention is to provide an endoscope system which can centralize control of peripheral equipment according to a system configuration regardless of the types of the peripheral equipment.

Another object of this invention is to provide an endoscope system which can reduce erroneous operation of peripheral equipments in addition to the operation of a desired peripheral equipment even when centralized operation is performed in each peripheral equipment forming the endoscope system.

A further object of this invention is to provide an endoscope system which can prevent a whole endoscope system from becoming larger without making a display means for displaying an operating function of a peripheral equipment larger even when centralized operation is performed in each peripheral equipment forming the endoscope system.

The present invention relates to an endoscope system having an endoscope equipped with an imaging means, and a plurality of peripheral equipment used in conjunction with the endoscope; such as, a light source for supplying illumination light to the endoscope, and a video signal processor for processing a video signal originating from the endoscope. The endoscope system comprises a centralized operation means for operating at least the light source and video signal processor, and a centralized control means for centralizing control of the light source and video signal processor in response to a command sent from the centralized operation means.

The other features and advantages of the present invention will be apparent in conjunction with the description below.

BRIEF DESCRIPTION OF THE DRAWINGS

FIGS. 1 to 15 relate to the first embodiment of the present invention;

FIGS. 1 and 2 are block diagrams showing the configuration of the main section of the first embodiment;

FIG. 3 is a front view of an endoscope main unit;

FIG. 4 is a plan of a control main unit;

FIG. 5 is a rear view of the control main unit;

FIG. 6 is a right lateral view of the control main unit;

FIG. 7 is a left lateral view of the control main unit;

FIG. 8 is a front view showing the outline of the control main unit with a cover open;

FIG. 9 schematizes the oblique view of the control main unit;

FIG. 10 is an explanatory diagram showing a laptop computer support mechanism;

FIG. 11 shows the A—A cross section of FIG. 10;

FIG. 12 is a front view showing the positional relationships between a light source connector receptacle and a signal connector receptacle;

FIG. 13 is a configuration diagram showing the overall configuration of the first embodiment;

FIG. 14 is a flowchart showing the contents of the operations of a control computer and a laptop computer;

FIG. 15 is explanatory diagrams showing the screens displayed by the operations shown in FIG. 14;

FIG. 16 is an explanatory diagram showing a composite endoscope system in which a plurality of endoscope systems are installed as terminals;

FIGS. 19 to 21 relate to the first example of an endoscope tray;

FIG. 19 is an oblique view of a table for loading the tray;

FIG. 20 is an oblique view of a cart for loading the tray;

FIG. 21 is a cross-sectional diagram showing the rotation mechanism of a base;

FIG. 22 is an oblique view of a base and the tray;

FIG. 23 is an oblique view of the tray;

FIG. 24 is a plan showing the base and tray;

FIG. 30 schematizes the overall configuration of an endoscope system;

FIG. 31 is a front view of a centralized operation panel in the system shown in FIG. 30;

FIGS. 32 to 38 relate to the seventh embodiment of the present invention;

FIG. 32 is an explanatory diagram showing an endoscope system and an endoscope room;

FIG. 33 schematizes the overall configuration of the endoscope system;

FIG. 34 is an explanatory diagram showing the operation of the endoscope system;

FIG. 35 shows an appearance of the endoscope system;

FIG. 37 shows an appearance of an endoscope system storage rack having an endoscope storage holder different from that shown in FIG. 35;

FIG. 38 shows an appearance of the endoscope storage holder of the endoscope system shown in FIG. 37;

FIGS. 39 to 48 relate to the eighth embodiment of the present invention;

FIG. 39 is a perspective view of an endoscope room;

FIG. 40 is a front view of a centralized operation panel;

FIG. 41 schematizes an overall configuration of an endoscope system;

FIG. 42 shows an appearance of an endoscope system storage rack;

FIG. 43 shows an appearance of an endoscope storage hanger trolley;

FIG. 44 shows an appearance of the endoscope system storage rack using a vinyl sheet;

FIG. 45 shows an appearance of an endoscope storage holder having a paper bag;

FIG. 46 shows an appearance of a portable endoscope storage holder;

FIG. 47 shows an appearance of an endoscope storage holder whose endoscope hook is formed as part of the frame;

FIG. 49 schematizes the configuration of an illumination control;

FIG. 50 is a front view of a centralized operation panel;

FIG. 52 is a configuration diagram of an endoscope system;

FIG. 53 is an explanatory diagram of a switching means;

FIG. 54 is a configuration diagram of an endoscope system; and

FIG. 55 is an explanatory diagram of a switching means.

DETAILED DESCRIPTION OF THE PREFERRED EMBODIMENTS

FIGS. 1 to 15 show the first embodiment of the present invention.

Figure 1:
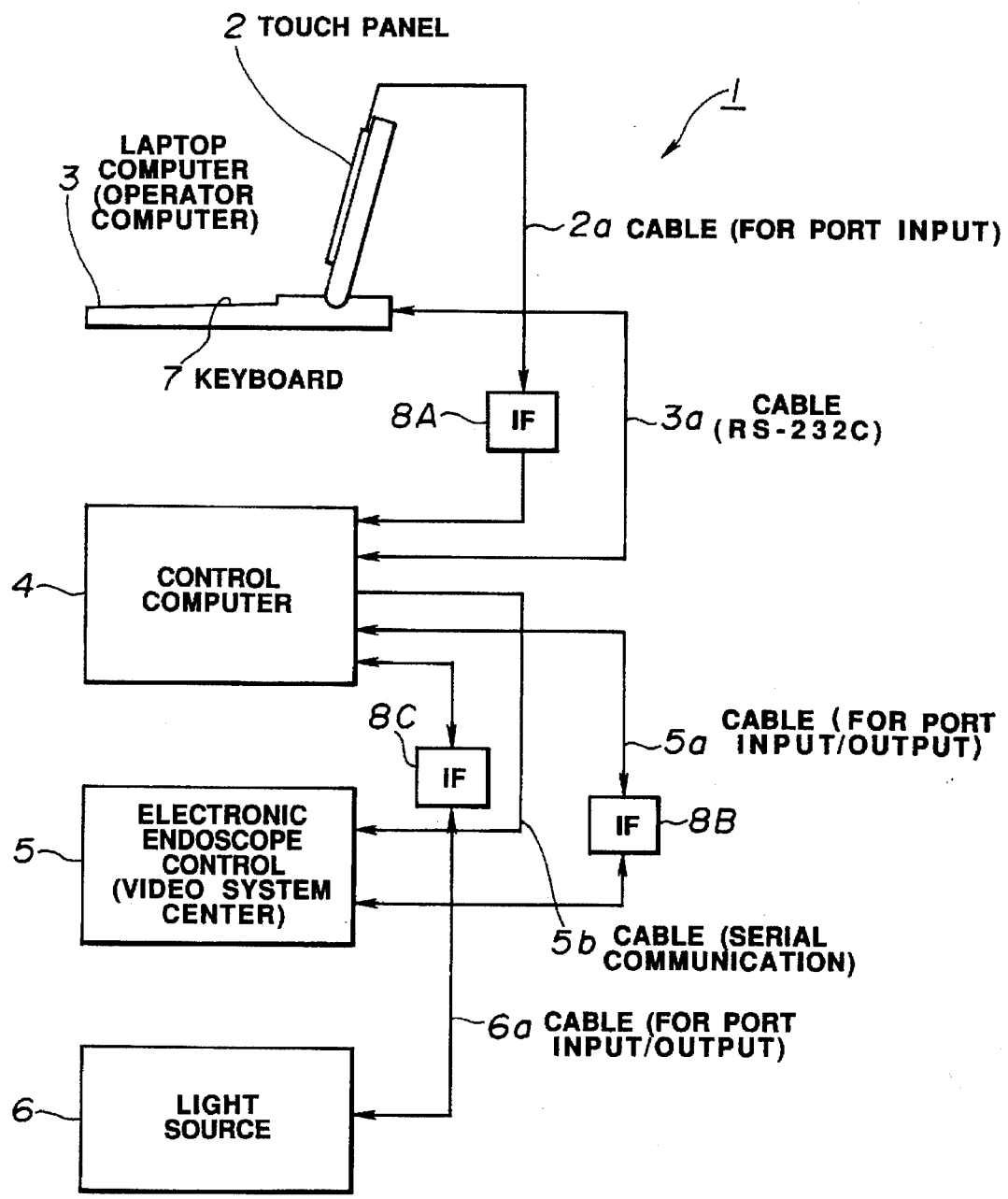
Figure 2:
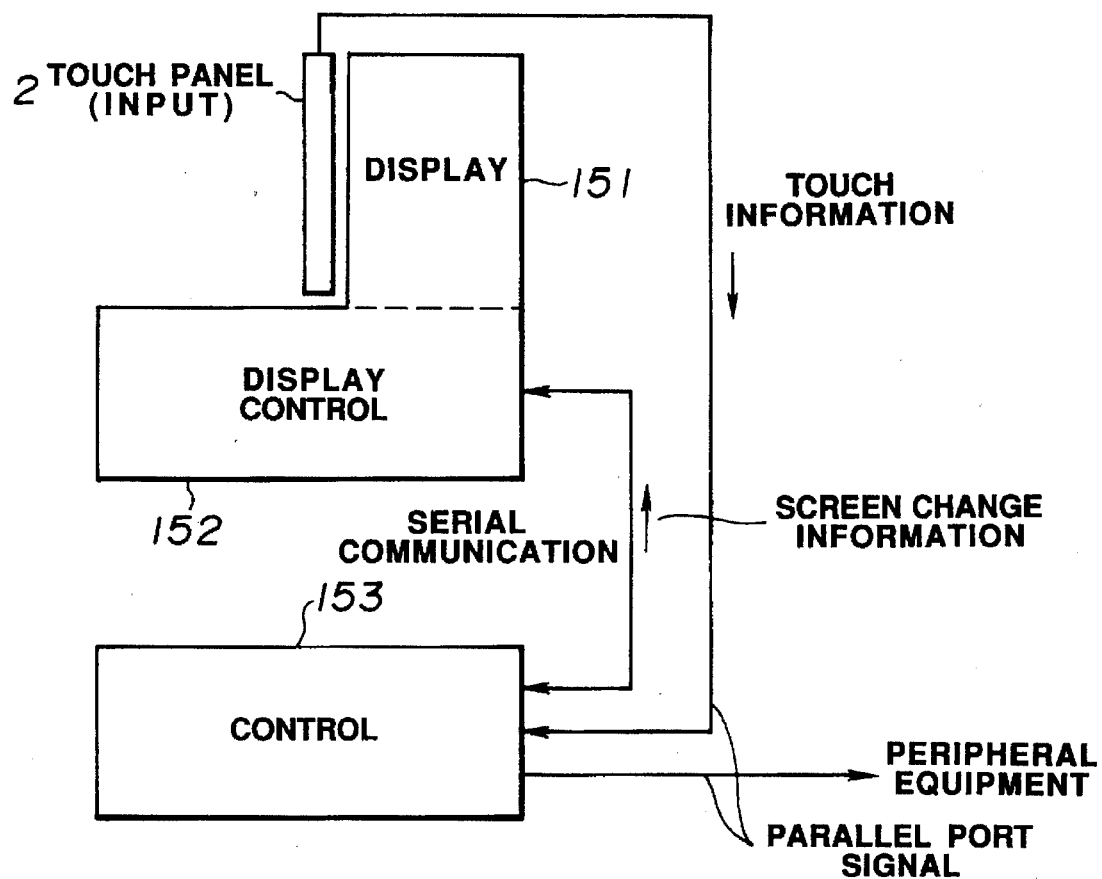

First of all, the main section of the first embodiment is explained in conjunction with FIG. 1 and 2. Then, the system according to the first embodiment is explained in detail.

As shown in FIG. 1, the main section of an endoscope system 1 according to the first embodiment comprises a laptop personal computer (operation computer) having a touch panel 2 forming a centralized operation unit or a centralized operation means, a control personal computer (control computer) 4 or a centralized control means for centralizing control or management of components (peripheral equipment) forming the system 1, which is connected to the touch panel 2 and operation computer 3 with a cable 2a passing through an interface 8A and a cable 3a respectively, an electronic endoscope control unit (referred to as a video system center (hereafter, VSC)) or a component connected to the control computer 4 with cables 5a and 6a passing through interfaces 8B and 8C respectively, and a light source 6.

The touch panel 2 comprises transference electrodes, or a plurality of switches arranged in the form of a matrix. When a scanning means is used to scan the matrix in the X (horizontal) and Y (vertical) directions, the coordinates of a switch pressed can be detected. That is to say, the control computer scans I/O ports to detect which part of the touch panel 2 attached to the display of the control computer 3 has been pressed (touched), then fetches the data at the coordinates. This means that touch detection and coordinate data is input from the touch panel 2 to the I/O ports of the control computer 4 via a cable 2a. Then, the control computer 4 transmits a command for changing the display screen to the operation computer 3 via a cable 3a according to the switch pressed. The cable 3a is, for example, an RS-232C, permitting bidirectional data communication.

The operation computer 3 changes the display screen or its own operation mode in response to a command sent from the control computer 4 (for example, from the VSC 5 control mode to the light source 6 control mode). When the operation computer 3 is placed in a mode in which a keyboard 7 is scanned to transmit data specified (which is referred to, for example, a data mode), it transmits the data to the control computer 4. Then, the control computer 4 converts the key code or the data specified with the keyboard 7 and sent from the operation computer 3 into a command corresponding to the code of a key on the keyboard of the VSC 5 (or a command output when the operation panel of the VSC 5 is operated), then transmits the command to the VSC 5 via the interface 8B of the VSC 5. The command is transmitted over the cable 5a. The cable 5a is used to detect the state of the VSC 5. Therefore, the cable 5a designed for inputting or outputting signals into or from ports is employed for transmitting commands.

Other cable 5b is designed for serial communication and transmits a TTL signal from the control computer 4 to the VSC 5 so that the signal data can be input to the VSC 5.

The control computer 4 converts a key code specified by operating the keyboard 7 into a command corresponding to a code of a key on the keyboard of the light source 6, then transmits the command to the light source via the interface 8C. The state of the light source 6 is also transmitted via the cable 6a and detected by the control computer 4.

In the first embodiment, a signal corresponding to a command entered by operating the operation panel of the VSC 5, for example, is generated by the control computer 4 based on the signal specified by operating the touch panel 2 and keyboard 7. Thus, the VSC 5 can operate in the same way as when a switch on the operation panel is turned on electrically. More specifically, the interface 8B substitutes for the operation panel of the VSC 5. Then, the control computer 4 controls or manages the operation of the VSC 5 based on the signal sent from the operation computer 3 having the touch panel 2 in the same manner as when the operation panel of the VSC 5 is operated. Likewise, the control computer 4 controls or manages the operation of the light source 6. Thus, the control computer 4 centralizes control or management of the operations of multiple system components.

In the first embodiment, the port output of the control computer 4 is placed on the input lines of the operator panels of components. Thereby, the components can be controlled with output signals sent from the control computer 4 (identical to those sent by operating the operator panels). The internal configurations of the components need not be modified.

Specifically, as shown in FIG. 2, the operation computer 3 includes a display 151 for centralized operation and a display control 152. A touch panel 2 is mounted on the display 151 to be used as an input unit. The display control 152 is connected to a control computer 4 or a control 153 for centralized control of peripheral equipment via a serial cable. The control 153 is connected to the touch panel 2 and peripheral equipment via parallel interfaces.

In response to a command sent from the control 153, screen change information for centralized operation is transmitted to the display control 152 by serial communication. Based on the screen change information, the display control 152 changes screens on the display 151. That is to say, the operation screen changes depending on the control mode. When a given area of a screen on the touch panel 2 is pressed, touch information is input to the control 153. Thus, the control 153 detects the fact that an input is provided for peripheral equipment. Then, the control 153 transmits screen change information as described previously, then generates control signals and transmits them to the peripheral equipment.

According to the first embodiment, even if the number of components of an endoscope system 1 increases, the operations of the components can be centralized at a common touch panel 2 or keyboard 7. Therefore, even if the components are arranged in a decentralized manner, they can be operated at a single place. This permits a user-friendly system configuration. (In the first embodiment, the operations of main components which are used frequently are centralized at a single place.)

An operation computer 3 is used for man-machine interface. Therefore, software can be created in the form of a module. This allows users to write on input screens more freely. Display screen information for centralized operation is contained in the display control 152 of the operation computer 3. Therefore, the memory of the control computer 4 (control 153) is not consumed.

Different computers are used for man-machine interface and control. This permits independent development of software packages. The display control 152 is used to visualize screens. This contributes to reduction of a load to the software of the control 153.

Next, the configuration of an endoscope system 1 according to the first embodiment is explained more specifically in conjunction with FIGS. 3 and later.

Figure 9:
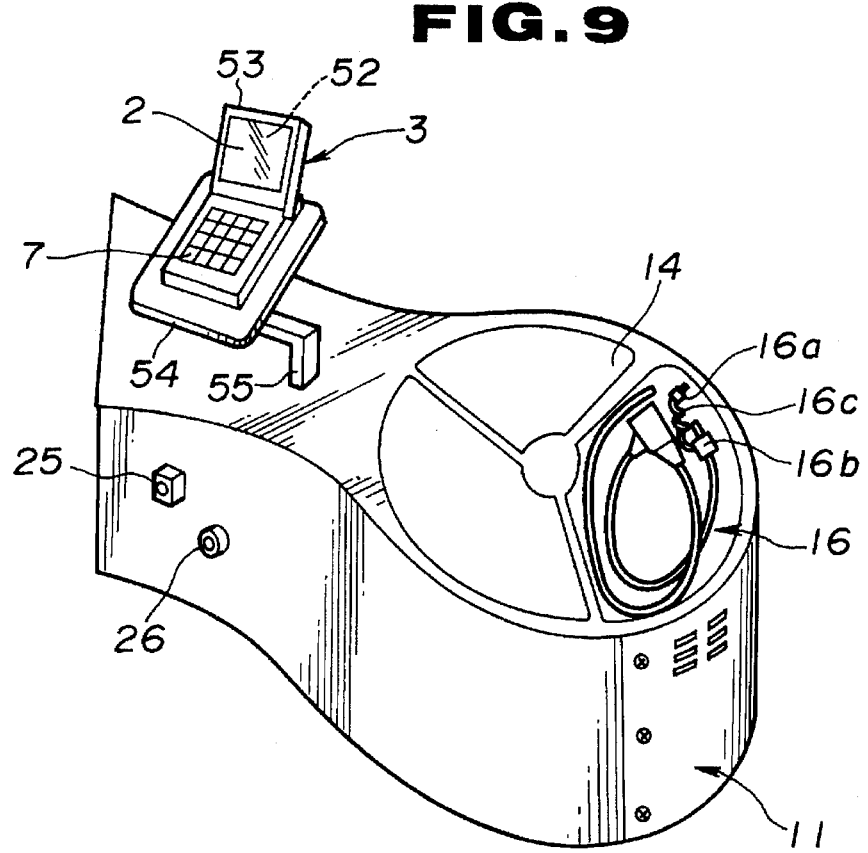

As shown in FIGS. 3 to 7, the endoscope system 1 according to the first embodiment comprises a control main unit 11, a monitor 13 mounted to an arm 12 extending from the control main unit 11, an operation computer 3 which is mounted on the top of the control main unit 11 to be freely rotatable, a circular tray 14 mounted on the top of the control main unit 11, and an endoscope employed; such as, an electronic endoscope 16 (See FIG. 9). A scope hanger 15 can be mounted on the control main unit 11 to be freely detachable. As shown in FIG. 9, the electronic endoscope 16 to be used for endoscopic manipulation, and treatment adapters and other accessories, which are not illustrated, can be placed in the tray 14. The tray 14 is mounted on the top of the control main unit 11 to be freely rotatable.

Figure 4:
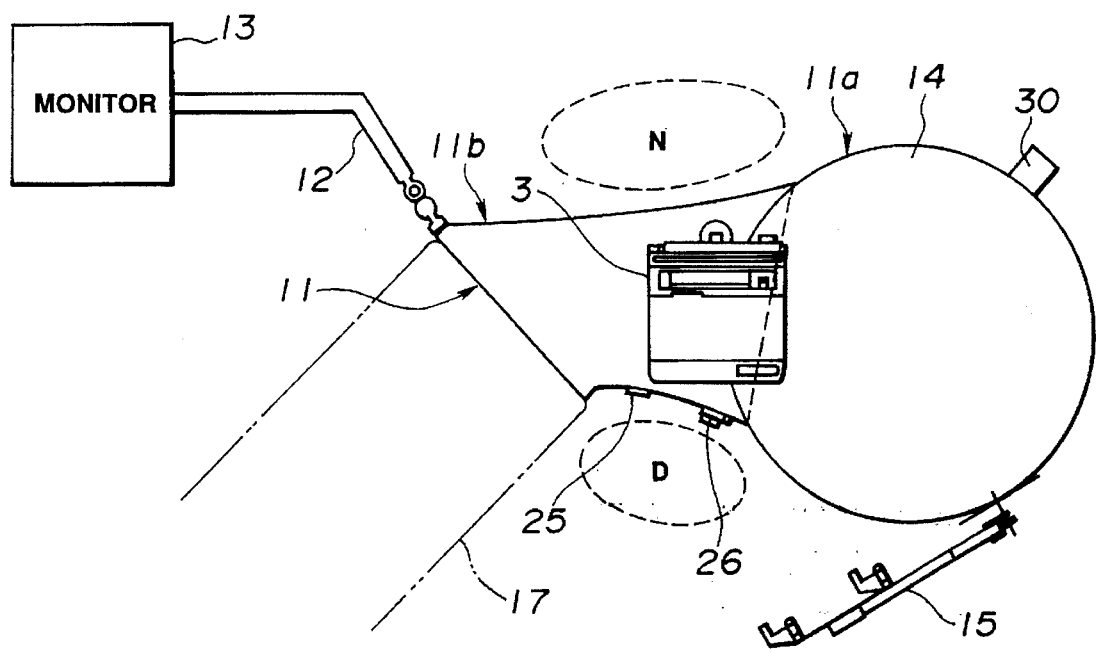

As shown in FIG. 4, the control main unit 11 comprises a columnar section 11a and a deformed square-pole section 11b coupled to the columnar section 11a. A bed 17 is arranged so that one end of the bed 17 will be aligned with the oblique plane formed on the external end of the deformed square-pole section 11b. The control main unit 11 is designed so that a position D facing the front of the deformed square-pole section 11b of the control main unit 11 will be an optimal position for a doctor or a primary user of the system, and a position N in the back of the deformed square-pole section 11b or on the opposite side of the position D, for a nurse or a secondary user of the system. The width between the front and back of the deformed square-pole section 11b is designed to be substantially two-thirds of the diameter of the columnar section 11a or 50 cm or less.

Figure 3:
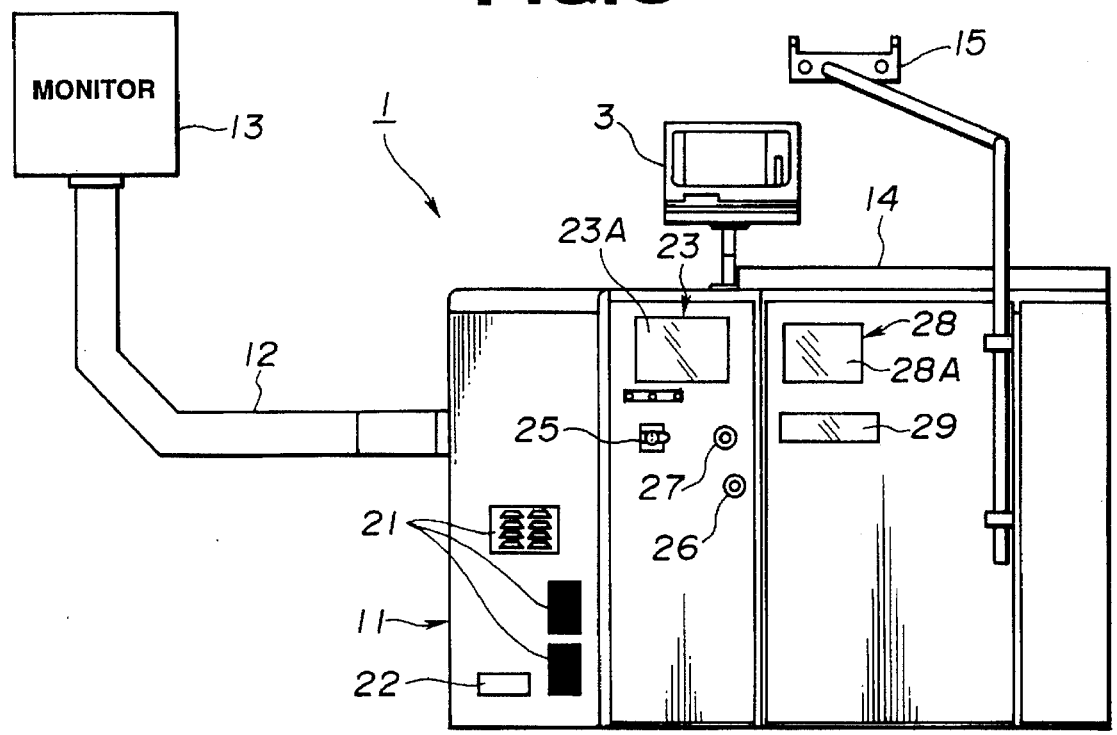

As shown in FIG. 3, the front of the control main unit 11 is laid out as follows: a duct 21, and a connector unit 22 including a foot switch connector, a P-plate connector, and a service socket on the oblique plane of the deformed square-pole section 11b on the side of the bed 17. A heat probe 23 for controlling hemostasis derived from heating coagulation is installed in the upper part of the deformed square-pole section 11b, and the main panel 23A of the heat probe 23 is coming out from the hollow on the front of the deformed square-pole section 11b opposing to a doctor. Under the main panel 23A, an endoscopic light source connector receptacle 25 for a light source which is not illustrated and a signal connector hanger 27 are arranged. A signal connector receptacle for an electronic endoscope 26 is installed under the signal connector hanger 27. Then, the light source connector of a fiberscope or an electronic endoscope is connected to the light source connector receptacle 25, and the signal connector of an electronic endoscope, the signal connector receptacle 26. An electric scalpel 28 is installed in the upper part inside the columnar section 11a, and a TV camera control (hereafter CCU) is installed under the electric scalpel 28. The main panel 28A of the electric scalpel 28 and the panel of the CCU 29 are coming out from two hollows on the columnar section 11a. To the CCU 29, a TV camera to be mounted to the eyepiece unit of the fiberscope is connected.

Figure 5:
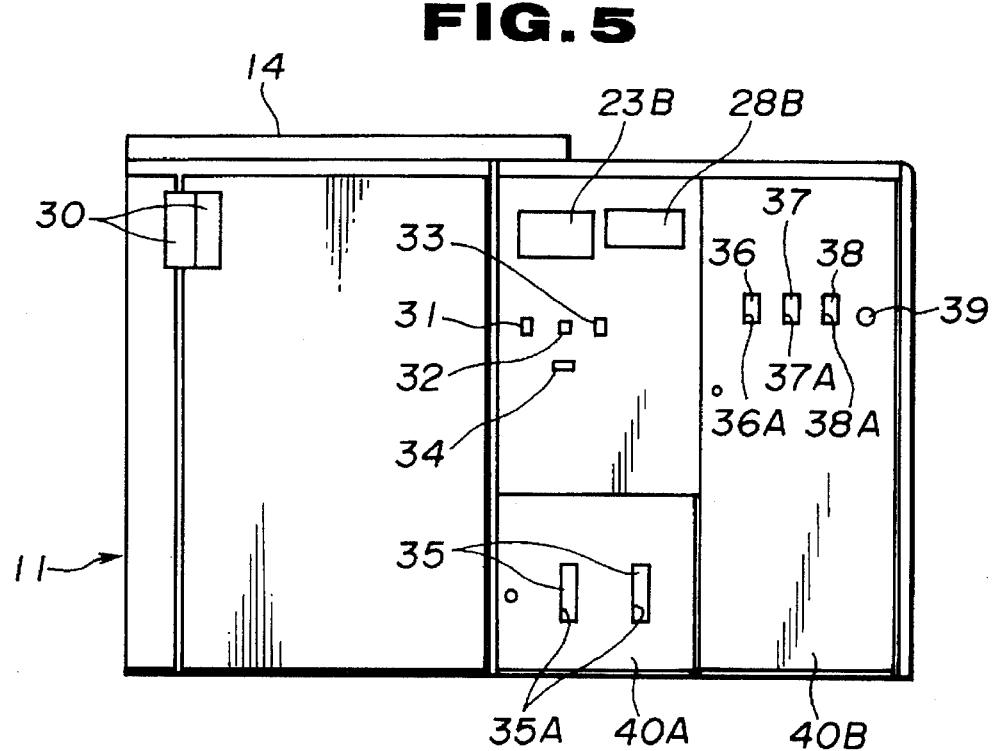

As shown in FIG. 5, the back of the control main unit 1 is laid out as follows: a subpanel 23B of the heat probe is installed in the upper left part, and the subpanel 28B of the electric scalpel 28, on the right of the subpanel 23B. Under these panels 23B and 28B, a power switch 3, an ignition switch 32, a suction switch 33, and a lamp life meter 34 are arranged, and aspirator containers are coming out. On the right side of the switches 31 to 33, a treatment water supply container 36, a water supply container 37, and a simple cleaning water container 38 are arranged, and an oral suction tube 38 is installed. In the back of the columnar section 11a, an input/output line 30 or an input/output terminal for inputting or outputting image data is installed. Openings 35A, 36A, 37A, and 38A which are large enough to check the quantities of fluid in the containers are formed in the vicinities of the suction pump container 35, treatment water supply container 36, water supply container 37, and simple cleaning water container 38 on covers 40A and 40B.

Figure 6:
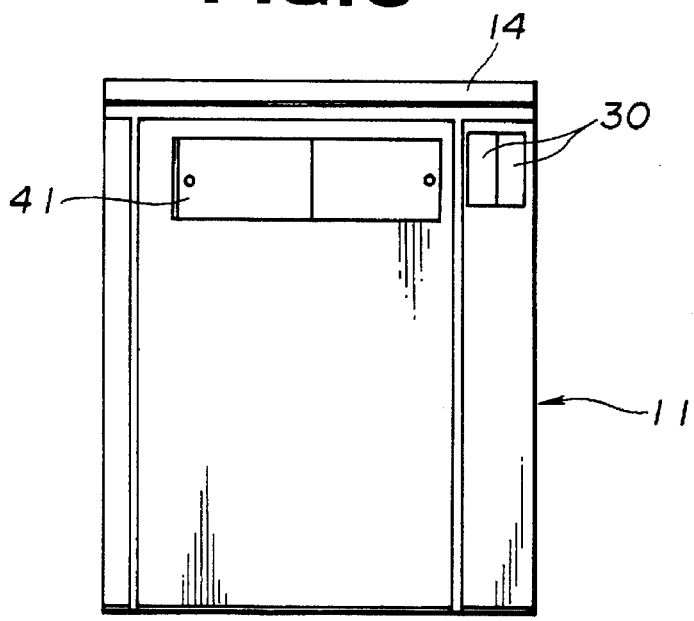
Figure 7:
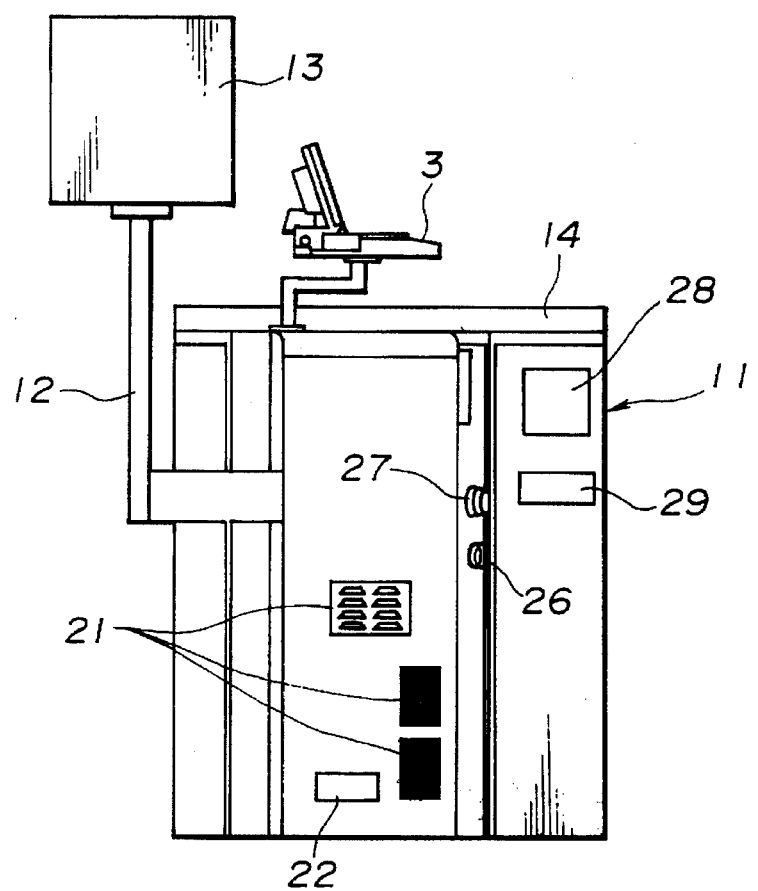

A photography unit 41 is accommodated in the cover of the right side of the control main unit 11 shown in FIG. 6.

Figure 8:
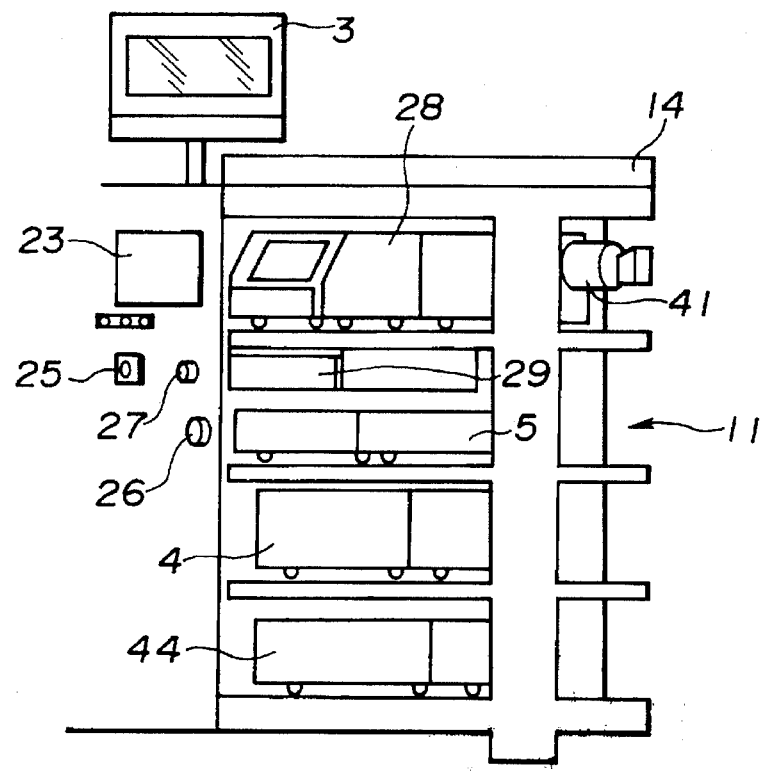

When part of the front cover of the control main unit 11 is removed, as shown in FIG. 8, the electric scalpel 28, TV camera CCU 29, electronic endoscope VSC 5, control computer 4, and light source power unit 44 are seen being accommodated. Under these units, a cooling unit is stored.

As shown in FIG. 9, a laptop computer 3 serving as an operation unit of the endoscope system 1 is arranged on the top of the control main unit 11 to be freely rotatable.

Figure 10:
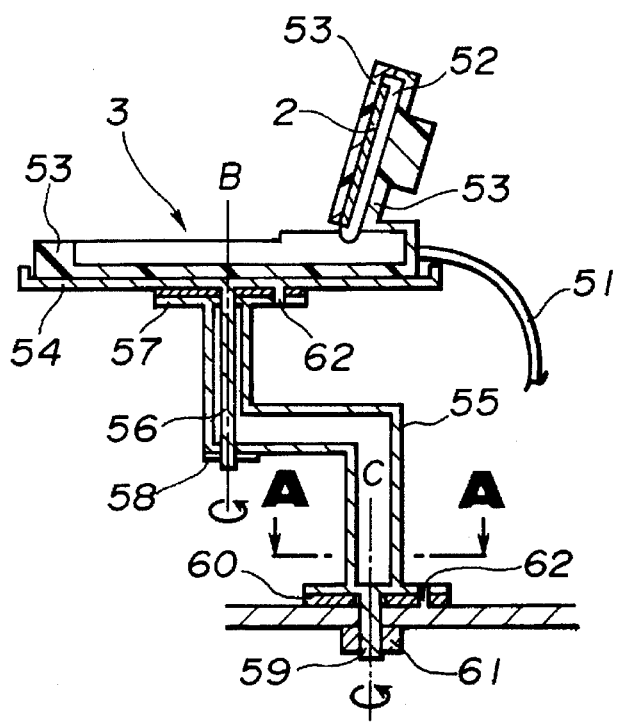

As shown in FIG. 10, the operation computer 3 is, as mentioned previously, provided with a touch panel 2 on the front of the display and connected to the control computer 4 accommodated in the control main unit 11 via a cord 51. The bottom and periphery of the operation computer main unit, and the back and periphery of the display 52 are secured with a plastic cover member 53, so that when the touch panel 2 is pressed, the liquid crystal display 52 will not be turned down. Therefore, the cover member 53 holds the display 52 at an angle at which the display screen can be viewed easily.

The computer 3 is mounted on a table 54. The table 54 is attached to an axis 56 which is freely rotatable relative to a pipe member 55. As shown in FIG. 10, the table 54 is freely rotatable with the axis 56 or a symbol B as a center. 57 denotes a sliding friction plate, and 58, a stopper pin.

The pipe 55 has an L shape. An axis 59 is formed at the proximal end of the pipe 55, which is fitted into the recess on the top of the control main unit 11 via a sliding friction plate 60 and stopped with a nut 61. Thus, the pipe 55 is mounted to be freely rotatable relative to a symbol C. Thus, the table 54 is rotatable with B or C as a center. This allows not only a doctor but also a nurse to rotate the table 54 if necessary and operate the computer 3 smoothly.

Figure 11:
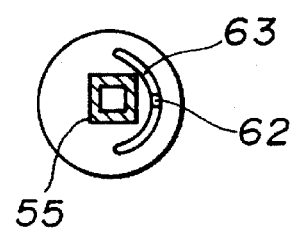

As shown in FIG. 11, a projection 62 is projecting from the top of the control main unit 11. The projection 62 is fitted into a semicircular groove 63 formed on the flange near the proximal end of the pipe member 55. The movement of the axis 59 is restricted, for example, to half of the circumference. This prevents the cord 51 from being tangled. When the axis 59 is allowed to rotate along the full circumference, the cord 51 will be tangled. The axis 56 has the same structure.

As described previously in conjunction with FIG. 1, the operation computer 3 and touch panel 2 are connected to the control computer 4 accommodated in the control main unit 11. The control computer 4 is connected to the electronic endoscope VSC 5 and light source 6. The light source 6 is interchangeable among three modes in which an electronic endoscope is used, a fiberscope is used, and a TV camera is mounted on a fiberscope (the operation can be controlled using the control computer 4).

As shown in FIGS. 3 and 9, the light source connector receptacle 25 is horizontally distanced from the signal connector receptacle 26 so that the light source connector 25 will be diagonally above the signal connector receptacle 26. A light source connector 16b of an endoscope 16 shown in FIG. 9 is connected to the light source connector receptacle 25, and a signal connector 16a at the distal end of a connection cable 16c extending from the light source connector 16b can be connected to the signal connector receptacle 26.

FIG. 12a is an enlarged view showing the positional relationships between the light source receptacle 25 and signal connector receptacle 26. FIGS. 12b and 12c show conventional configurations. In FIG. 12b, a light source 72 and a VSC 73 are installed up and down in a shelf 71. A light source connector receptacle 74 and an electronic endoscope signal connector receptacle 75 are positioned on a vertical line.

In the conventional configurations shown in FIG. 12c, the light source 72 and VSC 73 are stacked up and down. Then, the light source connector receptacle 74 and electronic endoscope signal connector receptacle 75 are positioned on a vertical line.

On the other hand, in this embodiment, the light source connector receptacle 25 and electronic endoscope signal connector receptacle 26 are positioned diagonally. This provides the advantages (effects) below.

Assume that an endoscope is changed. In the conventional configurations, when it is attempted to insert the signal connector 16a into the signal connector receptacle 26, the connection cable 16c extending from the light source connector 16b dangles besides the light source connector receptacle 25. This interrupts insertion of the signal connector 16a of the scope 16 into the signal connector receptacle 26. In this embodiment, even if the connection cable 16c dangles, it will not come near the signal connector receptacle 26. Therefore, connection is not interfered but accomplished smoothly. An operator will not be annoyed with the connection cable 16c during endoscopic manipulation. Furthermore, the cable 16c is hardly stressed. This prevents a signal wire in the cable 16c from disconnecting. In this configuration, a scope can be detached easily with a left hand. Even after the connection cable 16c extending from the scope is removed, it does not dangle in the vicinity. Therefore, when a scope is changed, if the connection cable 16c is removed first, even an S cord or a suction tube can also be detached more easily than in the conventional configurations.

FIG. 13 shows the overall configuration of the first embodiment.

In FIG. 13, the left (except a bed 17) of the dotted line includes components accommodated in or mounted to a control main unit 11, and the right, satellite equipment connected to the control main unit 11.

As described previously, a touch panel 2 consisting of transference electrodes is adhered to a liquid crystal panel of an operation computer 3. The states of switches on the touch panel 2 are read by a control computer 4.

Graphics on the back of the touch panel 2 are changed by the operation computer 3 according to the commands sent from the control computer 4. The control computer 4 transmits the states of all switches in response to a request from the operation computer 3. With power on, the operation computer 3 requests the control computer 4 to send switch states. On the other hand, the control computer 4 incorporates a hard disk to store switch states time-sequentially. Therefore, with power on, the screen on the operation computer 3 shows the states of switches when power was turned off.

The control computer 4 is accommodated in the control main unit 11. The control main unit has a relatively large storage space to accommodate a large personal computer or other computer. On the other hand, in the first embodiment, a laptop computer is employed as the operation computer, because it is space-saving. (Needless to say, not only a laptop computer but also other light-weight computer can be employed.)

Interfaces 8B and 8C are installed on behalf of, for example, the front operation panels of a VSC 5 and a light source 6 respectively, and connected to the control computer 4.

As shown in FIG. 13, the VSC 5 can be connected to peripheral video equipment; such as, a still image recorder 41 (or a still video recorder SVR 41a) accommodated in the control main unit 11, an external VTR 81, and a video printer 82. These peripheral equipment are controlled by the VSC 5 via remote cables. The VSC 5 is controlled by the control computer 4. The control computer 4 controls video equipment indirectly. Thus, the VSC 5 is used to control the peripheral equipment, obviating creation of a new control program.

The video printer 82 fetches a video signal from the still image recorder 41 when the still image recorder 41 is connected, or from the SVR 41a when the SVR 41a is connected.

The control main unit 11 accommodates a TV camera CCU 29 which controls the VTR 81 when a switch 83 is turned on manually.

The light source 6 and VSC 5 are always placed in the same state with power on. Specifically, with power on, the switches are set according to backup data or data stored on hard disk of the control computer 4. When the backup batteries of the VSC 5 and light source 6 are used, if a switch state deviates from that contained in the control computer 4 because of noise, the deviation may remain permanently. This can be prevented by using the backup data contained in the control computer 4.

Figure 14A:
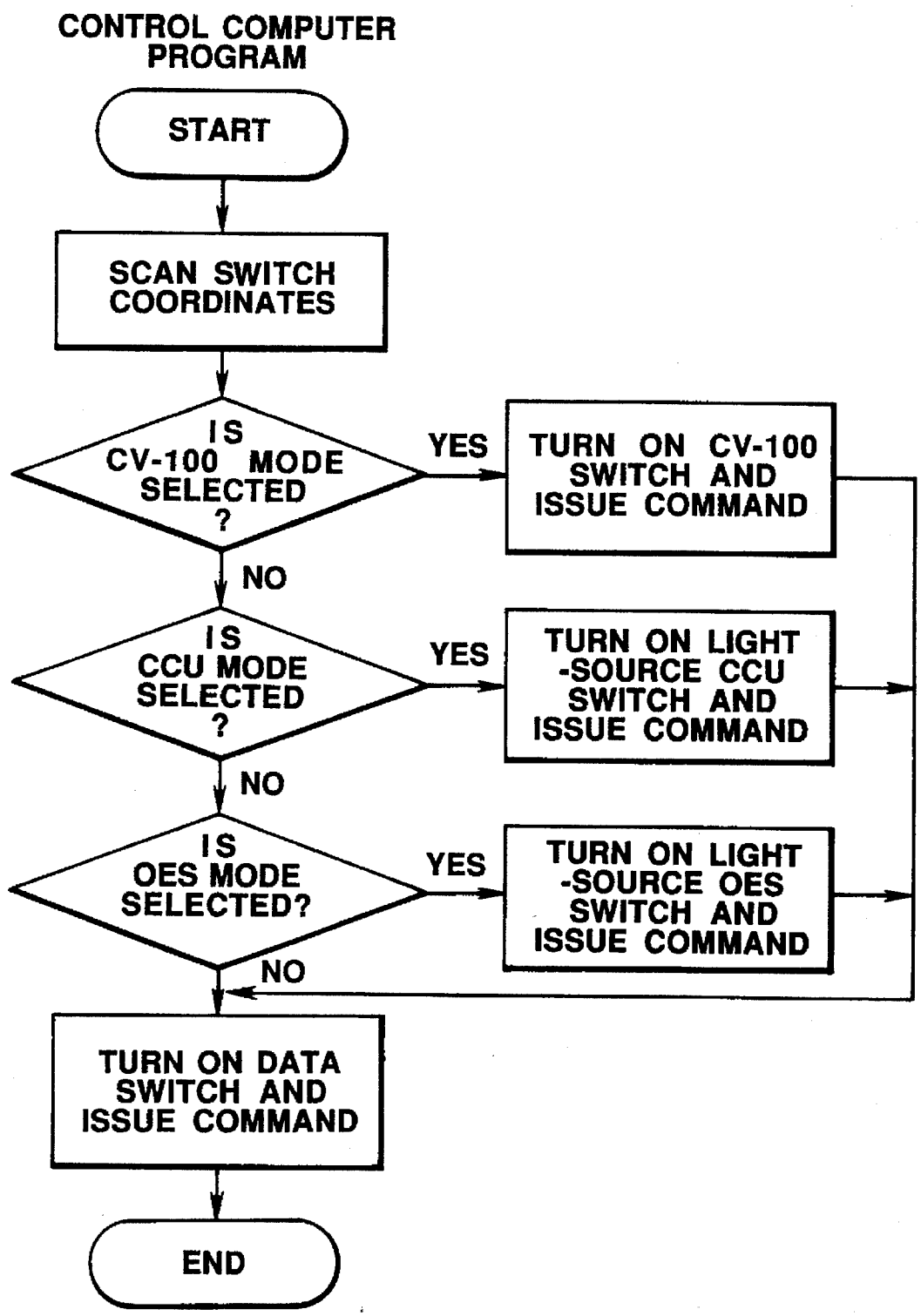

In the first embodiment, the control computer operates according to the flow shown in FIG. 14A, while the operation computer 3, according to the flow shown in FIGS. 14B, 14C, 14D, and 14E.

During the operations shown in FIGS. 14A to 14E, the screen of the operation computer 3 becomes as shown in FIGS. 15A to 15J.

Figure 14B:
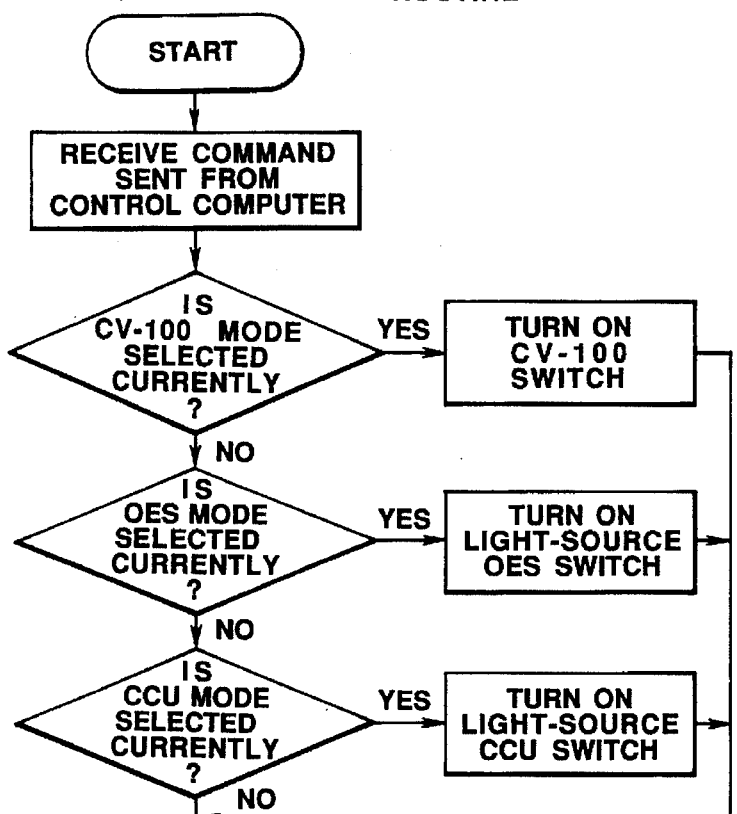
Figure 14C:
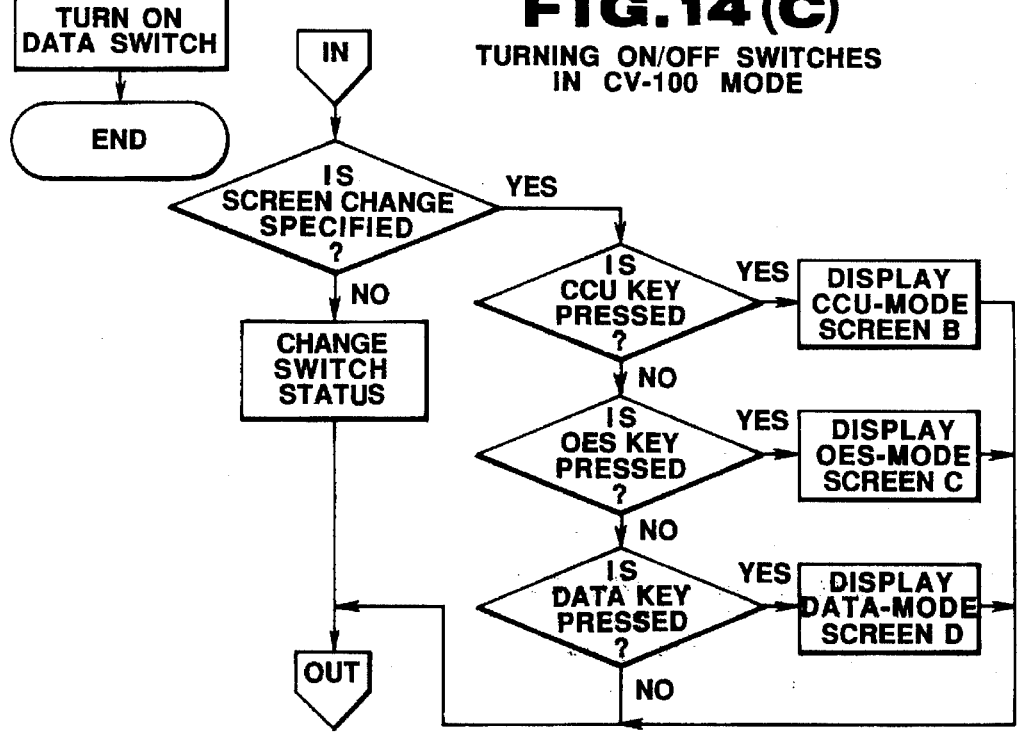
Figure 14F:
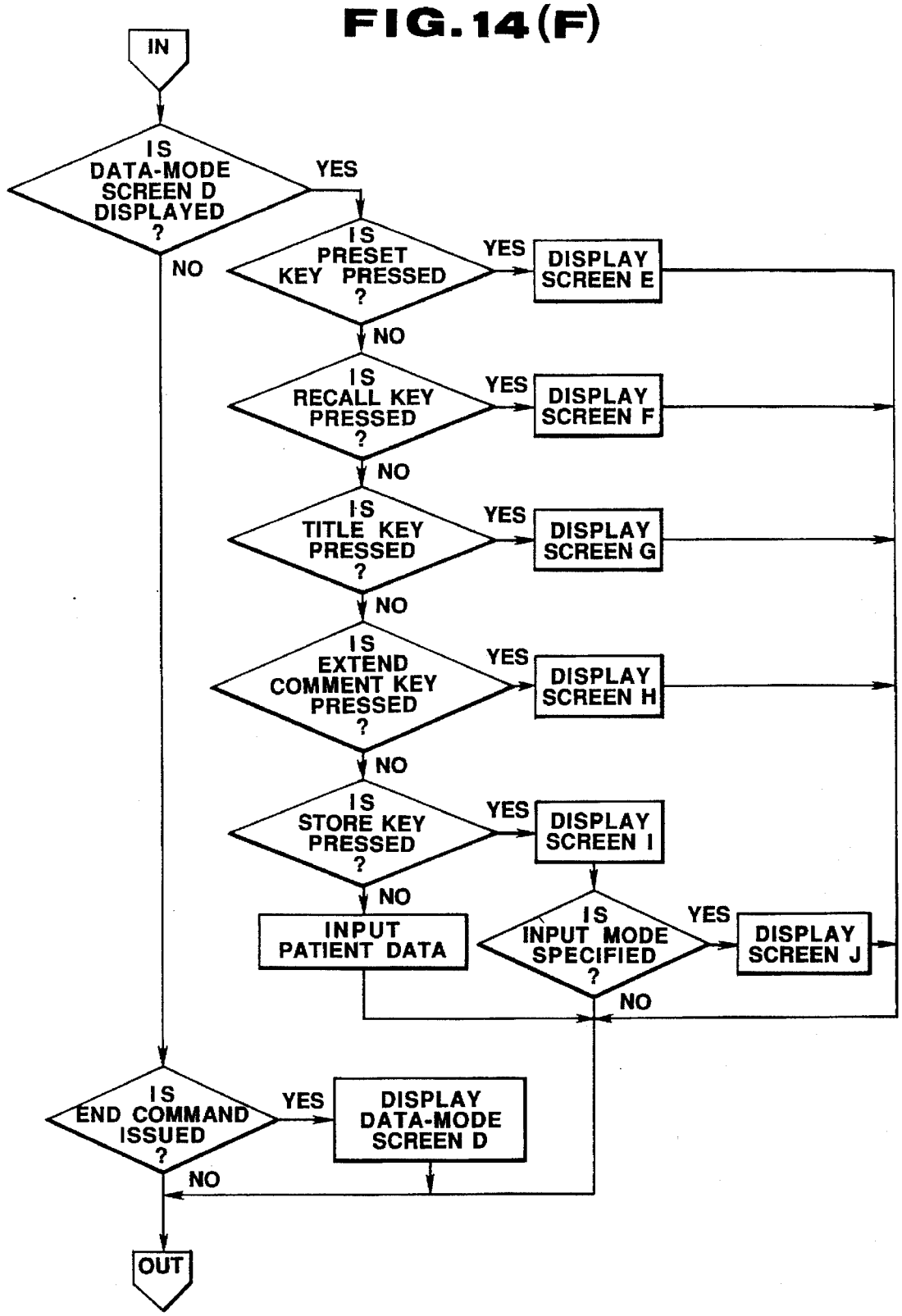
Figure 15:
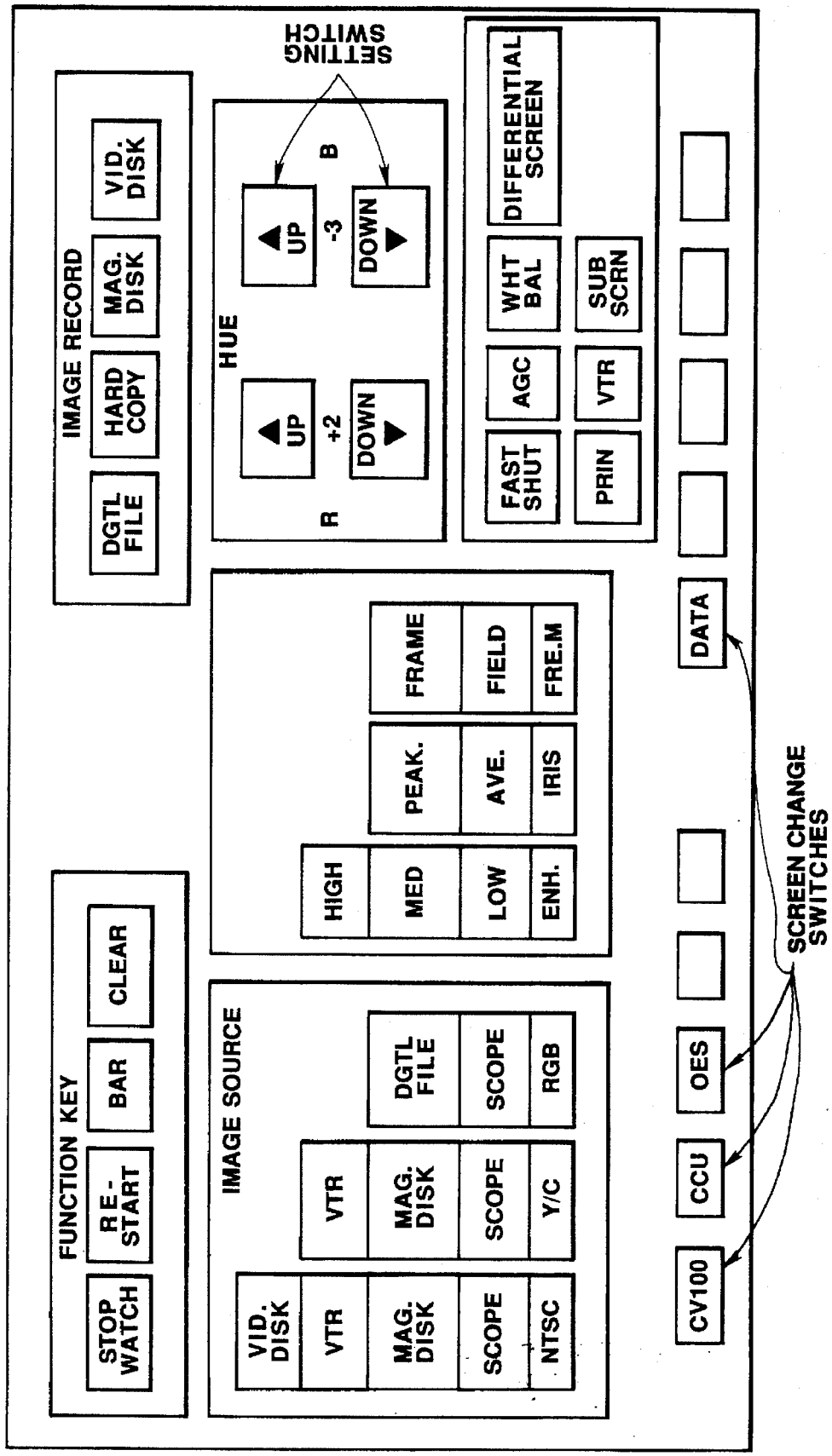

In FIGS. 14 and 15, CV-100 represents an electronic endoscope VSC. The CV-100 mode means a VSC control mode for using an electronic endoscope. The CCU or light source CCU mode is a light source 6 control mode for connecting an electronic endoscope. The OES mode is a light source 6 control mode with a TV camera mounted to a fiberscope (OES).

As shown in FIG. 14A, the control computer 4 scans the switch coordinates of a touch panel 2, then determines in which mode the touch panel 2 is operated; CV-100, CCU, or OES mode. Then, according to the determination, the switches of units are turned on or off. Then, a command is issued.

When neither the CV-100, CCU, nor OES mode is set, it is determined that the data mode is set. Then, the switches of units are turned on or off. Then, a command is issued to the operation computer 3.

FIG. 14B shows the screen change routine.

The operation computer 3 receives a command from the control computer 4, determines a current mode, then turns on the switch of the unit corresponding to the current mode. If the current mode is not the above three modes, the operation computer 3 considers that the data mode is selected, then operates accordingly.

FIGS. 14C, 14D, and 14E shows the processes of turning on or off switches in the CV-100, OES, and CCU modes.

Figure 15B:
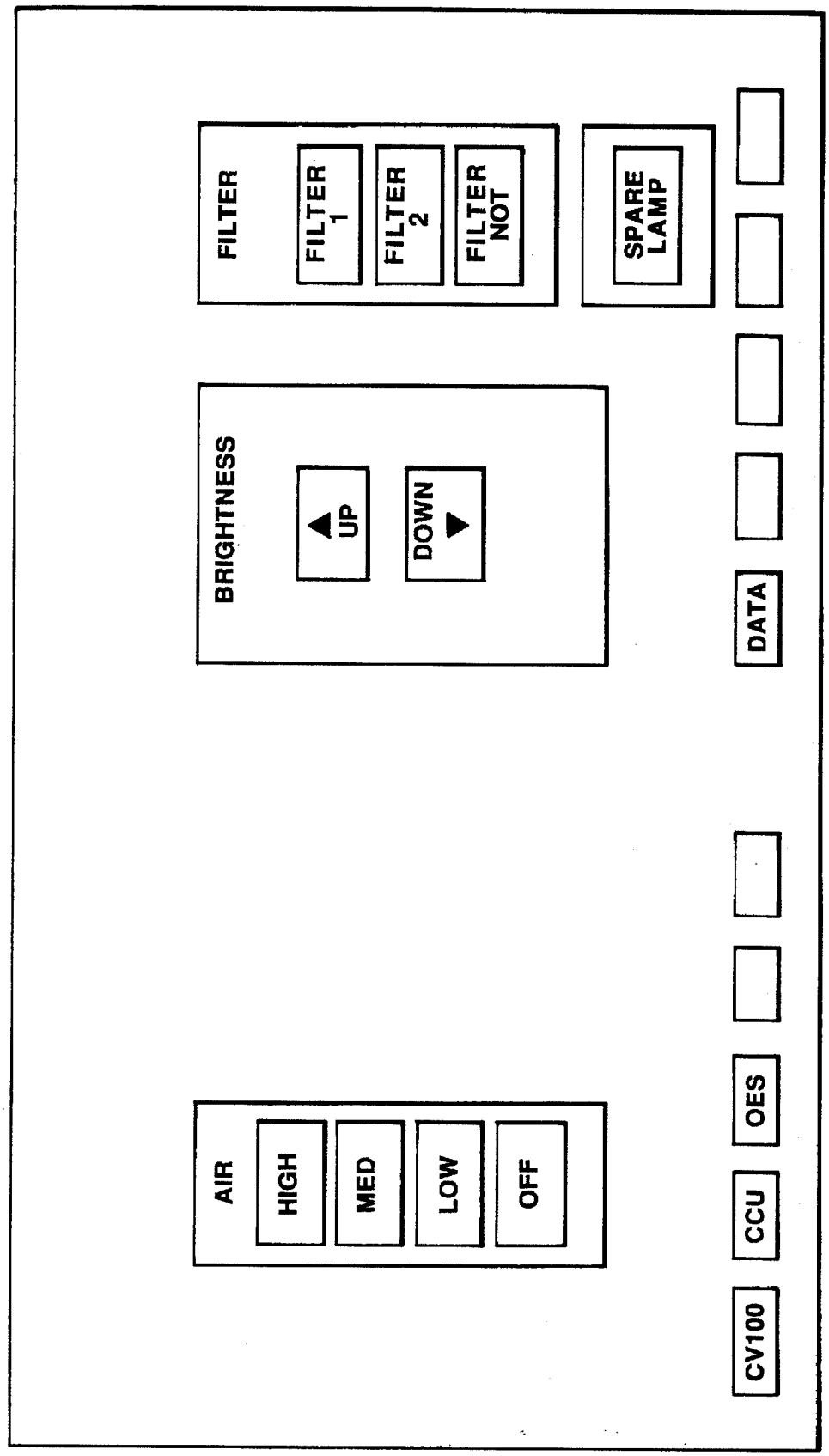
Figure 15:
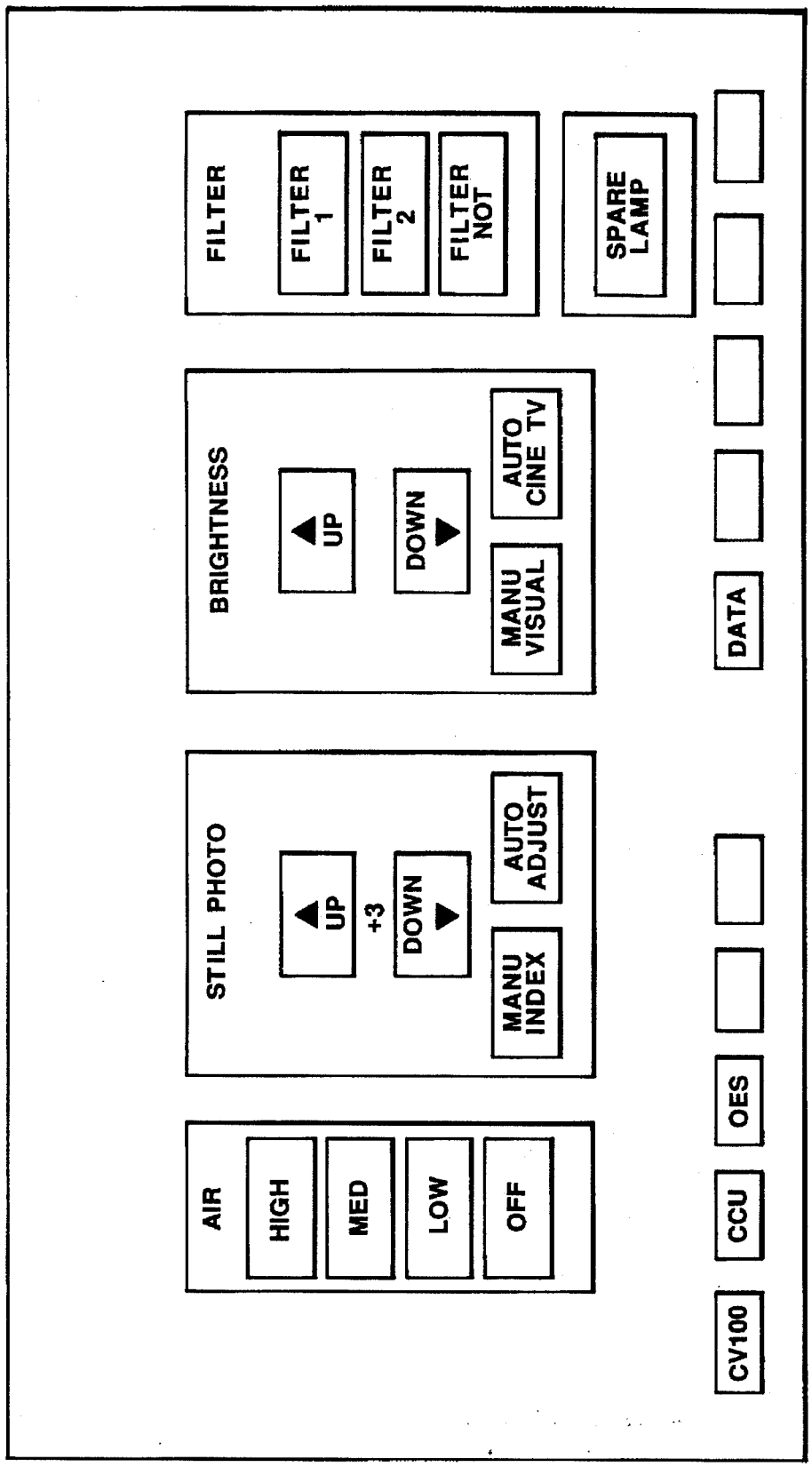
Figure 15E:
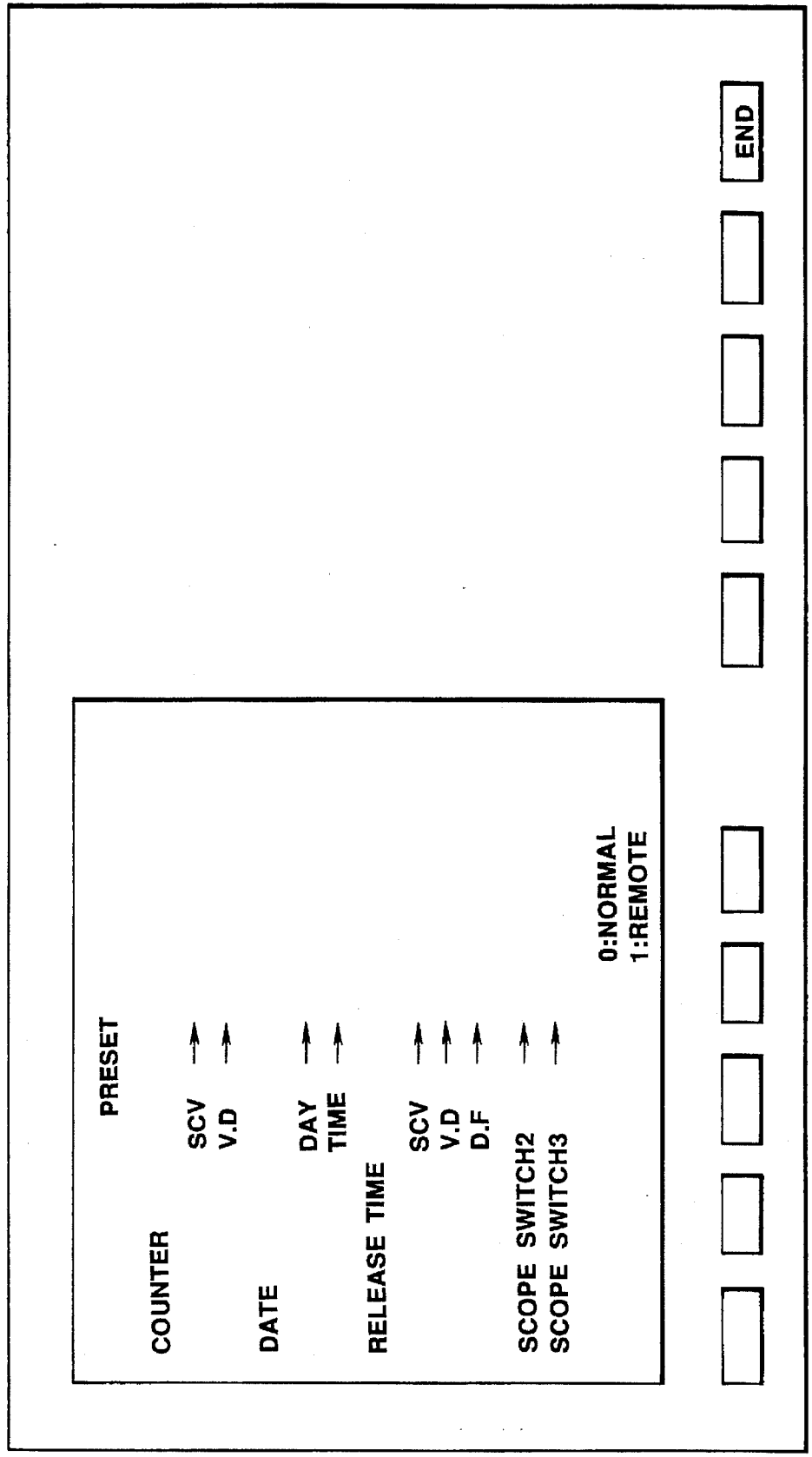
Figure 15G:
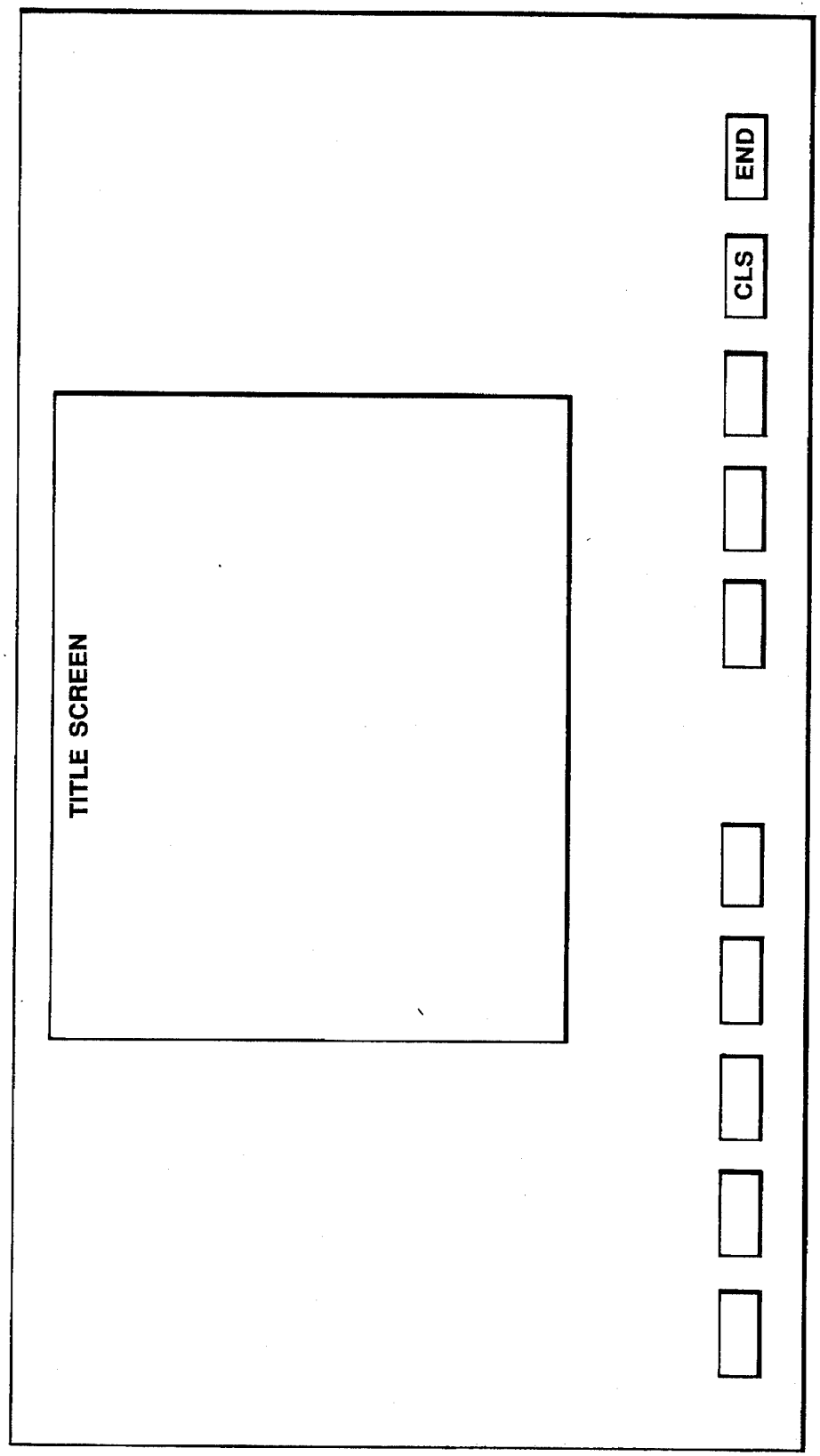
Figure 15H:
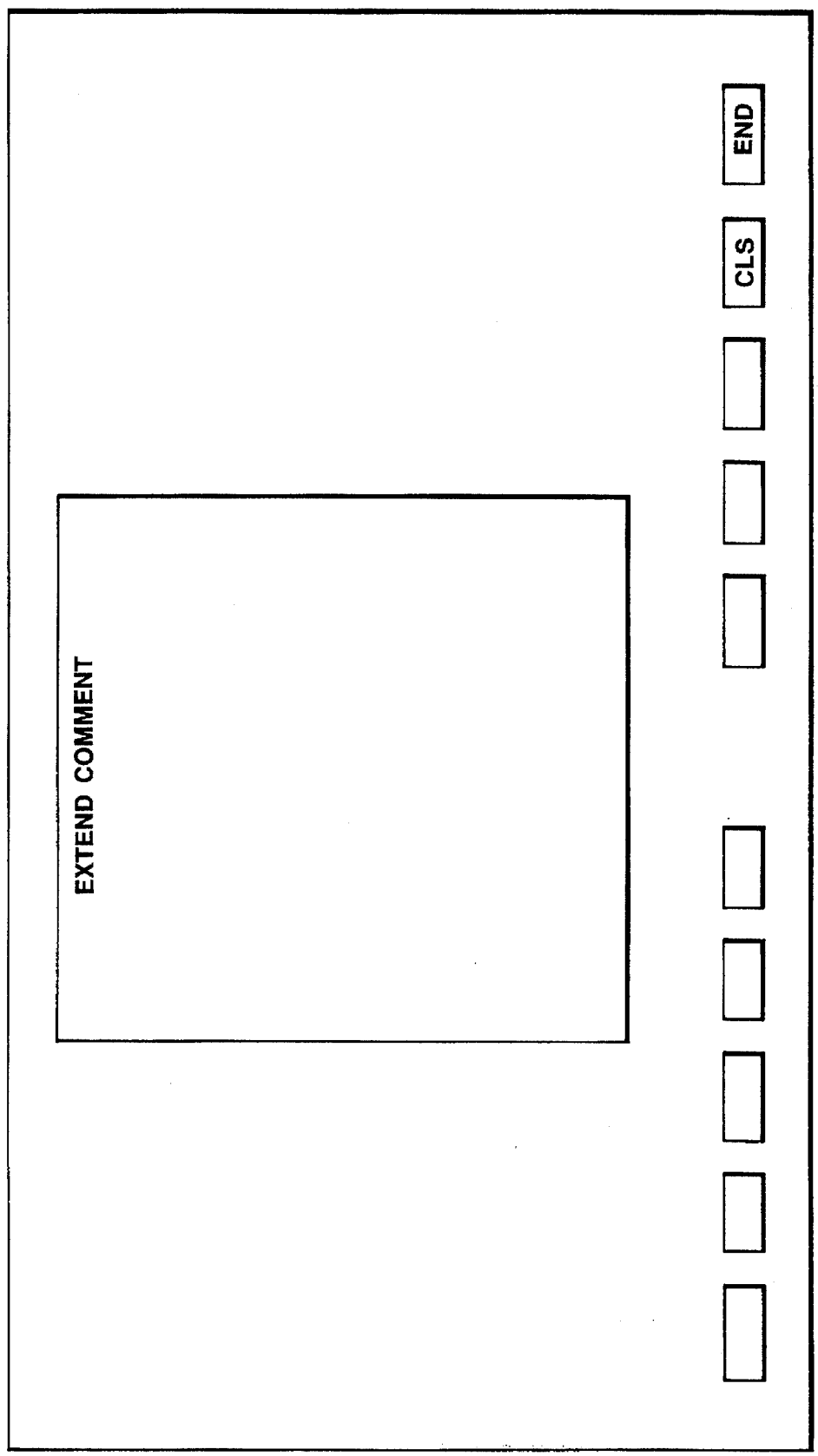

For example, in FIG. 14C, if it is determined that a command entered specifies screen change, it is judged whether the CCU, OES, or data key is pressed. Then, the screen for the determined mode is displayed. Assuming that it is determined that the CCU key is pressed, the screen shown in FIG. 15B is displayed. When it is determined that the OES key is pressed, the screen shown in FIG. 15C appears. When it is determined that the DATA key is pressed, the screen shown in FIG. 15D is displayed.

In FIG. 14C, it is determined that screen change to a mode is not specified, the states of switches are changed in the CV-100 mode. Then, the data-mode processing shown in FIG. 14B is done.

In FIG. 14D, the same processing as the CV-100 mode processing shown in FIG. 14C is performed in the OES mode. As a result, the screen shown in FIGS. 15A, 15B, or 15D is displayed. For example, CV100, CCU, OES, and DATA in the lower part of the screen shown in FIG. 15A are screen change keys (switches). Keys (switches) above these screen change keys are used to operate the CV-100.

FIG. 14E shows the contents of CCU-mode processing. The contents are almost identical to those of CV-100 or OES-mode processing.

Figure 15J:
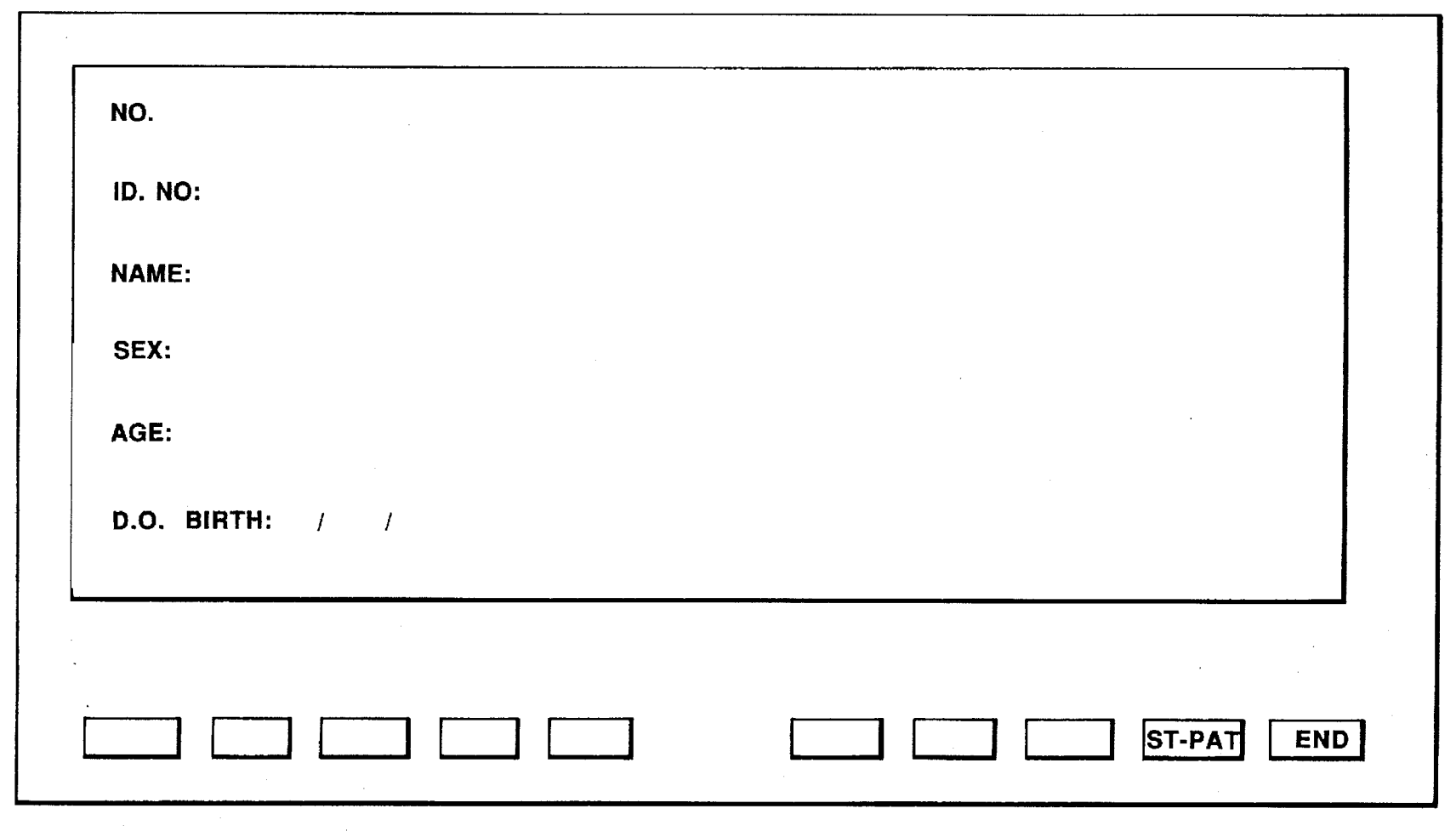

FIG. 14F shows the contents of data-mode processing. When it is determined that the data mode is selected, it is judged which key is pressed; the PRESET, RECALL, TITLE, EXTEND COMMENT, or STORE key. According to the judgment, the screen shown in FIGS. 15E, 15F, 15G, 15H, or 15I is displayed. When the STORE key is pressed, if input is specified, the screen in FIG. 15J is displayed.

On the other hand, if it is determined that neither the PRESENT, RECALL, TITLE, EXTEND COMMENT, nor STORE key is pressed, it is understood that patient data has been entered. Then, the patient data is input.

When power is turned on, the screen previously used is displayed.

In the first embodiment, an electric scalpel 28 and a heat probe (HPU in FIG. 13) 23 are installed beyond the control of the control computer 4. As shown in FIGS. 3 and 5, their operation panels are arranged at positions optimal for a doctor and a nurse to operate them.

The electric scalpel 28 and heat probe 23 are not used so frequently as the VSC 5 or light source 6 during endoscopic examination. Therefore, as shown in FIG. 13, neither the electric scalpel 28 nor heat probe 23 is connected to the control computer 4 and controlled by the control computer 4. Then, their operation panels are arranged at easy-to-operate positions.

The water containers for the heat probe 23, light source 6, and maintenance unit 84 accommodated in the control main unit 11 are backlighted by a backlight 85 so that the levels can be identified at sight through the openings 36A, 37A, and 38A of the cover 40B of the back of the control main unit 11.

The VSC 5 provides the light source 6 with a flash or EE control signal. The light source 6 uses a flash unit 86 to flash light.

A suction pump 87 is used to connect an aspirator tube 39 for aspiration.

To a monitor 13 to be connected to the VSC 5 or CCU 29, a first submonitor 89 and a second submonitor 89' using liquid crystal displays are connected. The submonitors 89 and 89' do not have an output terminal, which, therefore, cannot be cascaded. The submonitors 89 and 89' are connected via a distributor 88.

The VSC 5 can be connected to an image file unit 90 via, for example, an input/output line 30. Thus, image data can be transmitted or received.

The control computer 4, operation computer 3, still image recorder 41, SVR 41a, monitor 13, submonitors 89 and 89', and distributor 88 are isolated from the power supply.

According to the first embodiment, the effects below are available.

Equipment required at least for endoscopic examination including treatment are accommodated or prepared, obviating unnecessary movement. The power supplies are managed as a whole. Video and other signals are managed together with the terminals in a centralized manner.

A tray 14 is placed on a columnar section 11a of a control main unit 11, wherein tools and instruments required for examination can be placed. When the tray 14, which is freely rotatable, is rotated, an endoscope or other instrument necessary for examination can be brought along. This helps minimize a user's moving range.

The display 52 of an operation computer serving as an operation unit incorporates not only a display function but also an operation function. Moreover, since a keyboard 7 is provided, data entry can also be done.

Tubes, an aspirator, water supply containers, a simple cleaning unit, and a cleaning cup are provided and accommodated, enabling a user to clean the system as a whole.

A still image recorder is incorporated. Therefore, recording can also be performed within the system.

When an external image filing system is connected online, a total system can be constructed.

A monitor 13 is mounted on the control main unit 11 so that it can be relocated at a position at which it can be observed optimally.

As mentioned above, according to the first embodiment, almost all the equipment necessary for endoscopic examination are accommodated in or connectable to the control main unit 11. Moreover, a control or operation facility a doctor needs is arranged at a position at which the doctor can operate it smoothly. Equipment a nurse needs for system operation are arranged on the side of the nurse. Equipment used frequently are operated by a centralized operation unit. A centralized control (management) means is provided for centralized control of operations. The centralized operation unit is rotatable so that it can face either a doctor or a nurse for ease of operation. (Only the display 52 of the centralized operation unit may be positioned so that a doctor and a nurse or a primary user or a secondary user can operate it smoothly. Alternatively, the centralized operation unit may be arranged at a position at which the primary and secondary users can operate it smoothly.) Furthermore, since the control main unit has the shape of a deformed square pole, a doctor and a nurse can transfer scopes, treatment adapters, and other accessories easily.

More specifically, according to the first embodiment, only the operation computer 3 is required to operate components of an endoscope system which must be operated during main endoscopic examination (including treatment using a treatment adapter). This provides a lot of advantages described previously and greatly improves the system operability for endoscopic examination.

A computer is used to control the operation display and peripheral equipment. This allows a user to actuate a plurality of different equipment using a single switch or operate the equipment in harmony. Furthermore, since the graphics of screens on the computer are combined with the touch panel to form the centralized operation unit, the arrangement of switches can be modified according to a combination of units or the screens can be changed according to the units to be controlled. Thus, the centralized operation unit can be constructed flexibly depending on system configuration.

When the appearance is concerned, no part is projecting. This allows a doctor and a nurse to move smoothly.

Such problems of conventional systems that cables connecting peripheral equipment are laid on the floor to cripple smooth operation and that it is very inconvenient to operate decentralized equipment, and other numerous problems have been solved.

In the configuration of FIG. 13, the VTR 81 and video printer 82 are satellite equipment of the control main unit 11. That is to say, the control main unit 11 plays a role of a terminal for recording endoscopic image data during endoscopic examination. An image file unit 90 plays the same role.

On the other hand, when a filing system including the image file unit 90 is connected to a plurality of endoscopic systems 1A, 1B, 1C, etc. over a bidirectional communication line 92, a composite endoscope system 93, in which endoscopic systems 1I (I=A, B, C, etc.) act as terminals, and the filing system 91, as a centralized control center, can be constructed.

In the foregoing configuration, the filing system 91 centralizes management of image data and patient data sent from endoscope systems 1I. The endoscope systems 1I send or retrieve image data to or from the filing system 91. For example, data concerning a patient who underwent endoscopic examination using other endoscope system 1I can be retrieved easily. Cases similar to a certain case can be retrieved, which will be helpful for examination or treatment. This kind of system can be constructed easily because endoscope systems 1I are controlled and managed by the control computer 4 or a system control.

In FIG. 13, the CCU 29 can be connected to the VSC 5 in the same manner as the control computer 4 is connected to the VSC 5.

Furthermore, a mouse can be employed on behalf of the touch panel 2. Alternatively, tile mouse and touch panel 2 may be used in combination.

Figure 17:
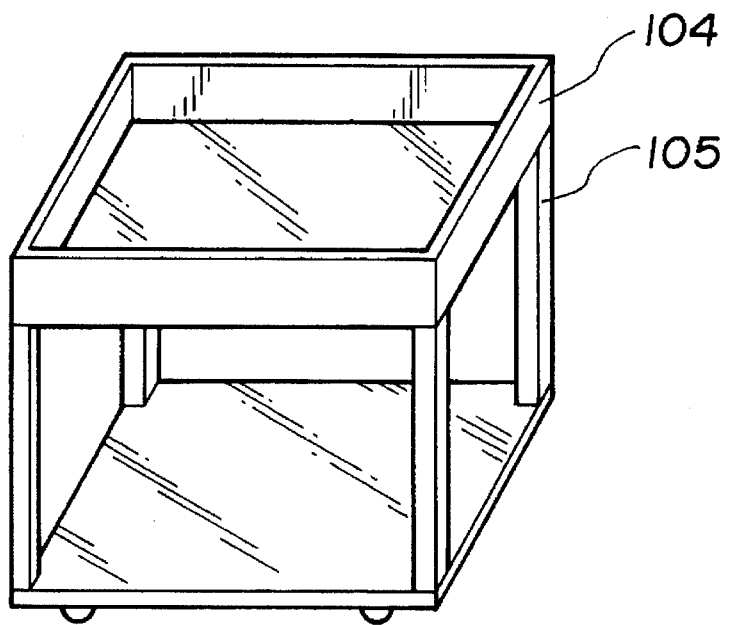
FIG. 17 is an oblique view of a conventional cart and base.
Figure 18:
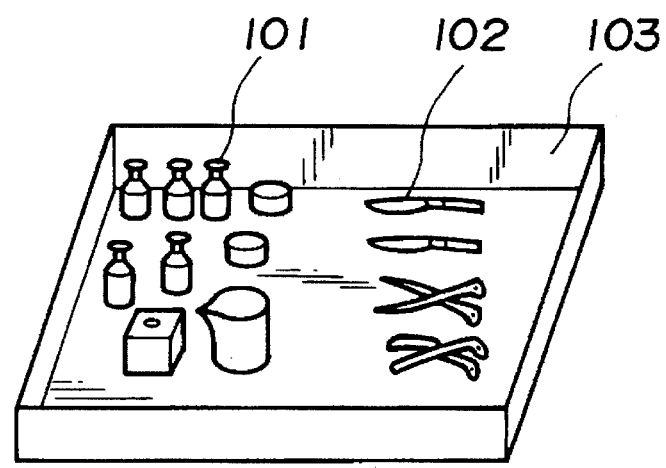
FIG. 18 is an oblique view of a conventional tray.

When a conventional endoscope is used for examination or treatment, the associated chemicals 101 and instruments 102 are placed in a tray 103 as shown in FIG. 18. The tray 103 is fixed to a base 104 or a cart 105 as shown in FIG. 17.

Therefore, a doctor or a nurse located around the cart cannot easily pick up chemicals and instruments placed at positions at which the doctor or nurse has difficulties in picking them up.

Three examples of the tray loading chemicals and instruments are explained below, wherein the tray is freely rotatable so that a doctor and a nurse can pick up objects from a distance.

FIGS. 19 and 21 show the first example of an endoscopic tray.

In the first example, as shown in FIG. 19, a rotatable base 104 is installed on the top of a table 105 and a tray 103a can be fixed to the base 104. Alternatively, as shown in FIG. 20, a rotatable base 104 is installed on the top of a cart 106 and a tray 103b is fixed to the base 104.

Since the rotatable base 104 is installed and the tray 103a or 103b is mounted on the base 104, when the base 104 and tray 103a or 103b are rotated, chemicals 101 and instruments 102 placed on the opposite side of a user can be brought along. Therefore, a doctor or a nurse can pick up chemicals 101 and instruments 102 from the tray 103a or 103b without stretching his or her arm during endoscopic surgery.

When a tray having two or more partitioned areas like the trays 103a and 103b shown in FIGS. 19 and 20 is used, chemicals 101 and instruments 102 can be kept neatly.

FIG. 21 shows an example of the rotation mechanism of the base 104. In this example, rotatable balls 107 are placed at given positions on the top of the table 105 or cart 106. The base 104 whose axis is supported by the table 105 or cart 106 to be freely rotatable is placed on the balls 107. This makes the base 104 rotatable.

Figure 22:
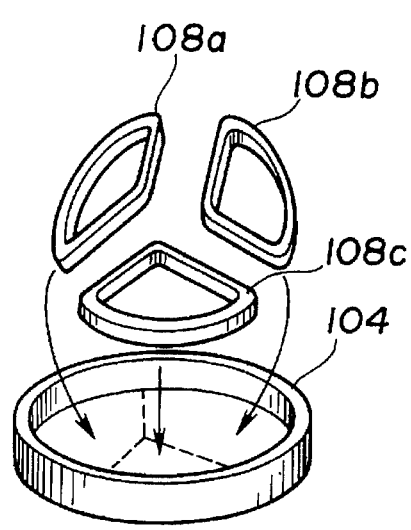
FIGS. 22 to 24 relate to the second example of an endoscopic tray.
Figure 23:
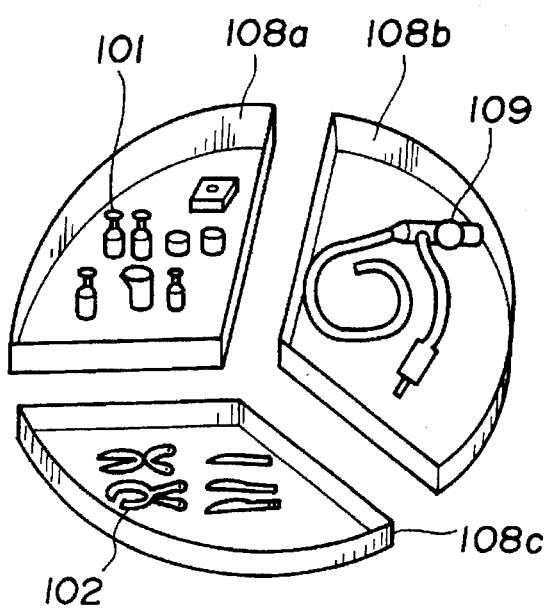
Figure 24:
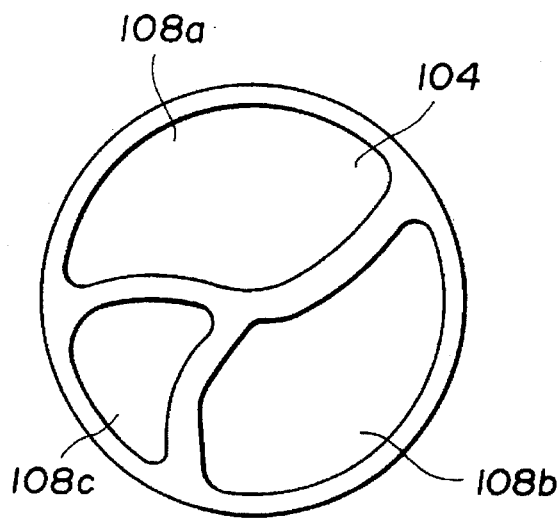

FIGS. 22 to 24 show the second example of an endoscopic tray.

In this example, a tray having two or more partitioned areas described in the first example is separated area by area. As shown in FIG. 22, trays 108a, 108b, and 108c can be placed on a base 104. Chemicals 101, instruments 102, and a scope 109 are placed in the trays 108a to 108c. Thereby, when the scope 109 is replaced, if other scope is placed on other tray in advance, the scopes can be switched together with the trays. This obviates sterilization of a tray during surgery. Thus, scopes can be changed easily.

As shown in FIG. 24, the separated trays 108a to 108c may have different shapes. Thereby, when a tray is replaced with a new one, the new tray will never be placed at an incorrect position. Thus, trays can be changed easily. Or, the trays 108a to 108c may be painted with different colors, and the top of the base 104 may be painted with the same colors as those of the trays. Or, grooves or projections may be formed on the top of the base 104 so that the trays can be engaged with the grooves or projections.

Other components, functions, and effects are identical to those of the first example.

Figure 25:
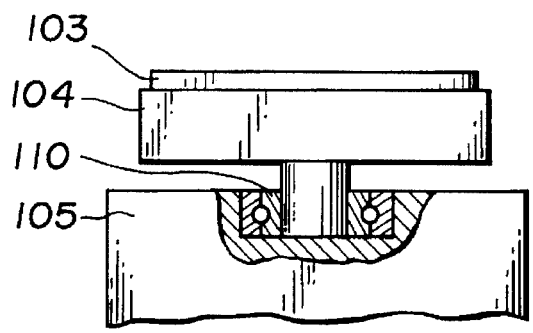
FIG. 25 shows a partly notched cross section of the rotation mechanism of a base in the third example of an endoscopic tray.

FIG. 25 is a partly notched lateral view of the rotation mechanism of a base in the third example.

In this example, ball bearings 110 installed on the table 105 are used instead of the balls 107 supporting the base 104 to hold the axis of the base 104. This makes the base 104 rotatable.

Other components, functions, and effects are identical to those in the first example.

Figure 26:
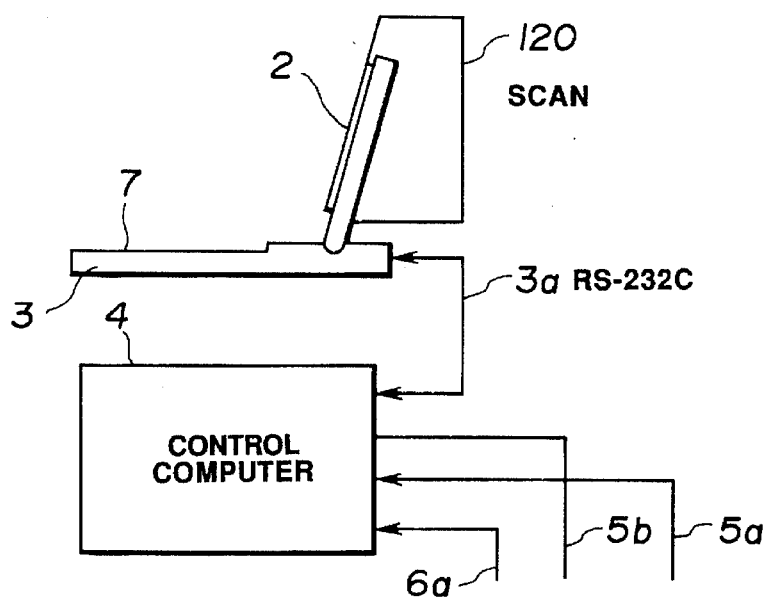
FIG. 26 is a configuration diagram showing the main section of the second embodiment of the present invention.

FIG. 26 shows the main section of the second embodiment of the present invention.

In this embodiment, the relationships between a control computer 4, and controlled equipment including a VSC 5 and a light source 6 are identical to those in the first embodiment.

On the other hand, a touch panel 2 is scanned by an operation computer 3 via a cable 120. As a result, the operation computer 3 changes its own control screens and sends switch information as commands to the control computer 4 via a cable 3a. This is a difference from the first embodiment.

The control computer 4 controls the VSC 5 and light source 6 based on a command transmitted.

In the first embodiment, the control computer 4 scans the touch panel 2 and the operation computer 3 displays screens. The operation of the control computer 4 may deviate from that of the operation computer 3. To prevent the deviation, a deviation-prevention command must be issued. This makes the command procedure excessively complex. According to the second embodiment, the deviation-prevention command becomes unnecessary (because the operation modes never deviate each other). Therefore, the command procedure becomes clear-cut and simple.

In the second embodiment, when the power supply of the operation computer 3 is turned off, no operation can be made. In the first embodiment, even when no control screen appears, if the area corresponding to a certain switch is pressed, the associated operation is done. This is other difference between the first and second embodiments.

Figure 27:
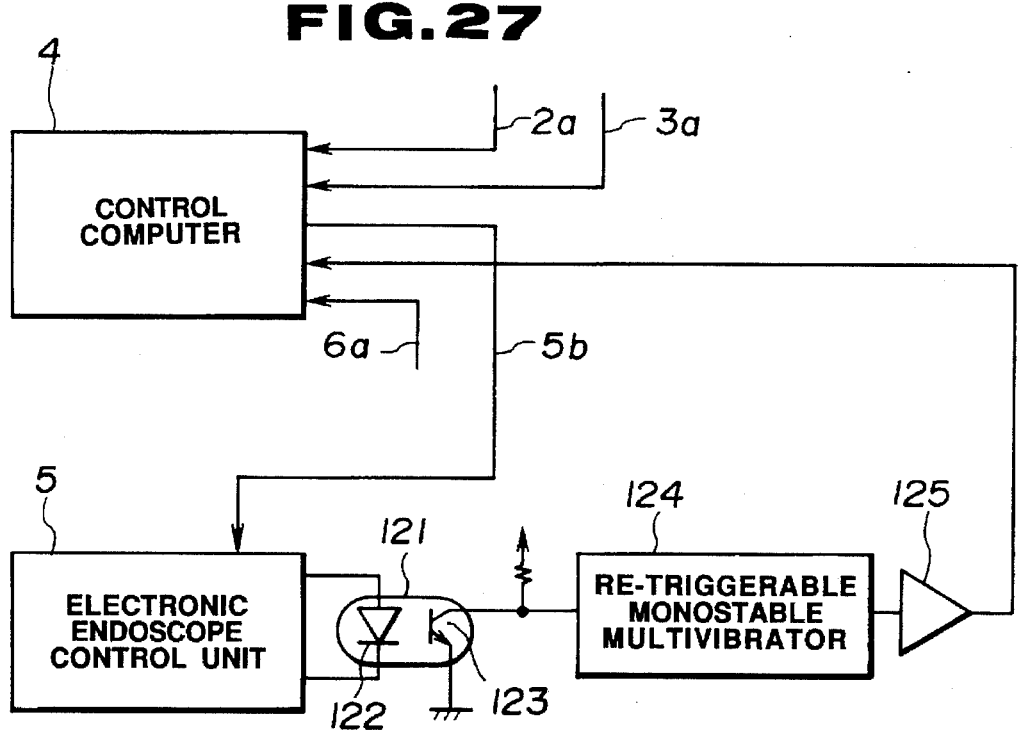
FIG. 27 is a configuration diagram showing the main section of the third embodiment of the present invention.

FIG. 27 shows the configuration of the main section of the third embodiment of the present invention.

In this embodiment, the relationships among a control computer 4, an operation computer 3, and a touch panel 2 are identical to those in the first embodiment. The control computer 4 controls a VSC 5 and a light source 6 in the same manner as that of the first embodiment. In the first embodiment assuming that the control computer 4 controls the operation of the VSC 5, the control computer 4 uses software to execute a program for checking how the VSC 5 operates in reality, then transmits the result to the operation computer 3 with a command.

On the other hand, in the third embodiment, an LED 122 forming a photocoupler 121 blinks on behalf of the LED of the VSC 5. The blink is detected by a phototransistor 123. The output of the phototransistor 123 actuates a monostable multivibrator which can be re-triggered. The output of the monostable multivibrator is provided to a buffer 125. Then, the high or low level of the output of the buffer 125 is read by the control computer 4. (Herein, the LED 122 is lit dynamically.)

That is to say, a program is not executed to read the operation state of the VSC 5 but hardware is used. Thus, the program becomes unnecessary.

When the LED 122 is not lit dynamically, the monostable multivibrator 124 becomes unnecessary.

The first and third embodiments may be combined.

The third embodiment is effective, for example, for an iris switch (for light adjustment between the peek and average levels) on the operation unit of an electronic endoscope for controlling the VSC 5 directly, an indicator for a high-speed shutter, a white balance indicator, or other mechanism whose lighting is determined by an internal state which is not displayed on the VSC 5 panel.

The LAMP indicator (indicating an emergency lamp) on the light source 6 is unrelated with the control computer 4. This kind of indication cannot be identified merely by checking the operation of the control computer 4 and the state of the operation panel. For a state which cannot be controlled directly at the operation panel, in particular, the third embodiment is effective.

Figure 28:
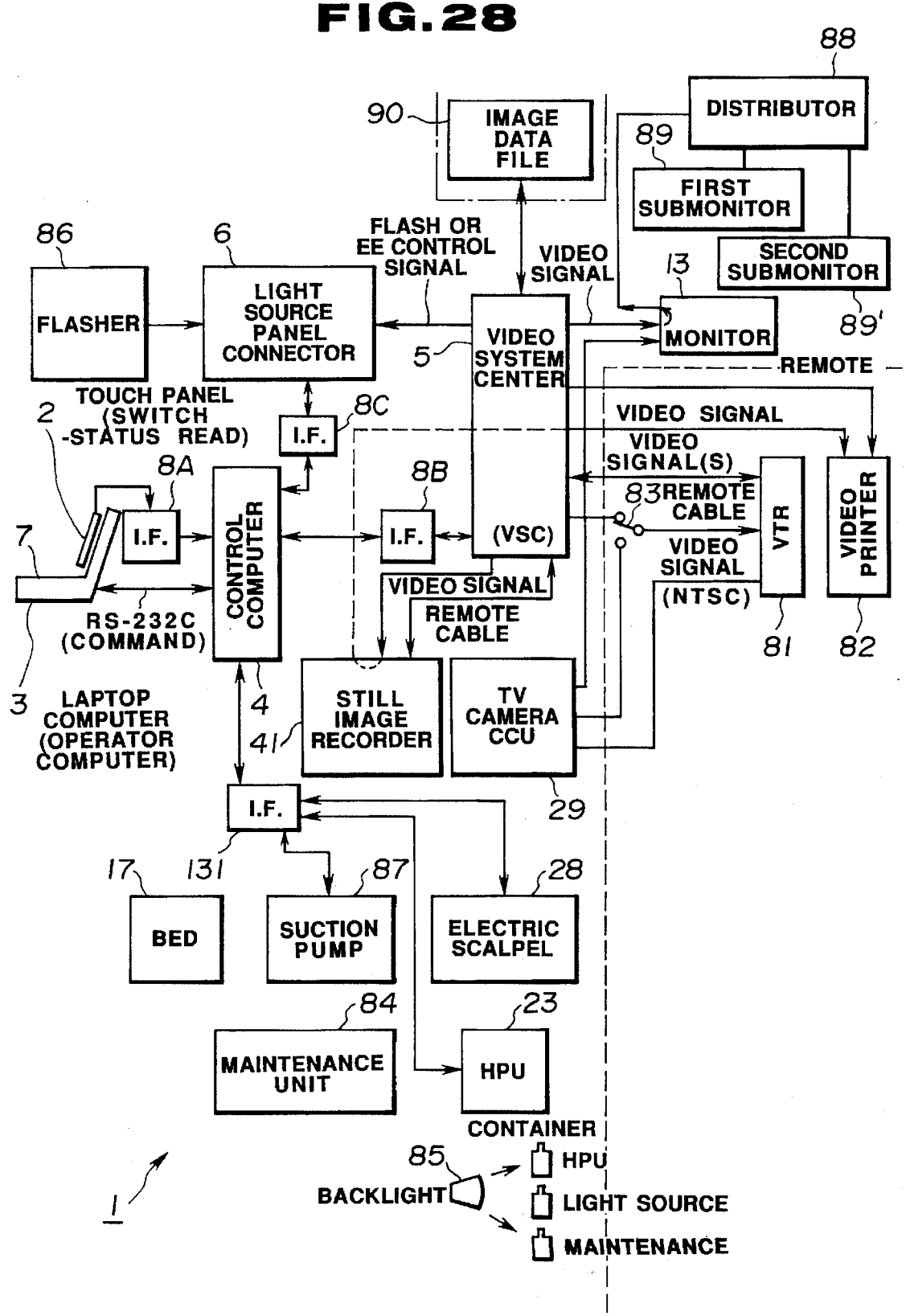
FIG. 28 is a configuration diagram showing the overall configuration of the system according to the fourth embodiment of the present invention.

FIG. 28 is a configuration diagram showing an entire system according to the fourth embodiment of the present invention.

In the first embodiment, an electric scalpel 28 and a heat probe 23 are installed beyond the control of a control computer 4. That is to say, the electric scalpel 28 and heat probe 23 can be provided with multiple operation panels so that they can be operated easily at multiple places. The control of the electric scalpel 28 and heat probe 23 is not centralized at the control computer 4.

On the other hand, in the fourth embodiment, the electric scalpel 28, heat probe 23, and suction pump 87 are connected to the control computer 4 via an interface 131. Other components are installed in the same manner as those in the first embodiment.

Thus, the electric scalpel 28, heat probe 23, and suction pump 87 are connected to the control computer 4 and dealt with in the same way as a light source 6 or a VSC 5, so that they can be operated at a touch panel 2 or an operation computer 3. Based on this operation, the control computer 4 controls the operations of units.

Figure 29:
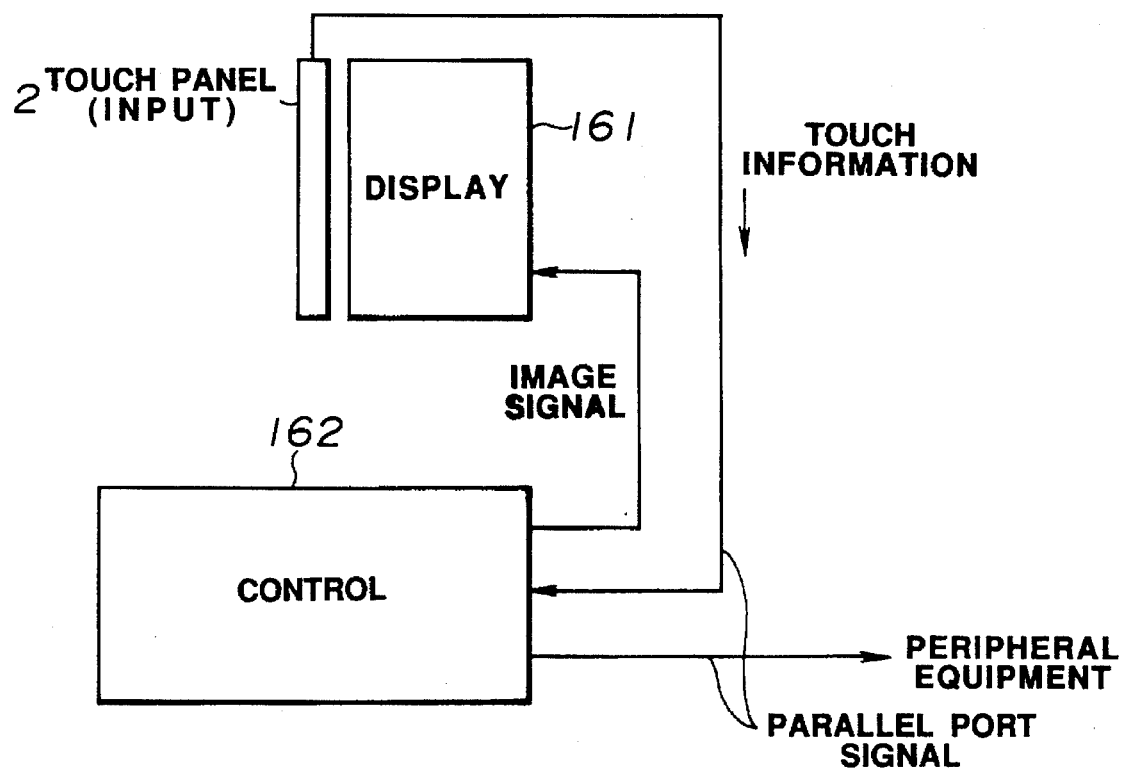
FIG. 29 is a block diagram showing the configuration of the main section of the fifth embodiment of the present invention.

FIG. 29 is a block diagram showing the configuration of the main section according to the fifth embodiment of the present invention.

In the fifth embodiment, a centralized operation unit does not incorporate an independent computer but consists of a display 161 and a touch panel 2. A control 162 is used for every control. The control 162 for controlling peripheral equipment and the centralized operation unit is connected to the touch panel 2 or an input unit, the display for centralized operation screens, a light source, and other peripheral equipment.

In the embodiment, the control 162 transmits an image signal for an initial screen to the display 161. The display 161 displays an initial screen according to the image signal. Then, when a given area of a screen on the touch panel 2 is pressed, touch information is input to the control 162. Then, it is detected that an input is provided. Next, the control 162 places the information of the next screen on the image signal. The display 161 changes the screen to display the operation screen accordingly. Then, the control 162 reads the touch information sent from the touch panel 2. If the information is a command instructing to control peripheral equipment, the control 162 generates control signals, transmits the control signals to the peripheral equipment, and thus controls the peripheral equipment.

Thus, in the fifth embodiment, commands concerning screen display are not issued through communication between two computers. This does not cause an overhead time derived from communication for screen change. Therefore, screen change can be done quickly. The control 162 not only centralizes control of peripheral equipment but also controls screen display of the operation display 161 as a whole. This realizes a compact display and a simple system configuration.

Figure 30:
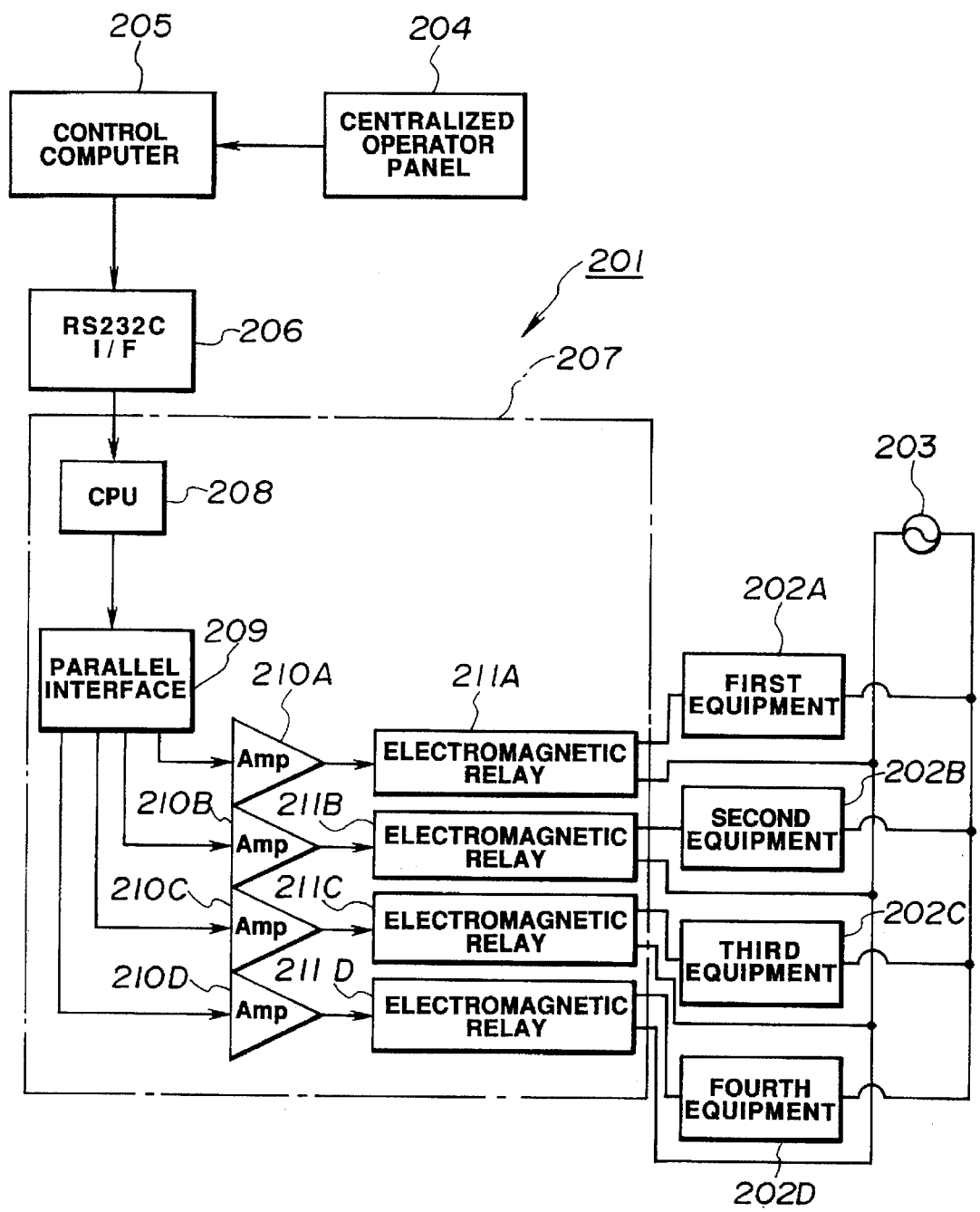
FIGS. 30 and 31 relate to the sixth embodiment of the present invention.
Figure 31:
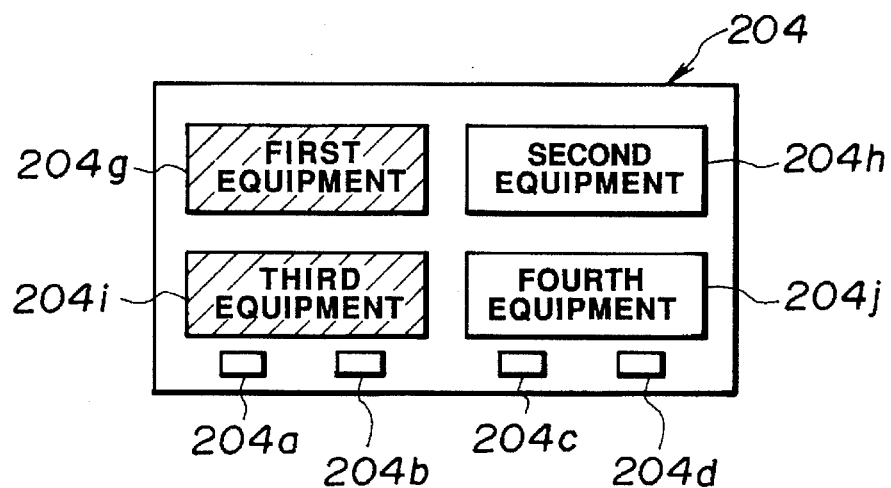

FIGS. 30 and 31 relate to the sixth embodiment of the present invention. FIG. 30 schematizes an overall configuration of an endoscope system. FIG. 31 is a front view of a centralized operation panel of the system shown in FIG. 30.

An endoscope system 201 shown in FIG. 30 includes four peripheral equipment 202A, 202B, 202C, and 202D (hereafter, they may be represented as peripheral equipment 202) and controls the on and off operations of the power supplies of the four units. The number of peripheral equipment 202 is not limited to four. Any number of peripheral equipment can be installed according to the purpose of use.

The endoscope system 201 comprises a power supply 203 for supplying, for example, 100 VAC to the peripheral equipment 202A, 202B, 202C, and 202D, a centralized operation panel 204 or a centralized operation means which centralizes control of the on and off operations of the power supply 203 for supplying power to the peripheral equipment 202A, 202B, 202C, and 202D and is installed to be handy for a user, a control computer 205 which receives the on or off information from the centralized operation panel and outputs an on or off command signal, an interface port; such as, an RS-232C serial interface for converting the on or off command signal provided by the control computer 205 into a serial signal and a power switching unit 207 for turning on or off power for the peripheral equipment 202A, 202B, 202C, and 202D.

The power switching unit 207 comprises a CPU 208 for processing a serial command signal the serial interface 206 outputs, a parallel interface port 209 for outputting four command signals provided by the CPU 208 in parallel, amplifiers 210A, 210B, 210C, and 210D (hereafter, they may be represented as amplifiers 210) for amplifying four parallel signals the parallel interface 209 outputs, and electromagnetic relays 211A, 211B, 211C, and 211D (hereafter, they may be represented as electromagnetic relays 211) for turning on or off the contacts according to the four output signals of the amplifier 210.

The peripheral equipment 202 includes an endoscopic light source for supplying power to, for example, a fiberscope which is not illustrated, an automatic imaging unit for forming optical images observed with the fiberscope, a cautery hemostasis unit which is used trans-endoscopically to stop bleeding from a lesion, or a cautery power unit for the cautery hemostasis unit. The numbers and types of units vary depending on the purpose of use or endoscope employed (for example, an electronic endoscope). The numbers of amplifiers 210 and electromagnetic relays 211 are increased according to the number of the peripheral equipment 202.

As shown in FIG. 31, the centralized operation panel 204 comprises switches 204a, 204b, 204c, and 204d for turning on or off the peripheral equipment 202A, 202B, 202C, and 202D, and indicators 204g, 204h, 204i, and 204j for indicating the on or off states of the peripheral equipment 202A, 202B, 202C, and 202D according to the states of the switches 204a, 204b, 204c, and 204d. The centralized operation panel 204 may comprise well-known touch panel switches formed on the monitor. A general-purpose keyboard or monitor may be employed on behalf of the switches or indicators.

In the foregoing configuration, when, for example, the switches 204a and 204c on the centralized operation panel 204 are turned on, the "on" command signal is output to the amplifiers 210A and 210C via the control computer 205, serial interface 206, CPU 298, and parallel interface 209, then the contacts of electromagnetic relays 211A and 211B are turned on. Then, the peripheral equipment 202A and 202C are provided with 100 VAC from the power supply 203 and placed in "on" state. The indicators 204g and 204i on the centralized operation panel 204 light (shaded areas in FIG. 31) to indicate that the peripheral equipment 202A and 202C are on.

In this embodiment, the centralized operation panel 204 is installed as part of (or separately from) the endoscope system 201 located near a user position for operating an endoscope. Therefore, the peripheral equipment 202 need not be turned on or off one by one. The on or off operations of equipment can be centralized with ease. Users are relieved from a nuisance of turning on or off equipment one by one. Equipment can be turned off quickly. This prevents such a careless mistake that an unused unit is held on to waste power.

FIGS. 32 to 38 show the seventh embodiment of the present invention.

Figure 32:
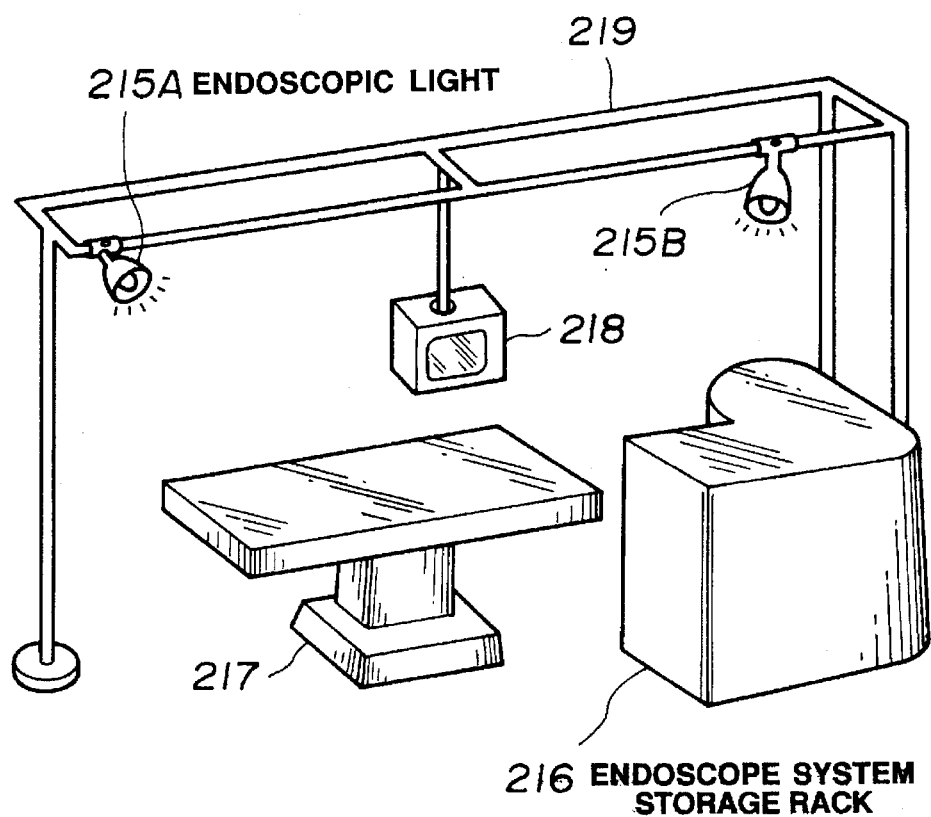
Figure 33:
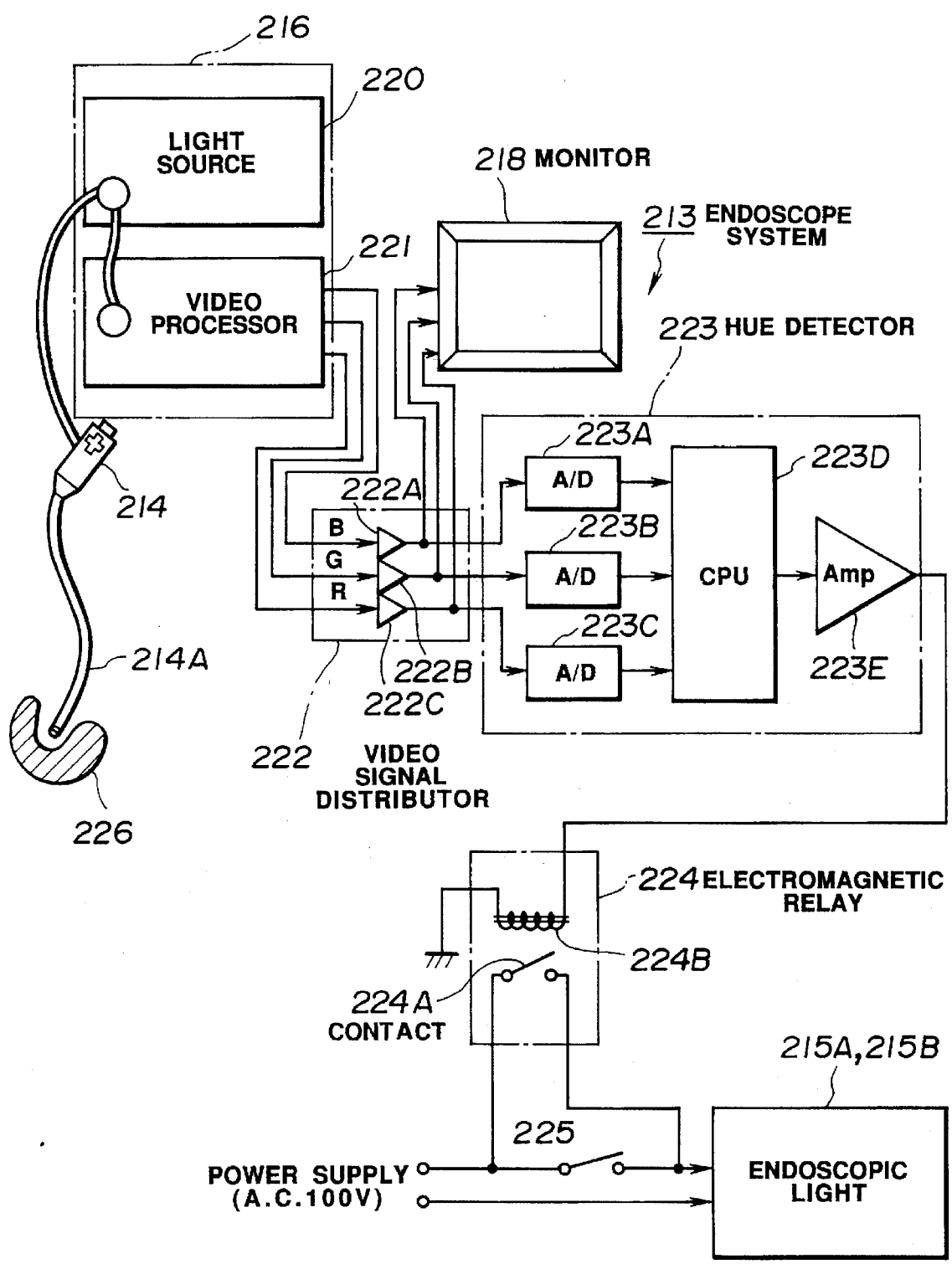

An endoscope system 213 shown in FIGS. 32 and 33 is a system for obtaining endoscopic images with an electronic endoscope 214 connected, which is installed in an endoscope room and also controls endoscope system lights 215A and 215B.

As shown in FIG. 32, not only the endoscope system lights 215A and 215B but also an endoscope system storage rack 216 accommodating the power unit for the endoscope system 213, an examination bed in which a subject lies down, and a stand 219 for holding the endoscope lights 215A and 215B, and a monitor 218 supported by the stand 219 to be freely rotatable.

Figure 35:
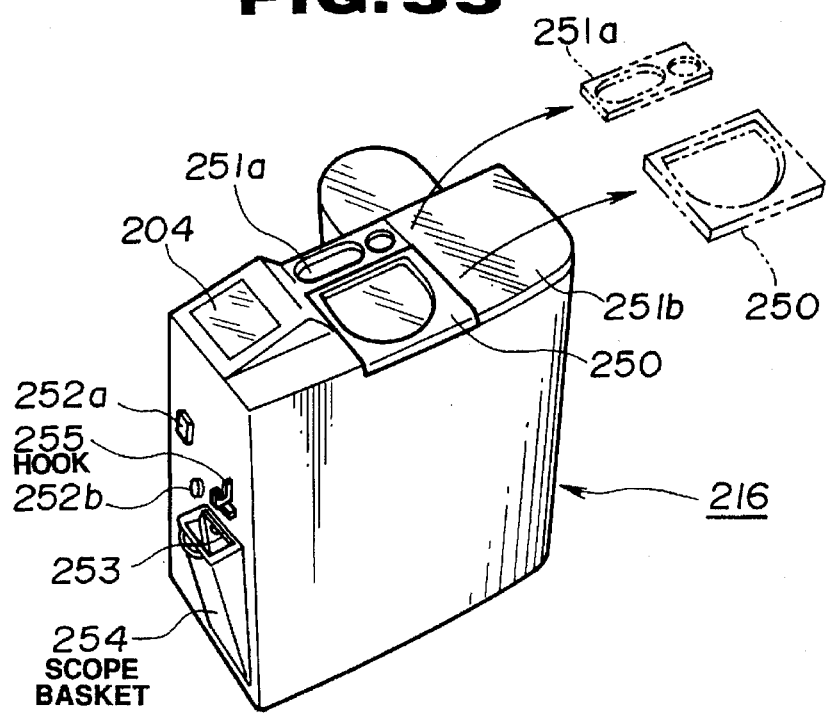

FIGS. 35 and 36 show an example of the appearance of the endoscope system storage rack 216. The endoscope system storage rack 216 accommodates an endoscopic light source and a video processor, which are described later. A centralized operation panel 204 for controlling the on and off operations of the power supply for supplying power to each unit is formed in the upper front of the endoscope system storage rack 216. An endoscopic tray 250 which loads a sterilized endoscope and is freely detachable, and accessory trays 251a and 251b which load treatment adapters and other accessories necessary for endoscopic examination and are freely detachable are installed on the top of the endoscope system storage rack 216. Receptacles 252a and 252b for connecting an endoscope, an endoscopic light source, and a video processor, an endoscope basket 254 which supports an endoscope holder 253 accommodating an unclean endoscope so that the endoscope holder will be freely detachable and which can be closed freely, and an endoscope hook 255 for holding an unclean endoscope are formed on the side of the endoscope system storage rack 216.

Figure 36A:
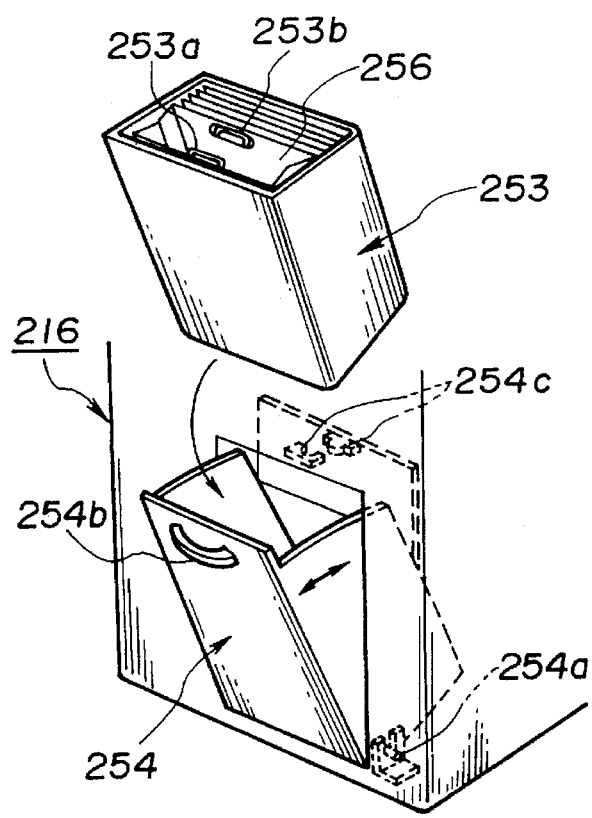
FIG. 36a is an explanatory diagram showing an endoscope storage holder.
Figure 36B:
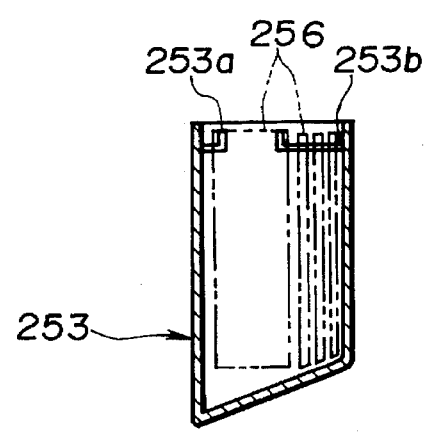
FIG. 36b shows a cross section of the endoscope storage holder.

As shown in FIGS. 36a and 36b, a freely-rotatable axis 254a is installed at the bottom of the endoscope basket 254. A hook 254b for drawing out the endoscope basket 254 is projecting from the upper part of the endoscope basket 254. A lock mechanism 254c is formed on the back end of the endoscope basket 254 to lock the endoscope basket 254 closed. The endoscope holder 253 has hooks 253a and 253b on its internal side. A plurality of disposable paper or vinyl bags 256 are hung on the hooks 253a and 253b for storage. One of the disposable bags 256 is placed in the endoscope holder 253, and hung on the bag hooks 253a and 253b to so that it will be open all the time to accept an endoscope. Other bags are stored behind the bag hook 253b to be used successively.

Figure 37:
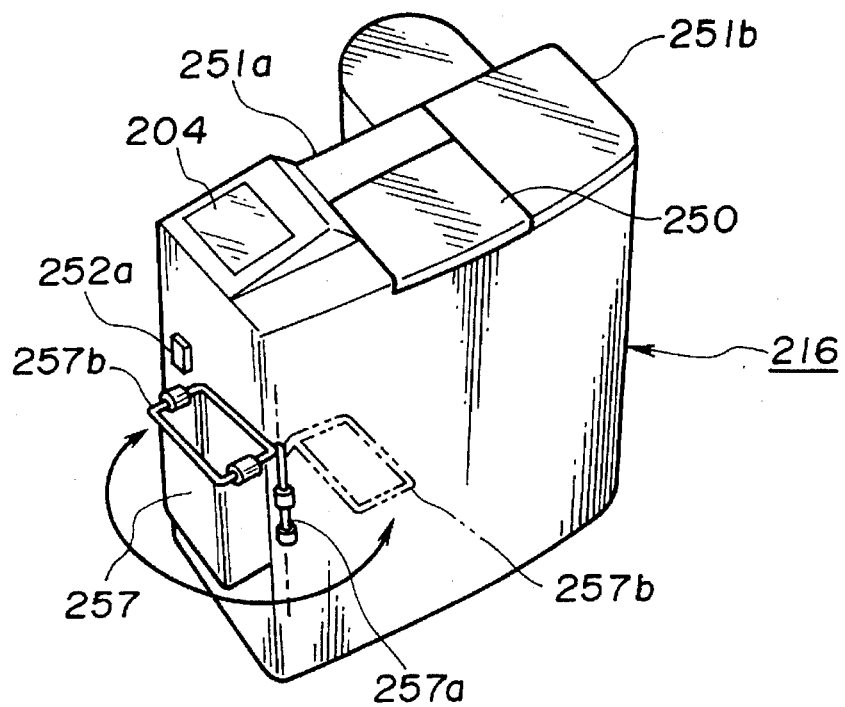
Figure 38:
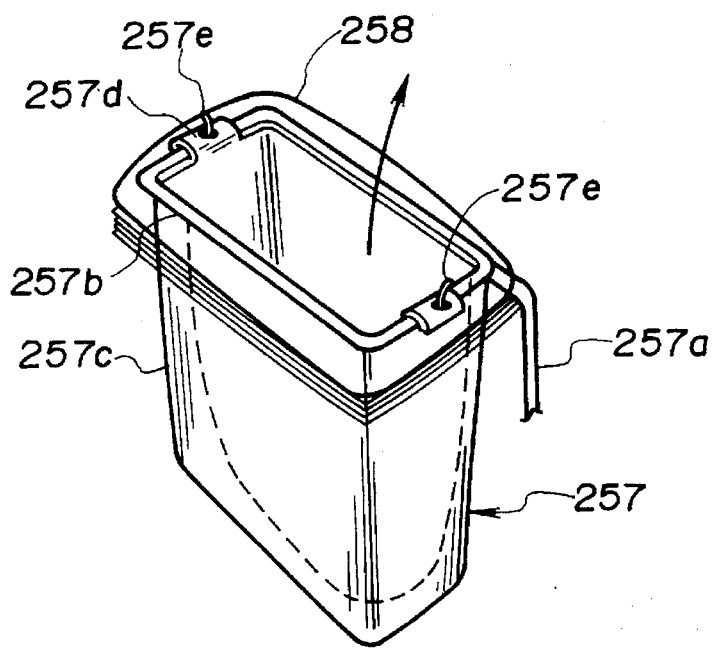

FIGS. 37 and 38 show other example of an endoscope basket differing from the endoscope basket 254 shown in FIG. 36. An endoscope basket 257 has a freely-rotatable axis 257a on the side of an endoscope system storage rack 216. A mouth frame 257b is coupled to the axis 257a. A basket body 257c is provided so that it can be engaged with and detached from the frame 257b. The basket body 257c has locking hooks 257d on both sides of the opening. The locking hooks 257d are hung on the frame 257b to hold the basket body 257c. Pins 257e are projecting from the holes of the locking hooks 257d, on which a vinyl endoscope storage bag 258 placed in the basket body 257c for storing an unclean endoscope is caught and fixed.

An unclean endoscope is stored in the endoscope storage bag 258 or a disposable bag 256. Thus, a user can carry the unclean endoscope to a cleaning room without making his/her hand dirty.

As shown in FIG. 33, the endoscope system 213 comprises the electronic endoscope 214 that incorporates a solid-state imaging device, which is not illustrated, in the distal end 214A, and is used to observe a subject 226, an endoscopic light source 220 for supplying illumination light to the electronic endoscope 214, a video processor 221 that outputs red (R), green (G), and blue (B) signals and includes an automatic light adjustment function for reserving an optimal quantity of light by adjusting a diaphragm, which is not illustrated, in the endoscopic light source 220, a video signal distributor 222 having amplifiers 222A, 222B, and 222C for amplifying R, G, and B composite signals originating from the video processor 221, a monitor 218 for receiving signals from the three amplifiers of the video signal distributor 222 and displaying endoscopic images, a hue detector 223 for receiving signals from the three amplifiers of the video signal distributor 222 and determining whether or not the endoscope 214 is being used for examination, an electromagnetic relay 224 for turning on or off a contact 224A in response to an output signal of the hue detector 223, and an illumination switch 225 which is connected in parallel with the contact 224A and used to manually turn on or off the endoscope system lights 215A and 215B. The endoscope system 213 turns on or off power (for example, 100 VAC) applied to the endoscope system lights 215A and 215B.

The hue detector 223 comprises digital/analog (A/D) converters 223A, 223B and 223C which converts R, G, and B signals sent from the three amplifiers of the video signal distributor 222 into digital signals and outputs the digital signals, a CPU 223D which inputs digital signals sent from the A/D converters 223A, 223B, and 223C and checks whether or not the endoscope 214 is being used for examination, and an amplifier 223E for amplifying an output signal of the CPU 223D. When examination is not done, the amplifier 223E outputs a signal, a solenoid 224B of the electromagnetic relay 224 is actuated, and the contact 224A is turned on.

The functions of the embodiment are explained in conjunction with FIG. 34. Criteria are predetermined according to the levels of R, G, and B components. Based on the criteria, it is checked whether or not an endoscope is being used for examination. Depending on the result, lights are turned on or off.

As shown in FIG. 34a, an endoscope 214 is inserted into a body cavity of a subject 226. During examination, the body cavity of the subject 227 is characterized by an R component that is more intense and higher in level than other G and B components. Therefore, the R signal the A/D converter 223C outputs is higher, while the output levels of the A/D converters 223A and 223B become lower. In this case, the CPU 223D assesses this state with respect to the pre-set criteria and determines that the endoscope 214 is being used for normal examination. Then, the CPU 223D turns off the contact 224A of the electromagnetic relay 224 using the amplifier 223E. As a result, the endoscope system lights 215A and 215B go out.

Next, as shown in FIG. 34b, when the distal end 214A of the endoscope 214 has approached the subject 226 too closely, the automatic light adjustment function of the video processor 221 is actuated. As a result, white halation continues until the diaphragm is narrowed. At this time, all the A/D converters 223A, 223B, and 223C have a high signal level. The CPU 223D assesses this state with respect to the criteria and determines that the endoscope 214 is being used for examination. Then, the endoscope system lights 215A and 215B go out.

On the other hand, as shown in FIG. 34c, when the endoscope 214 is removed from the subject 226, the R component attenuates rapidly to be the same level as that of G and B components. Then, the CPU 223D assesses this state with respect to the criteria and determines that examination is under way. Then, the CPU 223D turns on the contact 224A of the electromagnetic relay 224 using the amplifier 223E. As a result, the endoscope system lights 215A and 215B light.

As shown in FIG. 34d, when the endoscope 214 is dismounted from the endoscope system 213 (for cleaning), the levels of color components become almost zero. Then, the CPU 223D assesses the state with respect to the criteria and determines that examination is not done. As a result, the endoscope system lights 215A and 215B light.

The criteria specified in the CPU 223D are set so that when the level of, for example, an R component exceeds a certain threshold, it is determined that examination is under way, and that when the levels of R, G, and B components are below a certain value, it is determined that examination is not done.

In this embodiment, while the endoscope 214 is being used for examination, the endoscope system lights 215A and 251B go out automatically. When examination is not done, the endoscope system lights 215A and 215B light automatically. A user need not move to turn on or off the switches. The lights 218A and 218B can be controlled merely by inserting the distal end 214A of the endoscope 214 into the subject 226. This reduces the load to a user. The user can concentrate on a principal object of endoscopic observation.

Lights are turned on or off based on the use state of an endoscope. Instead of turning on or off the lights, the quantity of light may be controlled depending on the use state of the endoscope.

In this embodiment, the electronic endoscope 214 is given as an example. The embodiment can apply to a fiberscope. In this case, however, an apparatus for converting optical images into electric signals must be installed.

FIGS. 39 to 48 show the eighth embodiment of the present invention.

In this embodiment, unlike the sixth embodiment in which the on and off operations of the power supplies of units are controlled, lights in an endoscope room are controlled. Other components and functions identical to those of the sixth and seventh embodiments are assigned the same symbols. The description is omitted.

Figure 39:
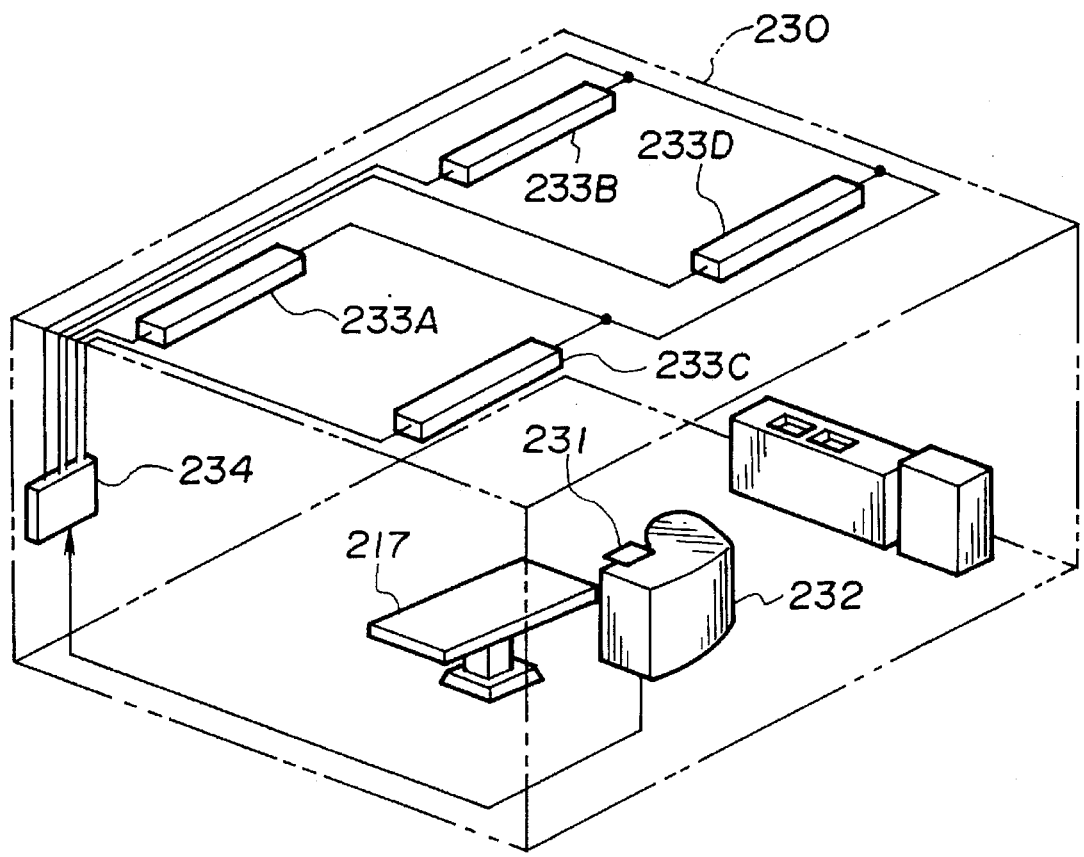

An endoscope room 230 shown in FIG. 39 is equipped with a light source 220, a video processor 221, an endoscope system storage rack 232 having a centralized operation panel 231 for centralizing control of room lights, four room lights 233A, 233B, 233C, and 233D (hereafter, they may be represented as room lights 233) installed on the ceiling of the endoscope room 230, and a light control 234 for turning on or off the room lights 233 according to a command sent from the centralized operation panel 231.

Figure 42:
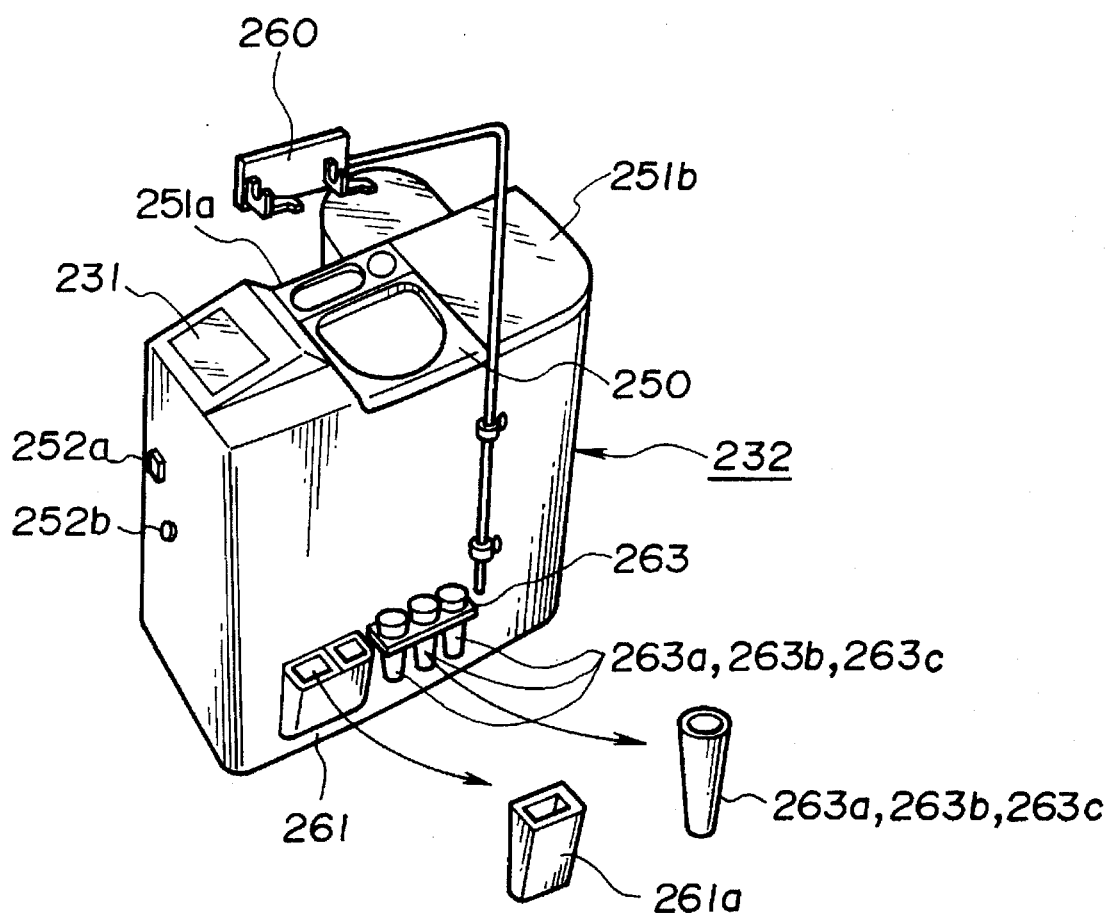

The centralized operation panel 231 is installed in the upper front of the endoscope system storage rack 232 as shown in FIG. 42. An endoscope hanger 260 on which an unused or unclean endoscope is hung is formed on the side of the endoscope system storage rack 232. A storage bracket 261 for holding an endoscope end receptor 261a in which the distal end of an endoscope is mounted so that the endoscope end receptor 261a can be detached freely, and a bracket 263 for holding cups 263a, 263b, and 263c containing pure water or alcohol for cleaning an endoscope at hand so that the cups can be detached freely are provided on the lower side of the endoscope system storage rack 232.

Figure 43:
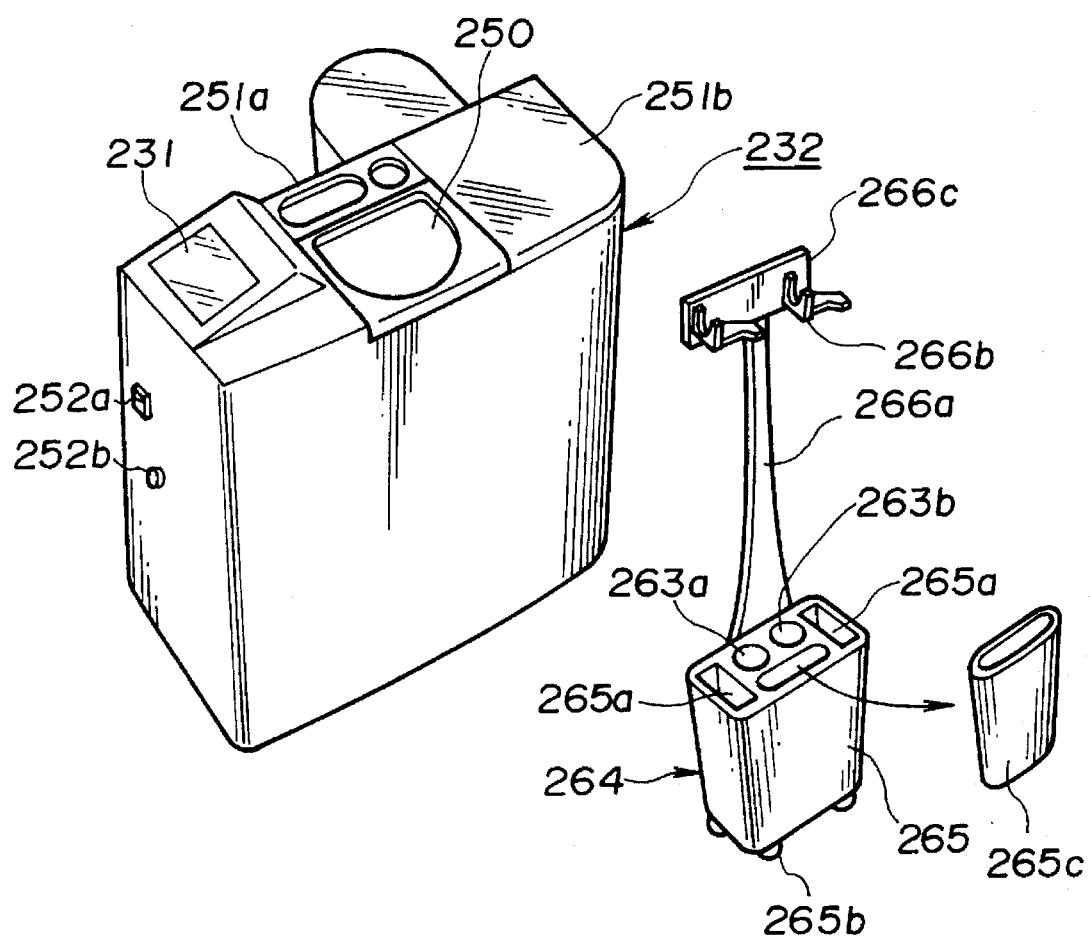

FIG. 43 shows a mobile hanger trolley 264 which substitutes for the endoscope hanger 260 and is constructed as an independent unit. The hanger trolley 264 comprises a trolley main unit 265 in which a distal end receiving cup 265a for storing the distal end of an endoscope can be accommodated to be freely detachable, a hanger section 266a extending from the top side of the trolley main unit 265, and a hook mounting plate 266c from which two hooks 266b are projecting and used to hang endoscopes on them. The trolley main unit 265 has four freely-movable casters 265b on its bottom. In addition to the distal end receiving cup 265a, an empty cup 265c is also accommodated in the trolley main unit 265 to be freely detachable. Using the hanger trolley 264, unclean endoscopes can be held in the hanger trolley 264 and carried into a cleaning room, but not enclosed in bags.

Figure 44:
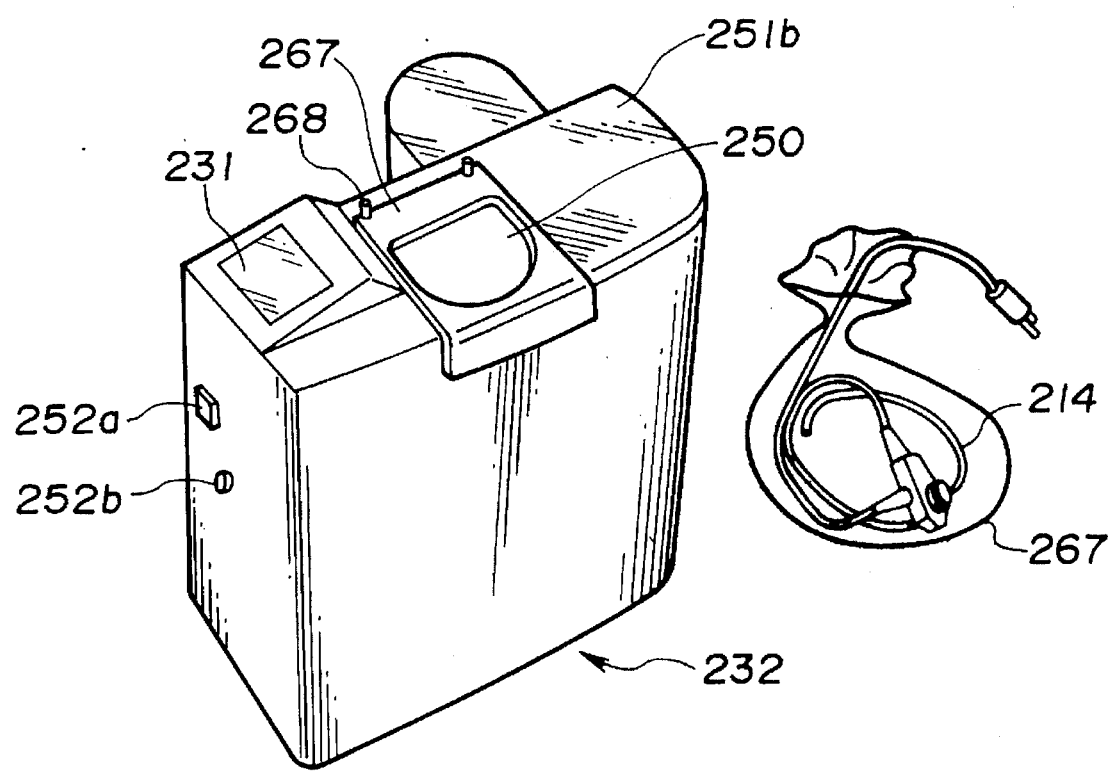

FIG. 44 shows an endoscope system storage rack 232 in which a plurality of sheets 267 for wrapping up unclean endoscopes is placed on an endoscope tray 250. The endoscope system storage rack 232 has two pins 68 for holding sheets 267 at the side end of the top. An unclean endoscope 214D is wrapped up in a sheet 267, carried to a cleaning room, then cleaned and sterilized.

Figure 45:
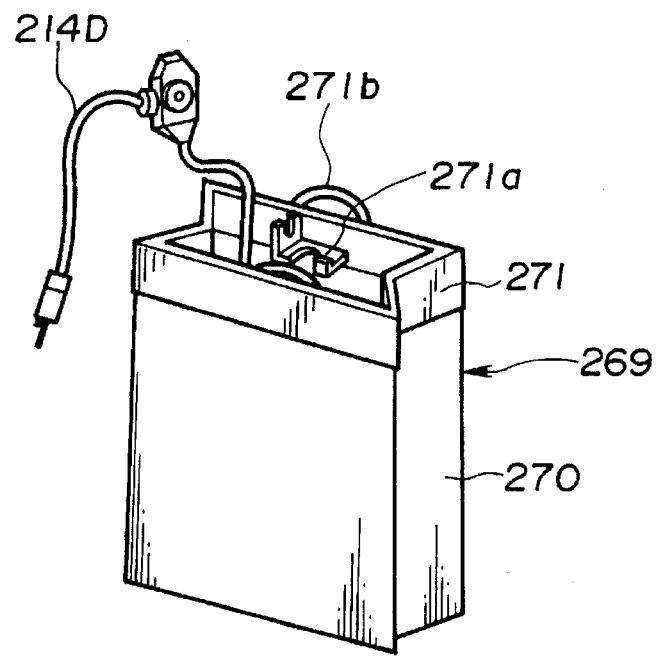

FIG. 45 shows a light-weight and compact endoscope disposable bag 269 substituting for sheets 267. The endoscope disposable bag 269 comprises a bag 270 which is made from waterproof paper and used to store an unclean endoscope 214D, and a freely-detachable frame 271 made from elastic material to reinforce the opening of the bag 270. The frame 271 includes a hook 271a for holding an endoscope inside the opening and two grips 271b projecting above the opening. Using the endoscope disposable bag 269, the unclean endoscope 214D can be put in the bag 270 perfectly. The grips 271b makes the endoscope disposable bag 269 portable.

Figure 46:
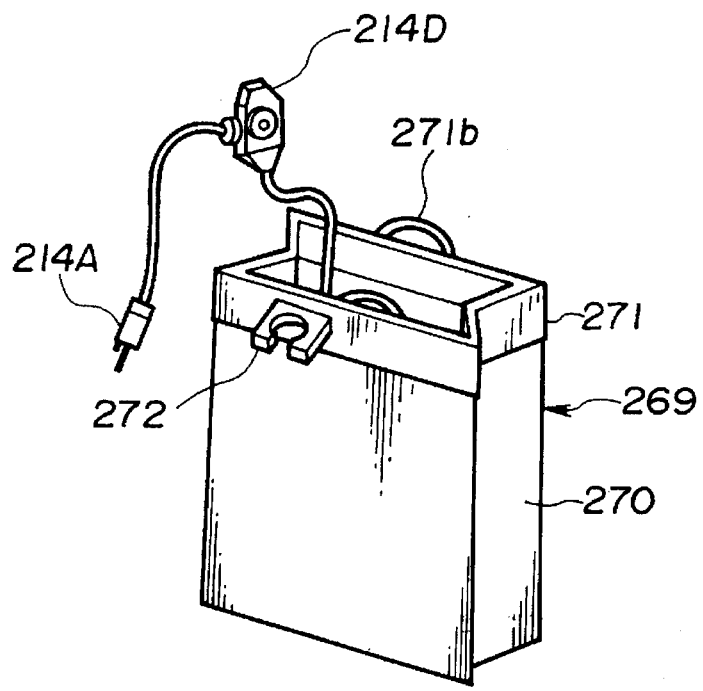
Figure 47:
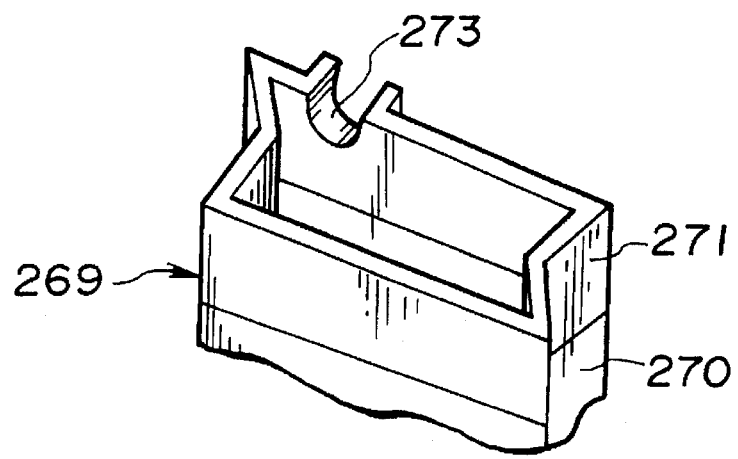
Figure 48A:
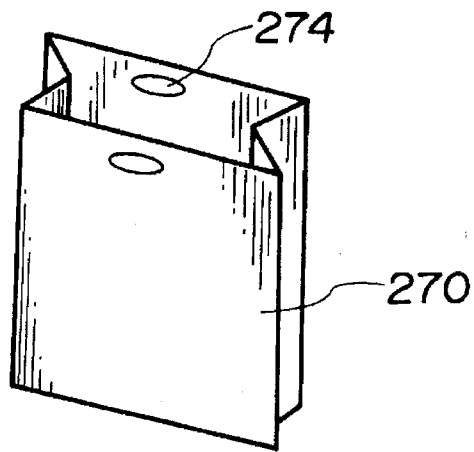
FIG. 48a shows an appearance of the storage section of an endoscope storage holder formed as a separate unit.
Figure 48B:
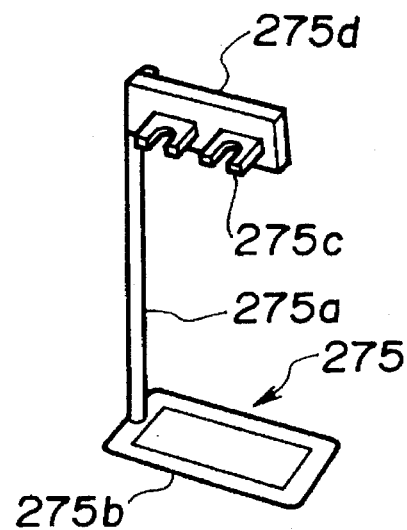
FIG. 48b shows an appearance of an endoscope holder of the endoscope storage holder.

For the endoscope disposable bag 269 shown in FIG. 46, unlike that in FIG. 45, a hook 272 is provided on the external side of the frame 271. An unclean endoscope 214D can be carried with the distal end 214A locked in the hook 272. FIG. 47 shows an endoscope disposable bag 269 whose hook 273 is formed as part of the upper end of the frame 271. In the same way as the endoscope disposable bag 269 shown in FIG. 46, an unclean endoscope 214D can be carried with the distal end 214A locked. FIGS. 48a and 48b show an endoscope disposable bag in which a bag and a member for holding an endoscope are provided separately. A bag 270 shown in FIG. 48a is used to store an unclean endoscope and carried away. Holes 274 are formed as grips in the upper parts of the bag 270. An endoscope holder 275 shown in FIG. 48b comprises a stand 275b having an arm 275a, and a hook mounting plate 275d having hooks 275c on which endoscopes are hung.

Figure 41:
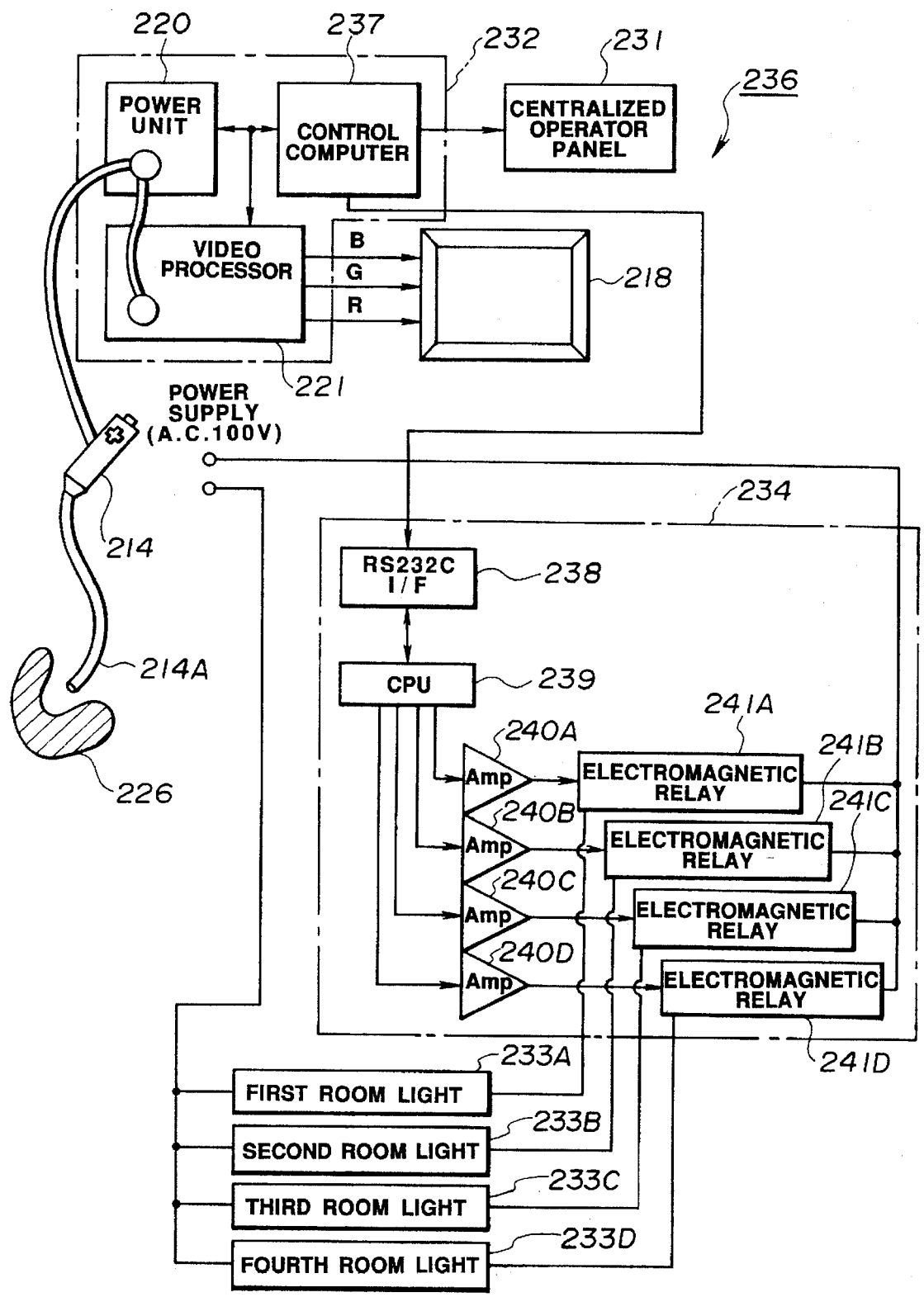

As shown in FIG. 41, the endoscope system 236 comprises the endoscope 214, light source 220, video processor 221, monitor 218, and centralized operation panel 231, as well as a control computer 237 which is accommodated in the endoscope system storage rack 232 and outputs an on or off command signal according to the on of off information the centralized operation panel 231 outputs. Thus, in response to the on or off command signal the control computer 237 outputs, the light control 234 turns on or off the room lights 233.

The light control 234 comprises an interface port; such as, an RS-232C serial interface for converting an on or off command signal the control computer 237 outputs into a serial signal, a CPU 239 for processing a serial command signal the serial interface 238 outputs, amplifiers 240A, 240B, 240C, and 240D (hereafter, they may be represented as amplifiers 240) for amplifying four command signals the CPU 239 outputs in parallel, and electromagnetic relays 241A, 241B, 241C, and 241D (hereafter, they may be represented as electromagnetic relays 241) which turn on or off their contacts according to four output signals the amplifiers 240 outputs and turn on or off the power supply for room lights 233A, 233B, 233C, and 233D.

Figure 40:
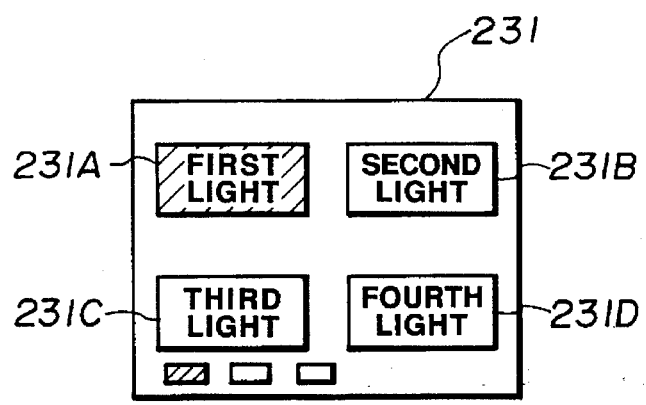

The centralized operation panel 231 has, as shown in FIG. 40, four switches and indicators 231A, 231B, 231C, and 231D on its front.

In this embodiment, the switches and indicators 231A, 231B, 231C, and 231D on the centralized operation panel 231 are located near a user position for manipulating an endoscope. Therefore, a user need not move to the wall to turn on or off the room lights 233. Thus, the on and off operations of the room lights 233 can be centralized with ease. The user is relieved from a nuisance of turning on or off equipment one by one and can turn off the room lights 233 quickly and easily. This prevents unused room lights from being held on, thus eliminating excessive power consumption. Other components, functions, and effects are identical to those of the sixth embodiment. The description is, therefore, omitted.

Figure 49:
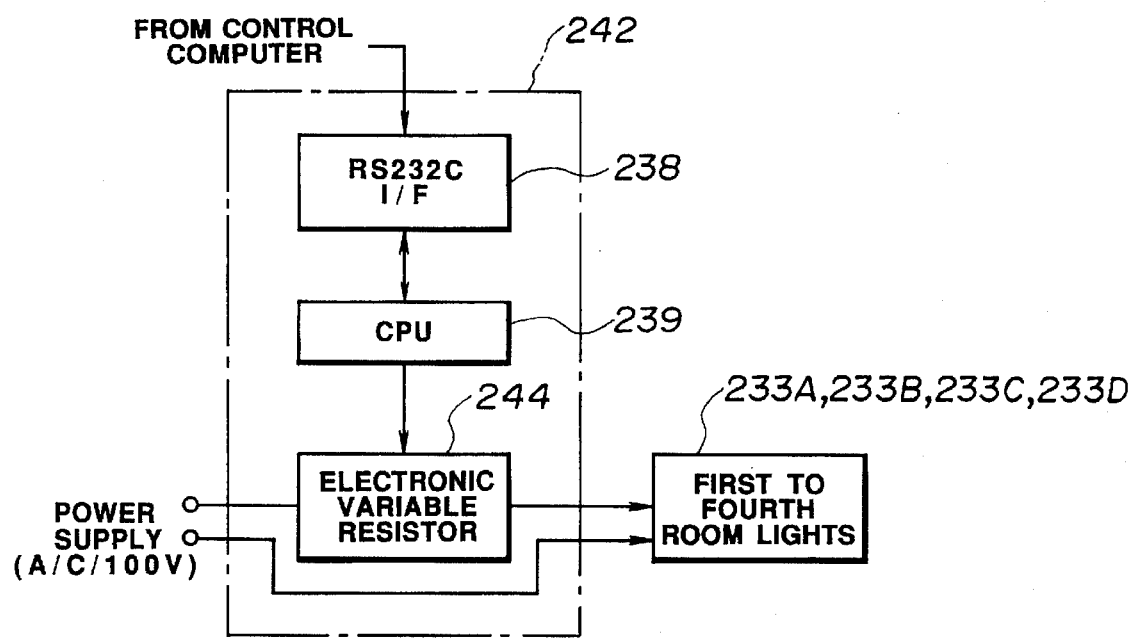
FIGS. 49 and 50 relate to the ninth embodiment of the present invention.
Figure 50:
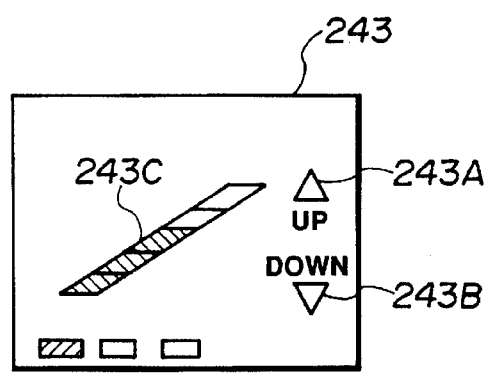

FIGS. 49 and 50 relate to the ninth embodiment of the present invention. FIG. 49 schematizes the configuration of a light control, and FIG. 50 is a front view of a centralized operation panel.

According to this embodiment, unlike the eighth embodiment in which the on and off operations of room lights are controlled, a system centralizes light adjustment control of room lights. Other components and functions identical to those of the eighth embodiment are assigned the same symbols. The description is omitted.

A centralized operation panel 243 shown in FIG. 50, unlike the light control 234 according to the eighth embodiment, specifies a variable quantity of light of room lights 233 to be adjusted, comprising an UP button 243A which increases the quantity of light of the room lights 233 in increments every time it is pressed, a DOWN button 243B which reduces the quantity of light of the room lights 233 in decrements every time it is pressed, and a brightness indicator 243C which consists, for example, of multiple light emitting diodes to indicate a quantity of light or brightness of the room lights 233 digitally.

A light control 242 shown in FIG. 49, unlike the light control 234 of the eighth embodiment, controls light adjustment for room lights, including an electronic variable resistor 244 which inputs a quantity specified with the UP button 243A or DOWN button 243B through the control computer 237, serial interface 238, and CPU 239 and varies resistance according to the quantity specified. The electronic variable resistor 244 inputs power of 100 VAC, varies and outputs voltage according to the fluctuation in resistance, and thus varies the quantity of light of the room lights 233.

In this embodiment, a user can finely vary a quantity of light of room lights 233 by hand. Other components, functions, and effects are identical to those of the eighth embodiment. The description is omitted.

Figure 51:
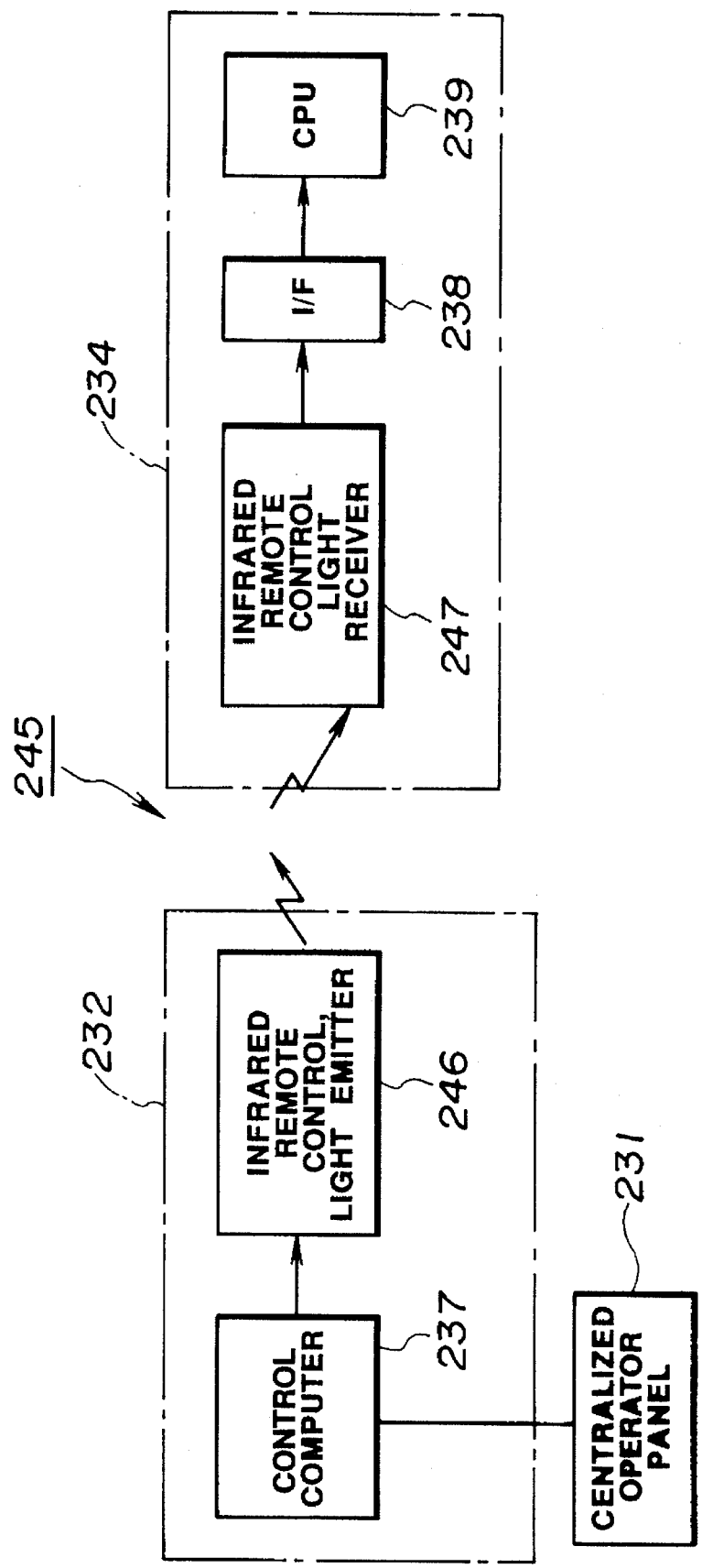
FIG. 51 schematizes the configuration according to the tenth embodiment of the present invention.

FIG. 51 schematizes a configuration according to the tenth embodiment of the present invention.

According to this embodiment, unlike the seventh and ninth embodiments in which room lights are wired and controlled, a system centralizes control of room lights of a wireless basis. Other components and functions identical to those of the seventh and ninth embodiments are assigned the same symbols. The description is omitted.

An endoscope system 245 shown in FIG. 51 has an infrared remote control light emitter 246 which is accommodated in an endoscope system storage rack 232, inputs a command signal sent from the centralized operation panel 231 via a control computer 237, and converts it into an infrared light command signal to emit light. On the other hand, a light control 234 has an infrared remote control light receiver 247 which receives light of an infrared light command signal emitted from the infrared remote control light emitter 246 and outputs it as an electric signal. The light control 234 uses an interface 238 and a CPU 239 to control the on and off operations of room lights 233.

This embodiment obviates installation of light cables, which, therefore, will prove effective for an existing room. Other components, functions, and effects are identical to those of the eighth embodiment. The description is omitted.

Combinations of the sixth to tenth embodiments are feasible.

Figure 52:
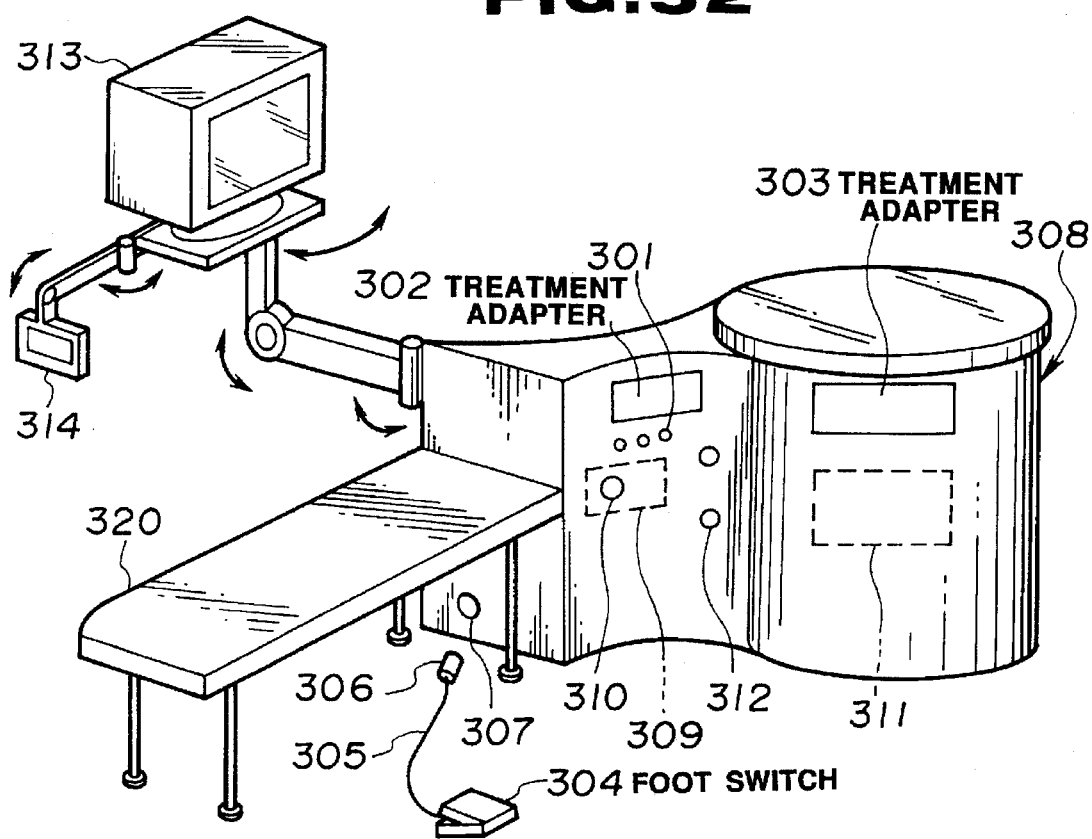
FIGS. 52 and 53 relate to the eleventh embodiment of the present invention.
Figure 53:
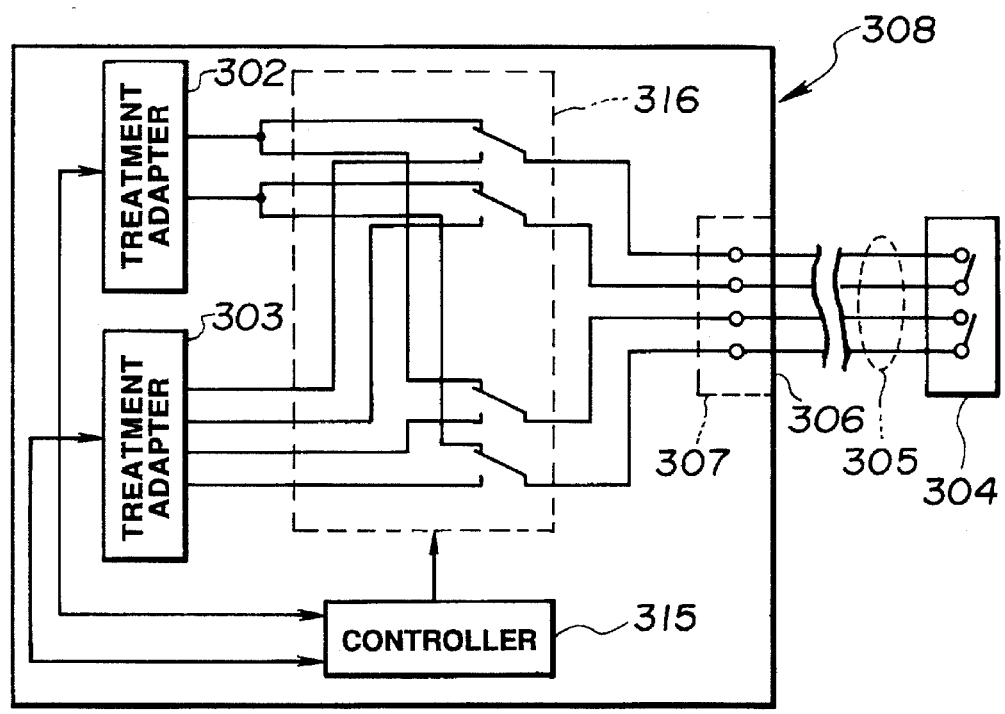

FIGS. 52 and 53 relate to the eleventh embodiment of the present invention. FIG. 52 is a configuration diagram of an endoscope system, and FIG. 53, an explanatory diagram of a switching means.

An endoscope system according to the eleventh embodiment comprises, as shown in FIG. 52, a light source 309 for supplying illumination light to an endoscope, a video processor 311 for an electronic endoscope, a control main unit 308 accommodating, a treatment unit 302; such as, a hemostatic coagulation unit, and a treatment unit 303; such as, a diathermic cutter, a bed 320 on which a patient undergoing diagnosis or treatment using the endoscope system lies down, a main monitor 313 for visualizing a video signal originating from the video processor 311, and an endoscope (including an electronic endoscope) which is not illustrated.

To the endoscope system, a submonitor 314 assisting the main monitor 313 is connected to be freely detachable.

The control main unit 308 incorporates the treatment units 302 and 303, light source 309, and video processor 311.

Arranged on the cabinet (housing) of the control main unit 308 are a connector 307 to which a plug of a foot switch 304 or a drive control means for the treatment units 302 and 303, which is described later, is connected to be freely detachable, a connector 301 for the treatment unit 302 or 303 to which a plug of a treatment adapter, which is not illustrated, is connected to be freely detachable, a connector 310 for the light source 309 to which a light plug of an endoscope (including an electronic endoscope), which is not illustrated, is connected to be freely detachable, and a connector 312 for the video processor 311 to which an electric plug attached to the end of an universal cord of an electronic endoscope, which is not illustrated, is connected to be freely detachable.

To the foot switch 304, a cable 305 is connected. A plug 306 is attached to the end of the cable 305.

When an endoscope is used for observation, the light plug of the endoscope is connected to the connector 310. If the endoscope is an electronic endoscope, the electric plug of the electronic endoscope is connected to the connector 312.

When the endoscope (including an electronic endoscope) is used to treat a patient, a treatment adapter employed is connected to the connector 301. The treatment unit 302 or 303 to which the treatment adapter is connected via the connector 301 or the treatment unit 302 or 303 to which the previously-mentioned treatment adapter is connected directly is driven and controlled by stepping on the foot switch 304.

When the endoscope system is employed to observe or treat a patient, the patient is asked to lie down on the bed 320.

The control main unit 308, as shown in FIG. 53, for example, is equipped with the treatment units 302 and 303, a controller 315 for switching the connection of the connector 307 into the treatment unit 302 or 303 when the power supply of the treatment unit 302 or 303 is turned on, and a switching device 316; such as, a relay for switching the connection of the connector 307 into the treatment unit 302 or 303 under the control of the controller 315.

The functions of the endoscope system having the foregoing configuration are explained below.

When the power supply of the treatment unit 302 or 303 is turned on, the controller 315 controls the switching device 316 to connect the connector 307 with the treatment unit 302 or 303 whose power supply is turned on as described previously.

Thereby, when the foot switch 304 is stepped on, the treatment unit 302 or 303 whose power supply is turned on is driven and controlled as described previously.

When the power supplies of the treatment units 302 and 303 are turned on simultaneously, the controller 315 connects the connector 307 to the treatment unit 302 or 303 according to the predetermined priority order.

Only a single foot switch is needed to switch, drive, and control the treatment units 302 and 303. Thus, the switching operation is simplified.

Figure 54:
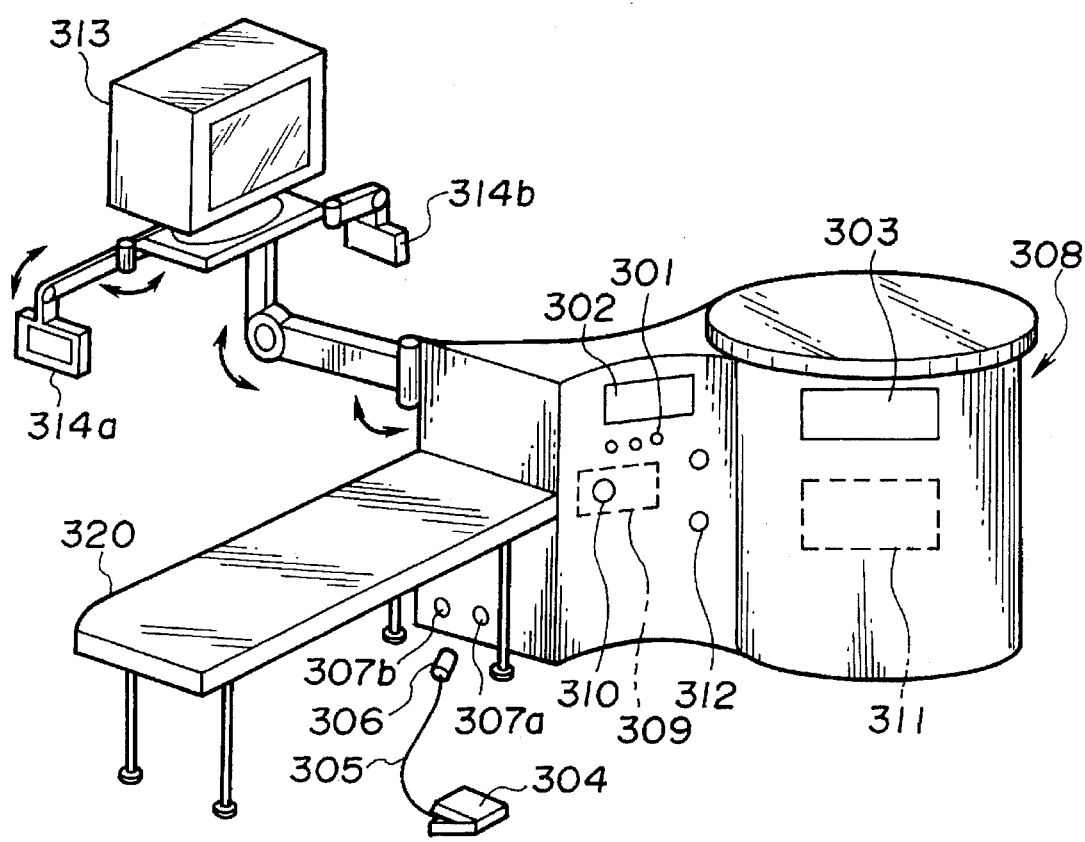
FIGS. 54 and 55 relate to the twelfth embodiment of the present invention.
Figure 55:
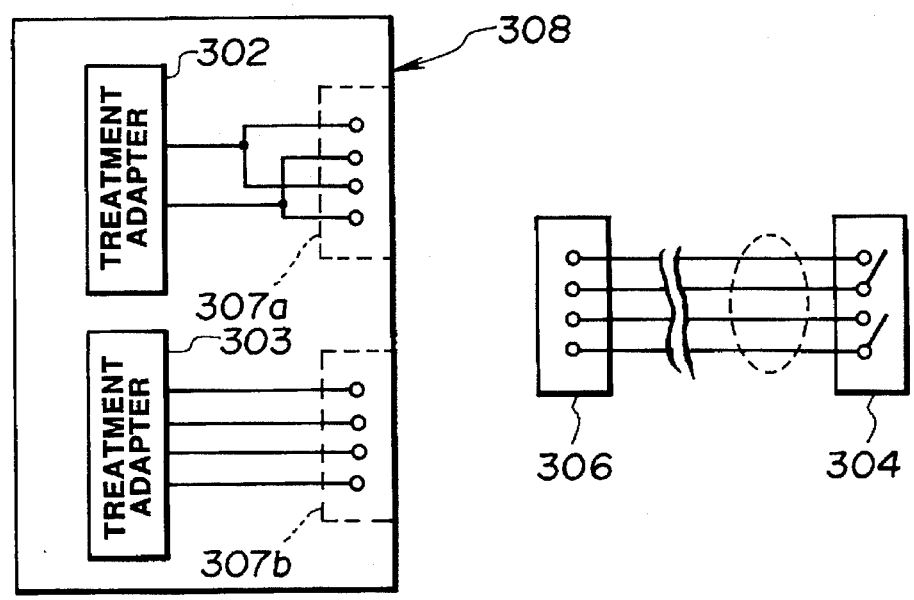

FIGS. 54 and 55 relate to the twelfth embodiment of the present invention. FIG. 54 is a configuration diagram of an endoscope system, and FIG. 55, an explanatory diagram of a switching means. The same components as those of the previous embodiments are assigned the same symbols. The description is omitted.

An endoscope system comprises, as shown in FIG. 54, a control main unit 308 accommodating a light source 309, a video processor 311, and treatment units 302 and 303, a bed 320, a main monitor 313, and an endoscope (including an electronic endoscope) which is not illustrated.

Submonitors 314a and 314b assisting the main monitor 313 are connected to the endoscope system so that they can be detached freely.

The control main unit 308, as described previously, incorporates the treatment units 302 and 303, light source 309, and video processor 311.

Arranged on the cabinet (housing) of the control main unit 308, includes for example, connectors 307a and 307b to which a plug 306 of a foot switch 304 or a drive control means for the treatment units 302 and 303, a treatment adapter connector 301, a light source connector 310, and a video processor connector 312.

The control main unit 308 is, for example, as shown in FIG. 55, equipped with the treatment units 302 and 303, the connector 307a for the treatment unit 302, and the connector 307b for the treatment unit 303.

The functions of the endoscope system having the foregoing configuration are explained below.

When using the treatment unit 302, an operator connects the plug 306 of the foot switch 304 to the connector 307a. When the treatment unit 303 is used, the plug 306 of the foot switch 304 is connected to the connector 307b.

Thereby, when the foot switch 304 is stepped on, the treatment unit 302 or 303 corresponding to the connector 307a or 307b to which the aforesaid plug 306 is connected is driven and controlled.

An operator himself/herself selects the connector of an intended treatment unit. Therefore, an intended treatment unit is selected correctly.

Other components, functions, and effects are identical to those of the eleventh embodiment.

A treatment unit to which the foot switch is connected may be indicated with a lamp.

The aforesaid function is available even when two or more treatment units are employed.

The drive control means is not confined to a foot switch but may be a switch in an endoscope operation unit.

FIGS. 56 to 60 show a thirteenth embodiment of the invention.

Figure 56:
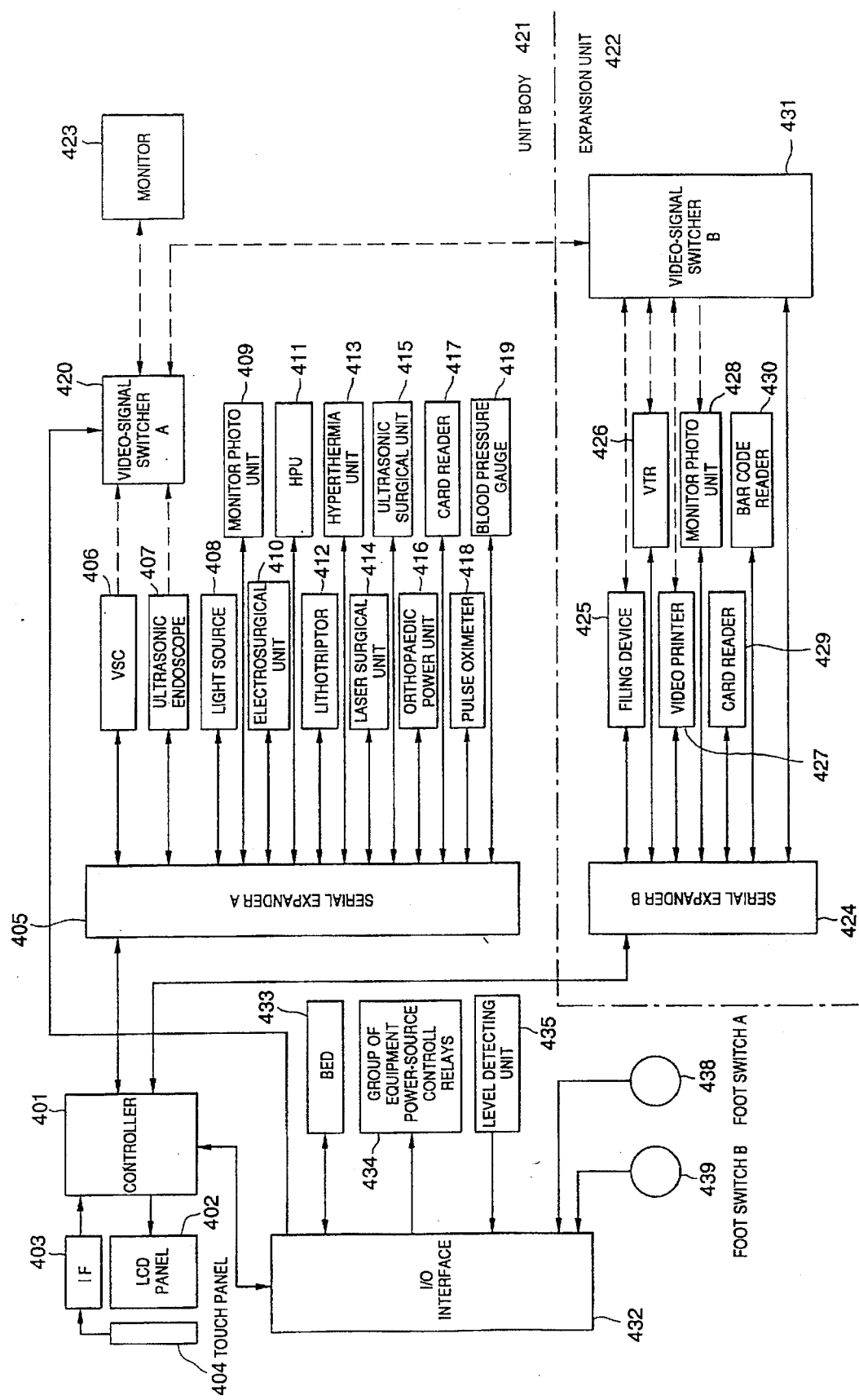
FIG. 56 is a block diagram showing an entire arrangement of an endoscope system according to a thirteenth embodiment of the invention.

In the thirteenth embodiment, as shown in FIG. 56, a controller 401 is provided which serves as centralized control means. An LCD panel 402 for displaying graphic such as a control picture plane of a peripheral device and the like is connected to the controller 401. Further, a touch panel 404 is connected to the controller 401 through an interface 403.

An endoscope system according to the thirteenth embodiment is separated into a unit body 421 on which required pieces of equipment are loaded in collection on hand of an operator and which is used in combination with an endoscope when various kinds or types of medical treatments are performed together with endoscope inspection, and an expansion unit 422 on which other equipment are loaded.

Serial expander A 405 is connected to the controller 401. A video system center (VSC) 406, an endoscopic ultrasonic system 407, a light source 408, a monitor photo unit 409, and an electrosurgical unit 410, an HPU (heatprobe unit) 411, a lithotriptor 412, a hyperthermia unit 413, a laser surgical unit 414, an ultrasonic surgical unit 415, and an orthopedic power unit 416, which all serve as electric treatment devices, and a card reader 417, a pulse oximeter 418, and a blood pressure gauge 419 are connected to the serial expander A 405. A control signal from the controller 401 is sent to the aforesaid various devices 406–419 through the serial expander A 405, and data such as various kinds of setting values, output values from various equipment and the like are exchanged by serial communication. In the thirteenth embodiment, communication of the control signal follows the standard of RS-232C. In this connection, in FIG. 56, the control signal is shown by the solid-line arrows.

The video system center 406, to which the endoscope is connected, and the endoscopic ultrasonic system 407 have respective image output ends thereof which are connected to video-signal switcher A 420. Video signals that are respective outputs from the video system center 406 and the endoscopic ultrasonic system 407 are inputted to video-signal switcher A 420. In this connection, in FIG. 56, the video signal is indicated by the arrows of the broken lines.

A video signal from the expansion unit 422 is also inputted to the video-signal switcher A 420 to switch the video signals that are the respective outputs from the video system center 406, the endoscopic ultrasonic system 407 and the expansion unit 422, to thereby output the switched signals to a monitor 423.

The expansion unit 422 is provided with serial expander B 424, and is connected to the controller 401. A filing device 425, a VTR 426, a video printer 427, a monitor photo unit 428, a card reader 429 and a bar code reader 430 are connected to serial expander B 424. A control signal is exchanged between these devices 425–430 and the controller 401 through serial expander B 424.

The filing unit 425, the VTR 426, the video printer 427 and the monitor photo unit 428 have respective image output ends thereof which are connected to video-signal switcher B 431 so that video signals that are outputs from the aforesaid respective devices 425–428 are inputted to video-signal switcher B 431. Video-signal switcher B 431 has an output end which is connected to video signal switcher A 420 of the unit body 421. Video signals that are respective outputs from the filing device 425, the VTR 426, the video printer 427, the monitor photo unit 428 are switched by video signal switcher B 431, and are outputted to video-signal switcher A 420.

Moreover, a bed 433, a level detecting unit 435 and a group of equipment power-source control relays 434 for controlling ON/OFF of power for equipment are connected to the controller 401 through an I/O interface 432 which exchanges a parallel control signal.

Figure 57:
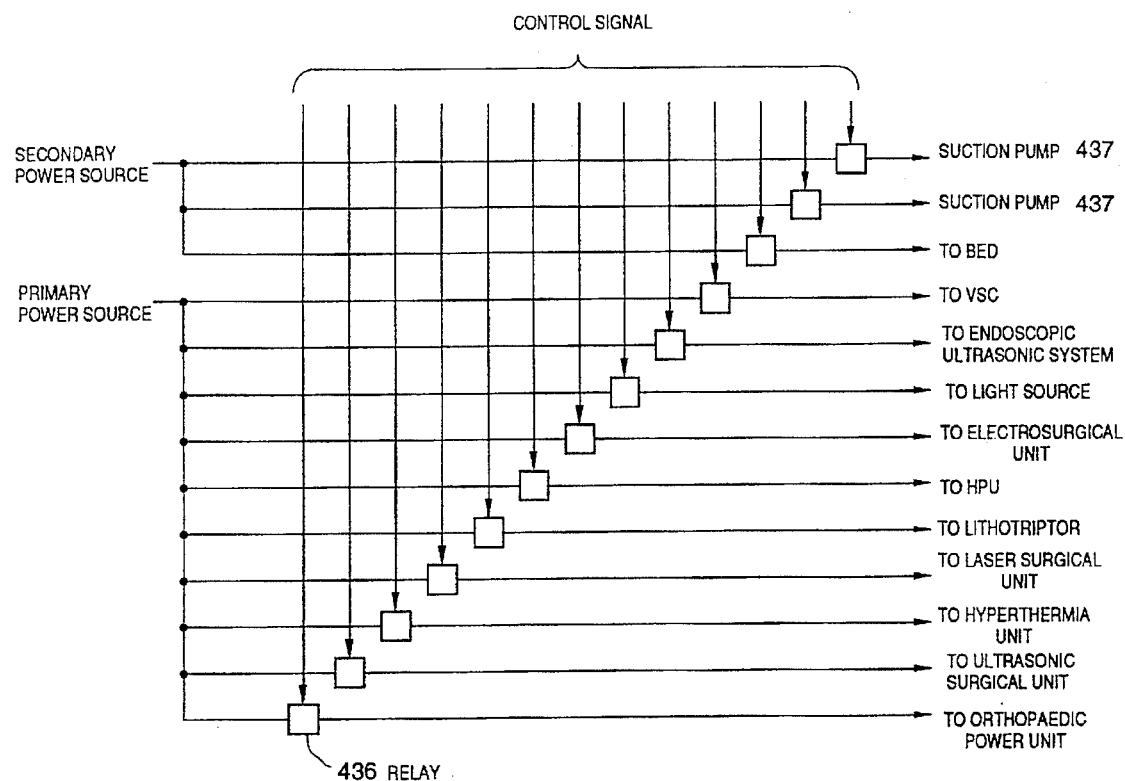
FIG. 57 is a diagram showing an arrangement of a group of equipment power-source control relays.

An internal arrangement of the group of equipment power-source control relays 434 is shown in FIG. 57.

The group of equipment power-source control relays 434 is provided with a plurality of relays 436. Respective devices of the aforesaid unit body 421 are connected to a power-source line through these relays 436 so that power source is supplied. A control signal from the controller 401 is inputted to the relays 436 through the I/O interface 432 so that ON/OFF is controlled by a control signal. Here, the bed 433 and a suction pump 437 connected to the endoscope are connected to a secondary power-source line. The VSC 406 of the unit body 421, the endoscopic ultrasonic system 407, the light source 408, the electrosurgical unit 410, the HPU 411, the lithotriptor 412, the hyperthermia unit 413, the laser surgical unit 414, the ultrasonic surgical unit 415 and the orthopedic power unit 416 are connected to the primary power-source line so that ON/OFF control of each power source is performed.

Furthermore, there are provided foot switch A 438 for turning on and off outputs from the electrosurgical unit 410, the HPU 411, the lithotriptor 412 and the like, and foot switch B 439 for turning on and off water supply at the HPU 411, which are connected to the I/O interface 432. It is possible to directly ON/OFF control an output from the device, and the like also by foot switch A 438 and foot switch B 439.

Operation of the thirteenth embodiment will next be described.

The controller 401 outputs a control picture plane which indicates various kinds of switches for operating various equipment, on the LCD panel 402 by graphic.

The controller 401 detects as to what switch of the control picture plane is depressed or pushed by the touch panel 404 which is provided on the LCD panel 402, and sends the control signal in accordance with the same to each equipment.

Figure 59:
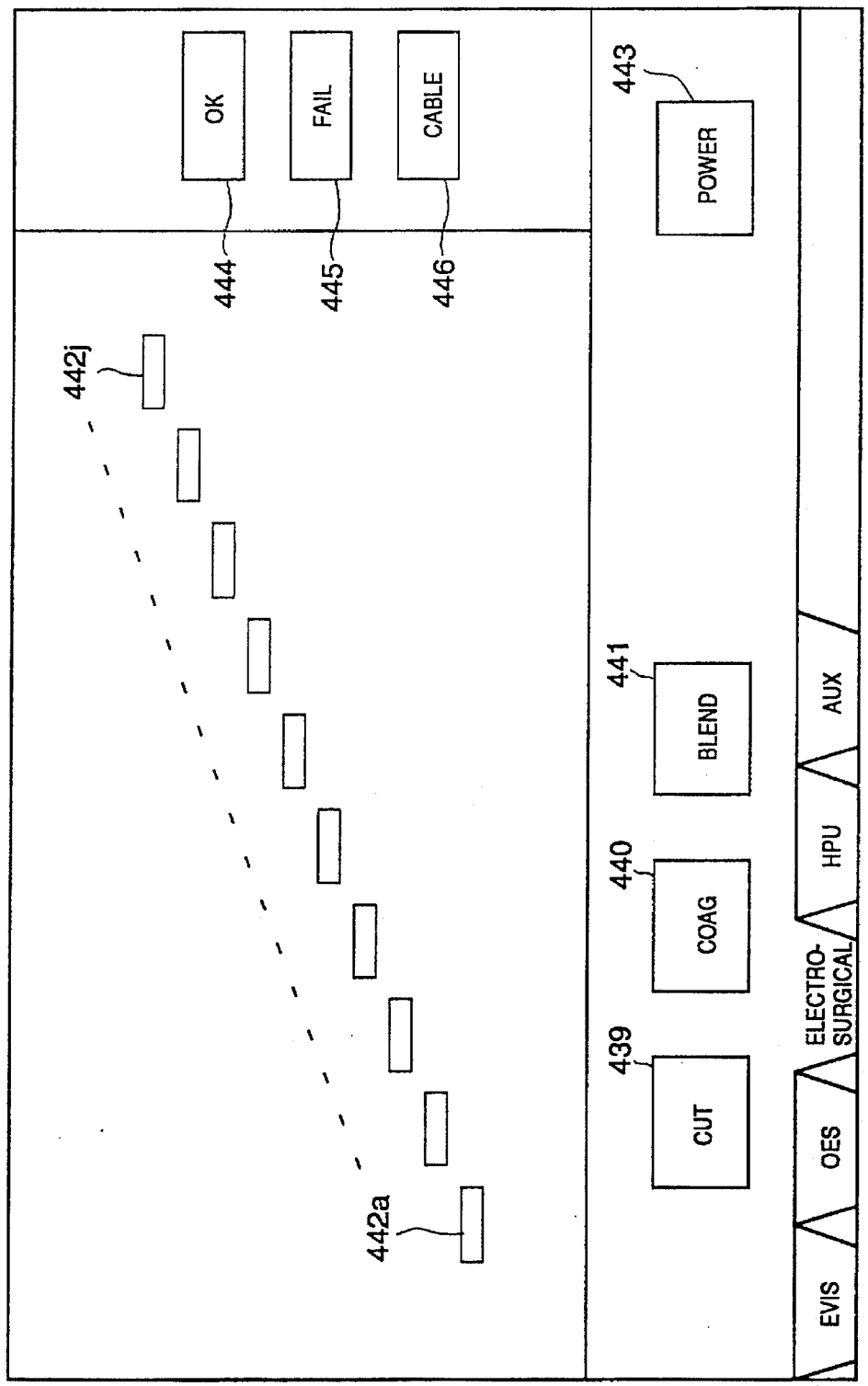
FIG. 59 is a diagram showing a control picture plane of an electrosurgical unit.

FIG. 59 shows the control picture plane of the electrosurgical unit 410. Control of the electrosurgical unit 410 will be described with reference to this control picture plane.

Here, sending and receiving of the control signal at the time, for example, an output waveform of an electric scalpel is selected will be described.

The control picture plane is provided with a CUT switch 439, a COAG switch 440 and a BLEND switch 441 that are switches for selecting modes of the output waveform of the electric scalpel.

Here, the "CUT" mode is a waveform mode for cutting off organization. The "COAG" mode (coagulate mode) is a waveform mode for solidifying organization to stop or arrest bleeding. The "BLEND" mode is a waveform mode in which two waveforms of "CUT" and "COAG" are mixed with each other.

The interface 403 scans the touch panel 404 to successively send switching information of the touch panel 404 to the controller 401. In a case where any one of the CUT switch 439, the COAG switch 440 and the BLEND switch 441 is pushed, the controller 401 analyzes to where of graphic the position of the pushed touch panel 404 corresponds. In a case, for example, where a portion of the CUT switch 439 is pushed, a command for setting the output waveform of the electric scalpel to the "CUT" mode is sent to serial expander A 405 as a control signal.

Figure 58:
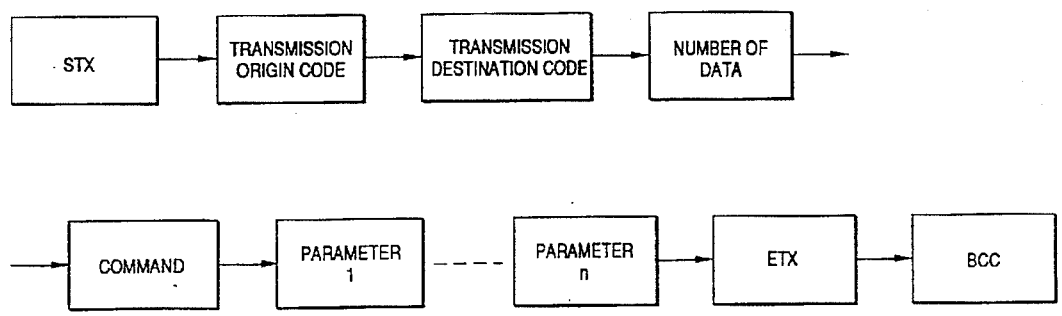
FIG. 58 is a diagram showing an example of format of a control signal for controlling an electric treatment device.

FIG. 58 shows an example of format of the control signal.

"STX" indicating beginning of a sentence is placed at the head. Transmission origin codes (the respective equipment have respective different codes thereof), transmission destination codes, the number of data and commands follow. Parameters follow only by the required number. In this example, for example, as the commands, it is assumed that setting of waveform: 30 H, setting of output: 31 H, bipolar/monopoly switching: 32 H, notification of warning: 33 H, and the test results: 34 H. In a case of setting of waveform, the parameter is assumed such that CUT: 30 H, COAG: 31 H, BLEND: 32 H, and inquiry: 34 H. Here, xxH expresses hexadecimal number.

In the setting of the waveform in this case, the parameter is one or a single. Further, "ETX" indicating the end of the sentence comes, and, lastly the entire check sum is affixed as BCC. By the way, a command string or column when the output waveform is set to "CUT" IS "03 F0 F1 02 30 30 02 48". In this connection, it was assumed that the code of the controller 401 was "F0", and the code of the electrosurgical unit 410 was "F1".

Moreover, in the control picture plane of the electrosurgical unit 410 in FIG. 59, the reference numerals 442a–442j denote switches for setting the output from the electric scalpel. In a case where the controller 401 detects that a portion of the output setting switch here is pushed or depressed, simultaneously with the aforementioned setting of waveform, a command for setting an output value corresponding to the switch is sent to serial expander A 405.

Serial expander A 405 analyzes to what or which equipment the received command is sent, and sends the analysis to the channel of the corresponding equipment by the form as it is.

In connection with the above, the arrangement may be such that the controller 401 sends the command string which periodically inquires the waveform and the output value, to the electrosurgical unit 410, receives an answer from the electrosurgical unit 410, and the results thereof are also displayed by the graphic output. Furthermore, in a case where the set value and the actual value in the apparatus are different from each other, the arrangement may be such that warning display is exhibited, or the group of equipment power-source control relays 434 is controlled from the I/O interface 432 to turn OFF the power source of the electrosurgical unit 410.

Further, the control picture plane of the electrosurgical unit 410 is provided with a power switch 443, a pair of displays 444 and 445 of test results of the electric scalpel, and warning display 446 at the time an S code (safety code) and a P plate (electrode on the side of patient) are not connected.

Data such as an operating condition and the like are sent from the electrosurgical unit 410 to the controller 401. On the basis of the results of the data, the controller 401 controls the electrosurgical unit 410 and displays warning. When the electric scalpel is tested before use or the like as to output check, the test results are sent to the controller 401, and the results of the test are displayed as being OK or FAIL by the rest result displays 444 and 445. Moreover, the S code is a code for feeding back high-frequency current to the electric scalpel from the endoscope so that the high-frequency current leaked from the electric scalpel to the endoscope does not flow toward an operator from the endoscope. The controller 401 displays CABLE by the warning display 446 when the S code is not connected to the endoscope from the electric scalpel, to warn the operator. Furthermore, also when the P plate is not connected to the electrosurgical unit, warning is performed by the warning display 446. Further, setting of selection of the bipolar electrode/monopoly electrode, and the like are performed by sending the control signal from the controller 401.

In this manner, the control signal is sent and received, whereby the controller 401 controls the electrosurgical unit 410.

In connection with the above, operation of the controller 401 in a case where the touch panel 404 is depressed is not necessarily limited to sending-out of the command by serial communication. For example, in a case where it is detected that the power switch 443 is depressed, in the present embodiment, the group of equipment power-source control relays 434 is controlled through the I/O interface 432, whereby turning-ON/OFF of the power source for the electrosurgical unit 410 is performed. Of course, an ON/OFF command function may be caused to be had to the electrosurgical unit to control the same by the command.

Further, format of the control signal is shown in FIG. 58 as an example. However, the format should not be limited to this format. The command itself may include a transmission origin and a transmitting origin as information. Alternatively, it is needless to say that the command is in accordance with standard protocol such as CSMA/CD, GP-IB and the like.

The control picture plane shown in FIG. 59 has a lower end portion thereof which functions as a change-over switch of the control picture plane. An EVIS is a switch for setting to an electronic scope control mode, and for primarily switching to a picture plane for controlling the video system center 406 and the like. An OES denotes a switch for setting to a fiber scope control mode and for primarily switching to a picture plane for controlling the light source 408. An ELECTRO-SURGICAL is a switch for setting to an electric scalpel control mode and for switching to a control picture plane of the electrosurgical unit 410. In FIG. 59, the control picture plane of the electrosurgical unit 410 is active. An HPU is a switch for setting to an HPU control mode for switching to a control picture plane of the HPU 411. An AUX is a switch for setting to an expansion-unit control mode, and for switching to a picture plane for primarily controlling the VTR 426 of the expansion unit 422 and the like. These switches are depressed, whereby the controller 401 switches the picture plane display to the respective control picture planes.

Figure 60:
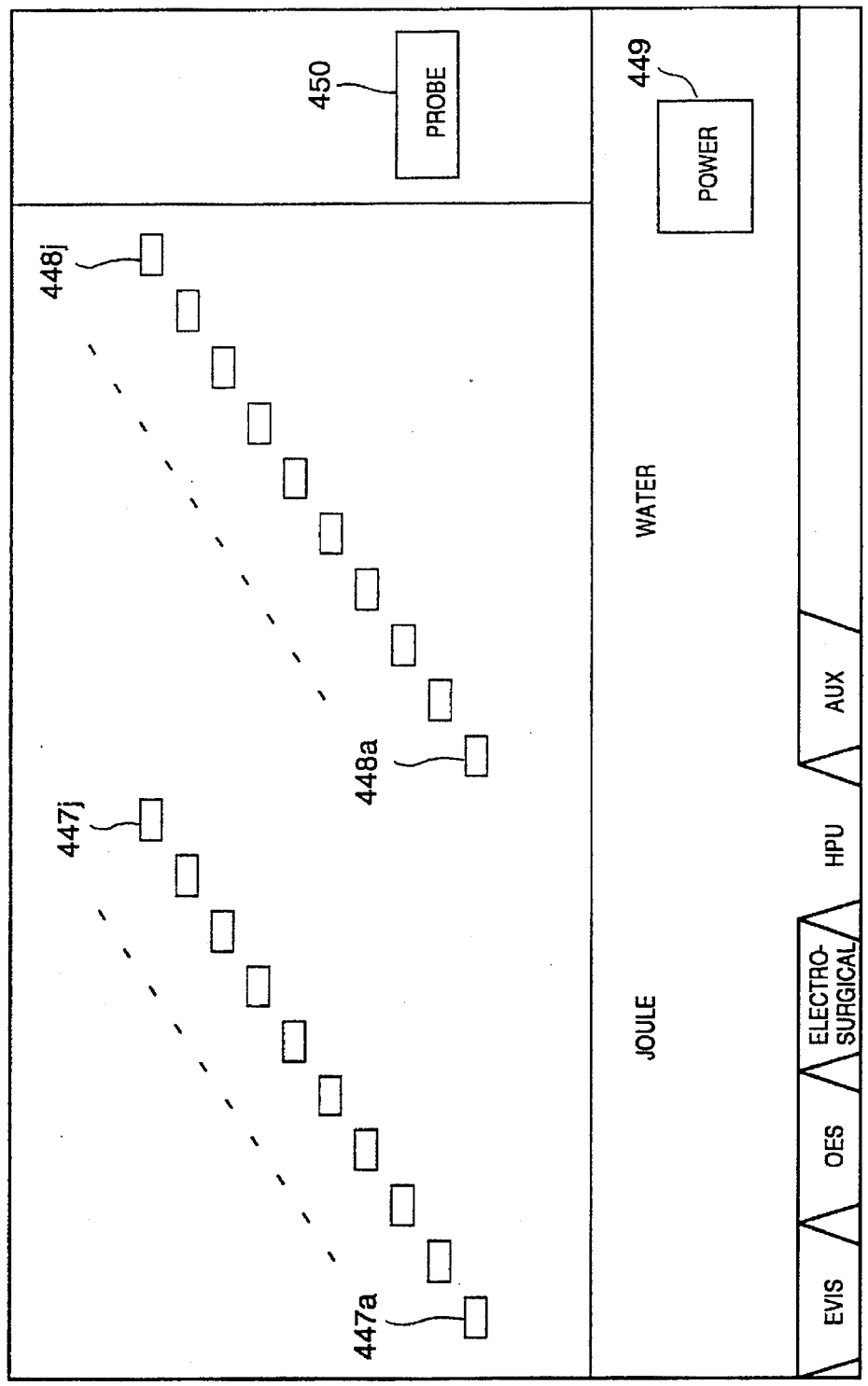
FIG. 60 is a diagram showing a control picture plane of a heatprobe unit.

The control picture plane of the HPU 411 will next be shown in FIG. 60. Control of the HPU 411 will be described with reference to the control picture plane.

Process from the time the touch panel 404 is depressed, to the time the controller 401 sends a command is similar to that in a case of the electrosurgical unit. Communication contents include setting of the output value, setting of water pressure, notification of non-connection of the probe, and the like.

The control picture plane of the HPU 411 is provided with setting switches 447a–447j for output energy of the heatprobe, and setting switches 448a–448j for water pressure of water discharged. In a case where it is detected that portions of these setting switches are depressed, the controller 401 transmits a command for setting an output value and water pressure corresponding to the switches, to serial expander A 405. Moreover, a power switch 449 and a warning display 450 are provided for displaying PROBE when the probe is not connected to the HPU 411, to warn the operator.

The controller 401 sends and receives the control signal with respect also to the HPU 411, to thereby perform control similarly to the electrosurgical unit 410.

Other devices similarly send and receive the control signal from the controller 401, to thereby perform various kinds of controls and perform display of an operating condition to the LCD panel 402. Although the control picture plane is omitted, communication contents in the various devices will hereunder be described.

The lithotriptor 412 is called also as an EHL (Electro-Hydraulic Lithotriptor), and is a device in which electric discharge is performed at a forward end of the probe within water accumulated in a body, to thereby generate water pressure to destroy a calculus or the like. The communication contents include setting of the discharge energy, discharge spacing or intervals, discharge pattern, notification of the probe un-connection and the like. If the lithotriptor is large in size, there is a lithotriptor which is in direct contact with a patient not through an endoscope to act upon the patient (called ESWL). Control in this case is also similar.

The hyperthermia unit 413 is a device which irradiates a microwave from a forward end of the probe, and temperature of an irradiated portion is detected by a temperature sensor and is fedback, whereby an affected or diseased part of cancer or the like is maintained to temperature at which there is no affection or influence to normal cells although the cancer dies out. Communication contents include setting of an output of the microwave, irradiating time and irradiating pattern setting, temperature setting, selective setting of the temperature sensor, notification of various kinds of warnings and the like.

The communication contents with respect to the endoscopic ultrasonic system 407 include setting of output frequency, setting of contrast of the output picture plane, setting of gain of outputted image, setting of display extent, freeze of the picture plane, release of a camera, ON/OFF of AGC, setting of STC, various kinds of warnings, and the like.

The communication contents with respect to the laser surgical unit 414 include setting of the output, setting of the outgoing pattern, setting of the outgoing time, warning and the like. The contents of warning include a temperature rise in cooling water, warning of the quantity of cooling water, and the like.

The ultrasonic surgical unit 415 is a device which performs suction while an ultrasonic piezoelectric transducer is applied to an affected or diseased part, to thereby cut off organization. Function of sending water to cool the forward end of the probe and the electric scalpel for arresting blood are build-in. The communication contents include setting of ultrasonic outputting, setting of the electric scalpel output, waveform setting of electric scalpel output, setting of a suction force, setting of electrode selection of monopoly/bipolar of the electric scalpel, setting of the quantity of sent water, and the like.

The orthopedic power unit 416 is a piece of equipment for shaving a bone or the like by rotating drill-like teeth, and has also a function for sucking or drawing shaved organization. The communication contents include setting of the number of revolutions or revolving speed, setting of a rotating direction, setting of suction pressure, various kinds of warnings and the like.

The pulse oximeter 418 is an equipment for measuring oxygen concentration in blood and a pulse frequency as organism information. The communication contents include start/end of measurement, setting of measurement intervals, ON/OFF of warning output in a case where a measurement value exceeds predetermined values (upper-limit value and lower-limit value), setting of the upper-limit value and the lower-limit value, notification of the measurement value, various kinds of warnings and the like. The controller 401 receives data from the pulse oximeter 418, to display the contents of the measurement values, various kinds of warnings at abnormality and the like on the LCD panel 402. In this connection, judgment as to whether or not the measurement value exceeds the predetermined values may be performed on the side of the controller.

Communication contents of the blood pressure gauge 419 include notification of blood pressure and a pulse frequency serving as organism information of a patient, setting of measurement intervals, ON/OFF of a warning output in a case where a measurement value exceeds predetermined values, (upper-limit value and lower-limit value), setting of the upper-limit value and the lower-limit value, various kinds of warnings and the like. The controller 401 receives data from the blood pressure gauge 419, to display the contents of measurement values, various kinds of warnings upon abnormality and the like onto the LCD panel 402. In this connection, judgment as to whether or not the measurement value exceeds the predetermined values may be performed on the side of the controller.

The communication contents of the card reader 417 include setting of the kind or type of cards, notification of reading data and the like.

Further, the controller 401 sends the control signal to the video-signal switcher A 420 through the I/O interface 432 to perform control of switching of an input and an output to and from the video-signal switcher A 420. By doing so, the video-signal switcher A 420 switches video signals from the video system center 406, the endoscopic ultrasonic system 407 and the expansion unit 422 and a video signal returned form the monitor 423, and switches the outputs to the expansion unit 422 and the monitor 423. Signal transition or conversion between them is also performed depending upon how to switch, in order that the video signal handles or treats signals such as RBG, Y/C, composite and the like. In this connection, it is of course that control of them may be so arranged as to be performed by serial communication through the serial expander A 405.

The controller 401 performs sending and receiving of the control signal with respect also to the bed 433 and the level detecting unit 435 through the I/O interface 432, to perform control of the bed 433 and monitoring or supervisory of the level detecting unit 435.

The communication contents of the bed 433 include control of sliding in vertical and transverse directions, notification of upper and lower positions, notification of a transverse position, various kinds of notifications, and the like. These functions may be performed by serial communication.

The controller 401 displays a control picture plane of the bed 433 on the LCD panel 402. When it is detected that an "upper" switch on the touch panel 404 is depressed, an "upper" signal on the I/O port is turned ON, and is turned OFF when the switch is released. Moreover, in a case where it is detected that an "auto" switch on the touch panel 404 is depressed, vertical movement and transverse sliding are controlled while the vertical position and transverse position is so monitored as to become a predetermined set value. In this connection, the arrangement may be such that a controller is provided on the bed 433 per se, and, when "AUTO" is depressed, the set value is exchanged between the bed 433 and the controller 401 to control the position.

The level detecting unit 435 is one for performing drawing or suction by a suction pump 437 illustrated in FIG. 57, to detect the quantity of liquid accumulated in a bottle. When the drawn or sucked liquid is accumulated a predetermined quantity in the bottle, a signal notifying that the liquid is accumulated from the level detecting unit 435 is sent to the controller 401. Of course, the arrangement may be such that a controller is provided on the level detecting unit itself, processing is enabled intelligently in the level detecting unit, such as being capable of being judged by itself, and setting of a detecting value of the level by communication from the controller 401. Further, the detecting value should not be limited to one, but may be two or more.

As described above, the controller 401 controls various built-in equipments through the I/O interface 432 and the serial expander A 405 and outputs the video signals from the video system center 406 or the endoscopic ultrasonic system 407 or the expansion unit 422 to the monitor 423 through video-signal switcher A 420, to display the image.

Similarly to the unit body 421, also in the expansion unit 422, the control signal from the controller 401 is sent to the filing device 425, the VTR 426, the video printer 427, the monitor photo unit 428, the card reader 429, the bar code reader 430 and video-signal switcher B 431 through serial expander B 424, to perform control.

Communication contents of the various devices of the expansion unit 422 will hereunder be described.

Communication contents of the filing device 425 include release that is a trigger signal of image memory or storing, exchange of patient data, a retrieval command of image and the like. Furthermore, in a case where the filing device 425 has function of image processing, the communication contents include setting of color, setting of constant in image processing, and the like.

Communication contents of the card reader 429 and the bar code reader 430 are similar to those of the card reader 417 within the unit body.

Communication contents of the video-signal switcher B 431 include setting of switching in exchange of signals which include a video signal to and from the unit body 421, a video signal to and from the filing device 425, a video signal to and from the VTR 426, a video signal to and from the video printer 427 and a video signal to and from the monitor photo device 428. The video-signal switching unit B 431 performs signal switching and, in addition thereto, simultaneously performs conversion between different video signals.

In connection with the above, the filing device, the VTR, the video printer, the monitor photo device or the like connected to the expansion unit 422 in the present embodiment is illustrated as being a signal. However, it should not be limited to a single, but it is similar if there are a plurality.

Further, in the present embodiment, the serial communication is RS-232C. However, the embodiment should not be limited to RS-232C. The communication may be LAN of 10BASE-T, a Token Ring or the like. Moreover, the control signal should not be limited to the serial communication, but may be parallel communication such as GP-IB, SCSI or the like.

As described above, according to the present embodiment, it is possible to operate and control, in centralized manner, not only the video system center and the light source used in endoscope observation, but also the electric treatment device for performing various kinds of treatments or processings by control means which includes a controller, an LCD panel and a touch panel.

Figure 61:
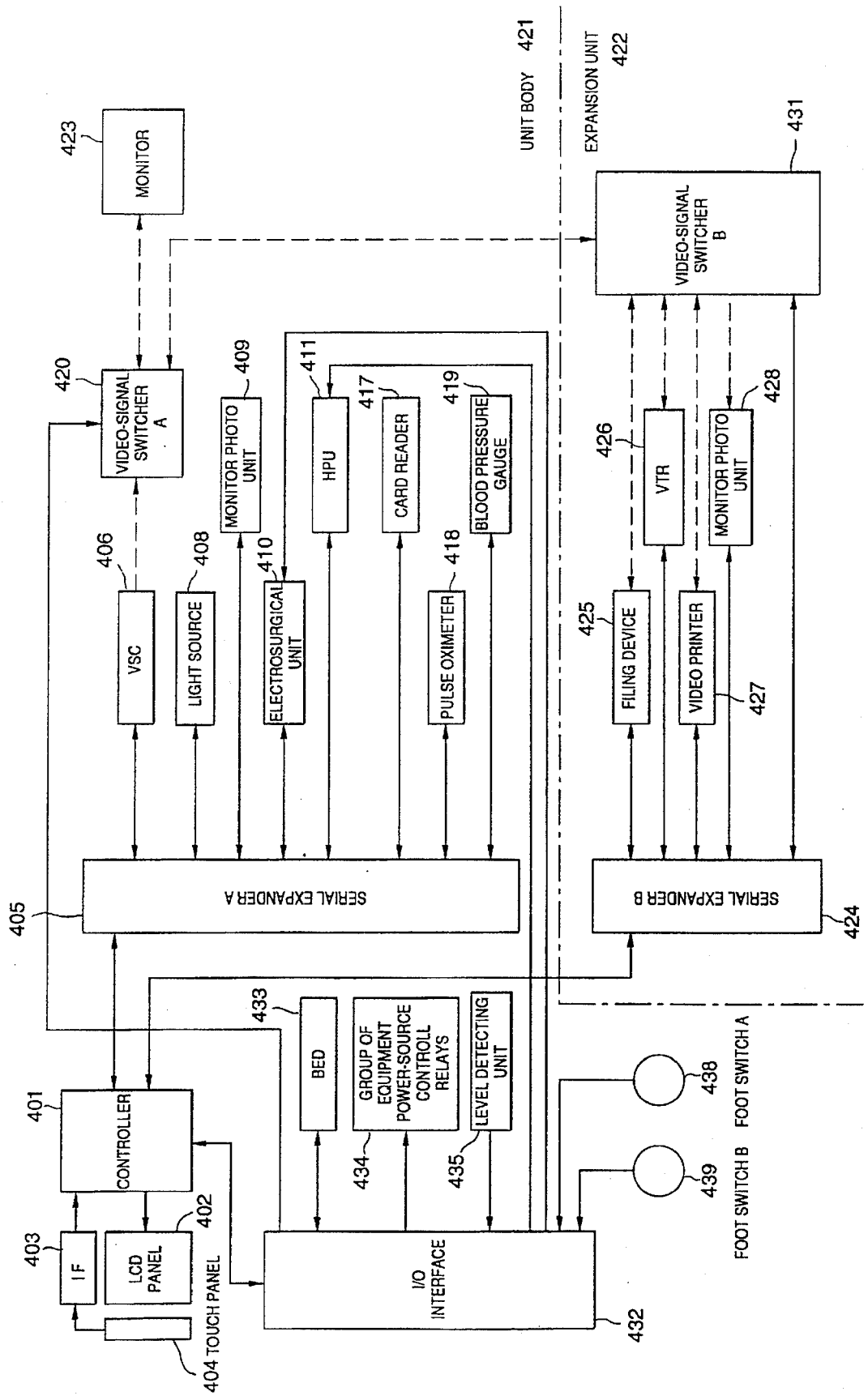
FIG. 61 is a block diagram showing an entire arrangement of an endoscope system according to a fourteenth embodiment of the invention.

FIG. 61 shows a fourteenth embodiment of the invention.

The fourteenth embodiment is an example which includes only necessary minimum devices when endoscope inspection is performed, including medical treatment, among constitutional elements in the thirteenth embodiment. Arrangement of the system is similar to that of the thirteenth embodiment, except for a different number of peripheral devices.

Furthermore, in the present embodiment, foot switch A 438 for turning ON and OFF an output from an electrosurgical unit 410 and an output from an HPU 411, and foot switch B 439 for turning ON and OFF water supply by the HPU 411 are connected to an I/O interface 432, and the electrosurgical unit 410 and the HPU 411 are connected to the I/O interface 432. Signals from foot switch A 438 and foot switch B 439 are sent directly to the electrosurgical unit 410 and the HPU 411 by the I/O interface 432 not through a controller 401. That is, in the present embodiment, outputs from the electrosurgical unit 410 and the HPU 411 can directly be ON-and-OFF controlled by foot switch A 438 and foot switch B 439, by way of runaway and the like on the side of a serial interface which controls various devices.

Operation of each piece of equipment and the control contents are similar to those of corresponding parts in the thirteenth embodiment. Also in the present embodiment, it is possible to operate and control, in a centralized manner, electric treatment devices such as the electrosurgical unit, the HPU and the like together with a video system center which is used for endoscope observation.

Figure 62:
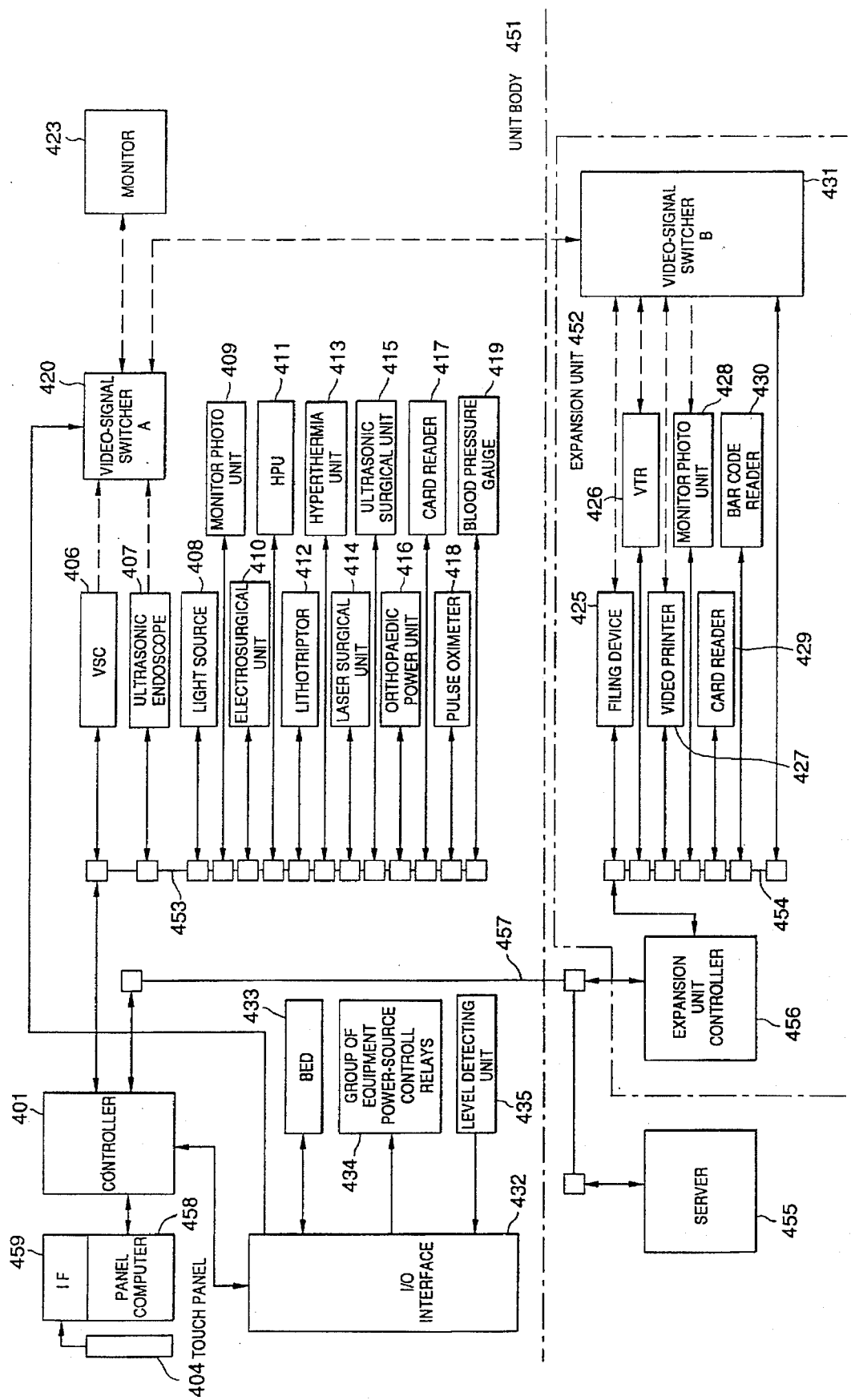
FIG. 62 is a block diagram showing an entire arrangement of an endoscope system according to a fifteenth embodiment of the invention.

FIG. 62 shows a fifteenth embodiment of the invention.

In the thirteenth embodiment, peripheral devices are connected to a controller through a serial expander by star-type connection. On the contrary, the fifteenth embodiment is an example which utilizes a bus-type connection.

LANs 453 and 454 of Arc Net are formed respectively within a unit body 341 and an expansion unit 452, and the peripheral devices are connected to the LANs 453 and 454. Moreover, a server 455 is provided on the outside of the unit. The expansion unit 452 is provided with an expansion-unit controller 456. A controller 401 of the unit body 451, the expansion-unit controller 456 and the server 455 are connected to each other by a LAN 457 of 10BASE-2.

The LAN 453 of the unit body 451 is connected to the controller 401. Moreover, the LAN 454 of the expansion unit 452 is connected to the extension-unit controller 456 and is connected to the controller 401 through the LAN 457 which connects the controller 401 and the expansion-unit controller 456 to each other.

In connection with the above, the square form in FIG. 62 indicates branch of the LAN. Various devices connected to the LAN are provided with an interface.

A panel computer 458 having the LCD is connected to the controller 401. A touch panel 404 is connected to the panel computer 458 through an interface 459.

In the fifteenth embodiment, the panel computer 458 receives a command from the controller 401, to display a control picture plane on an LCD itself. Furthermore, the panel computer 458 detects where of the touch panel 404 provided on the LCD is depressed. The panel computer 458 judges what switch of the control picture plane is depressed and correspondingly sends a control signal to the controller 401. That is, the panel computer 458 intelligently treats or deals with a signal from the touch panel 404, and sends a command as to what function is selected, to the controller 401. By doing so, it is possible to reduce a load on the controller 401.

The rest of the arrangement of the system is similar to that of the thirteenth embodiment.

Operation of each of the various pieces of equipment and the contents of the control are similar to the corresponding parts of the thirteenth embodiment. Even in a case where the LAN is arranged in this manner to send and receive the control signal, it is possible to operate and control, in centralized manner, the electric treatment or handling device such as the electrosurgical unit, the HPU and the like together with the video system center which is used in endoscope observation.

In connection with the above, the types or kinds of the LANs in the present embodiment should not be limited to 10BASE-2 and the like. It has no objection to use an FDDI or the like. Moreover, it is similar to the thirteenth embodiment that the number of the expansion units may be a plural, and the arrangement of built-in equipment of the expansion unit is not in accordance with the present embodiment.

According to the present invention, it will be apparent that different embodiments can be formed based on the broadest interpretation of the present invention without departing from the spirit and scope of the invention. The invention will be confined to the appended claims but not be restricted by the specific embodiments.

What is claimed is:

1. An endoscope system including an endoscope, a light source for supplying illuminating light to said endoscope, and a video signal processor for processing an image signal obtained by said endoscope, said endoscope system comprising:

an electric treatment device combined with said endoscope for performing electric treatment;

a centralized operation computer including a display for operating at least one of peripheral equipment including said light source, said video signal processor and said electric treatment device, said centralized operation computer having a touch panel serving as an input means on the display, and outputting a command for operating at least one of said peripheral equipment by touching a given area on said touch panel; and a control computer connected to said light source, and said video signal processor, said electric treatment device, and said centralized operation computer via interfaces and providing centralized control for said light source, said video signal processor and said electric treatment device based on a command from said centralized operation computer, wherein either one of said centralized operation computer and said control computer can set an area on said touch panel, and wherein said centralized operation computer and said control computer monitor each other such that a graphical display of an operation panel of said peripheral equipment appearing on the display does not deviate from a touched state of said touch panel sensed by said control computer.

2. An endoscope system according to claim 1, wherein said endoscope is provided with a solid-state imaging device which is located at an image forming position of an objective optical system installed at a distal end of an insertion tube.

3. An endoscope system according to claim 1, wherein said endoscope is provided with a TV camera which is installed on an external side of an eyepiece to be freely detachable.

4. An endoscope system according to claim 1, wherein said centralized control means has such control modes as a fiberscope light source control mode and an electronic endoscopic light source control mode.

5. An endoscope system according to claim 1, wherein said centralized control means has such control modes as a light source control mode for controlling a light source and a video signal processing mode for processing a video signal.

6. An endoscope system according to claim 1, wherein said centralized operation means includes a power operation means for turning on or off power supplies of a plurality of peripheral equipment; and said centralized control means includes a switching means for turning on or off at least said power supplies of said peripheral equipment based on a command sent from said centralized operation means.

7. An endoscope system according to claim 6, wherein said centralized control means includes a switching means for turning on or off at least said lights in said endoscope system room based on a command sent from said centralized operation means.

8. An endoscope system according to claim 6, wherein said centralized control means includes a light control means for controlling at least a quantity of light of said lights in said endoscope system room based on a command sent from said centralized operation means.

9. An endoscope system according to claim 6, wherein said centralized control means includes:

a hue detection means for picking up a video signal of an endoscopic image to detect the levels of color signals;

a determination means for assessing the levels of said color signals detected to determine whether or not an endoscope is being used for examination; and an illumination control means for controlling said lights in said endoscope system room based on the determinant of said determination means.

10. An endoscope system according to claim 1, wherein said centralized operation computer is a light-weight computer in which a display and a computer control is formed as a unit.

11. An endoscope system according to claim 1, wherein said centralized operation means is capable of setting an output level of at least said electric treatment device with respect to said electric treatment device.

12. An endoscope system according to claim 11, wherein said electric treatment device is an electrosurgical unit.

13. An endoscope system according to claim 12, wherein said centralized operation means is capable of setting an output level of an electrosurgical unit and capable of setting, in selection, an output mode of an electric scalpel at least from a cut mode for cutting off organization and a coagulate mode for solidifying the organization.

14. An endoscope system according to claim 13, wherein said system further includes an ON-OFF switch for an output from said electrosurgical unit, and wherein a signal from said ON-OFF switch is directly inputted to said electrosurgical unit not through said centralized control means.

15. An endoscope system according to claim 14, wherein said ON-OFF switch is a foot switch.

16. An endoscope system according to claim 11, wherein said electric treatment device is a heat probe unit.

17. An endoscope system according to claim 16, wherein said centralized operation means is capable of setting a heat output level of said heat probe unit and setting a quantity of water which is discharged from said heat probe unit.

18. An endoscope system according to claim 17, wherein said system further includes and ON-OFF switch for the heat output from said heat probe unit and an ON-OFF switch for the water output from said heat probe unit, and wherein signals from the ON-OFF switch are directly inputted to said heat probe unit not through said centralized control means.

19. An endoscope system according to claim 1, wherein said centralized operation means includes output level setting means for setting an output level of said electric treatment device, and wherein said endoscope system comprises an ON-OFF switch for operation of said electric treatment device separately from said centralized operation means.

20. An endoscope system according to claim 19, wherein signals from the ON-OFF switch are supplied to said electric treatment device not through said centralized control means.

21. An endoscope system according to claim 1, wherein said light source, said video signal processor and said electric treatment device are connected to said centralized control means through a first serial expansion means, said centralized control means and said first serial expansion means capable of performing serial communication of at least a control signal, and said first serial expansion means is connected to said light source, said video signal processor and said electric treatment device, to perform serial communication of at least the control signal.

22. An endoscope system according to claim 21, wherein said system further includes an image recording device and/or image print device for recording an image from an endoscope device which is not used in proximity to said endoscope, and wherein said centralized control means is connected to said image recording device and/or said image print device, through a second serial expansion means to perform serial communication of at least the control system.

23. An endoscope system according to claim 1, wherein said light source, said video signal processor and said electric treatment device are connected to said centralized control means through a first local area network connecting line.

24. An endoscope system according to claim 23, wherein said system further includes an image recording device and/or an image print device for recording an image from the endoscope, and wherein said centralized control means is connected to said image recording device and/or said image print device through a second local area network connecting line.

25. An endoscope system according to claim 1, wherein said system further includes detecting means for detecting organism information of a patient, and wherein said centralized control means receives detecting results from said detecting means so as to be capable of displaying said organism information on said display means.

26. An endoscope system according to claim 1, wherein said system further includes detecting means for detecting organism information of a patient, and wherein said centralized control means receives detecting results from said detecting means to issue a warning upon abnormality of said organism information, to said display means.

27. An endoscope system according to claim 25, wherein said detecting means is a pulse oximeter and/or a blood pressure gauge.

28. An endoscope system according to claim 1, wherein said electric treatment device is a lithotriptor.

29. An endoscope system according to claim 1, wherein said electric treatment device is a hyperthermia unit.

30. An endoscope system according to claim 1, wherein said electric treatment device is an ultrasonic surgical unit.

31. An endoscope system according to claim 1, wherein said electric treatment device is an orthopedic power unit.

* * * * *